(12) United States Patent
Weiner et al.

(10) Patent No.: US 10,786,291 B2
(45) Date of Patent: Sep. 29, 2020

(54) PROXIMAL BUNION RESECTION GUIDES AND PLATES AND METHODS OF USE

(71) Applicant: NEXTREMITY SOLUTIONS, INC., Warsaw, IN (US)

(72) Inventors: Lon S. Weiner, Rumson, NJ (US); Stuart D. Katchis, Scarsdale, NY (US); John R. Pepper, Cheshire, CT (US); Jorge A. Montoya, Berkeley Heights, NJ (US); Ryan Schlotterback, Fort Wayne, IN (US)

(73) Assignee: Nextremity Solutions, Inc., Warsaw, IN (US)

( * ) Notice: Subject to any disclaimer, the term of this patent is extended or adjusted under 35 U.S.C. 154(b) by 718 days.

(21) Appl. No.: 15/441,820

(22) Filed: Feb. 24, 2017

(65) Prior Publication Data

US 2017/0164989 A1   Jun. 15, 2017

Related U.S. Application Data

(63) Continuation of application No. PCT/US2015/047490, filed on Aug. 28, 2015.
(Continued)

(51) Int. Cl.
*A61B 17/80* (2006.01)
*A61B 17/15* (2006.01)
(Continued)

(52) U.S. Cl.
CPC .......... *A61B 17/8061* (2013.01); *A61B 17/14* (2013.01); *A61B 17/151* (2013.01);
(Continued)

(58) Field of Classification Search
CPC ............ A61B 17/8061; A61B 17/1775; A61B 17/8095; A61B 17/151
See application file for complete search history.

(56) References Cited

U.S. PATENT DOCUMENTS

| | | |
|---|---|---|
| 5,021,056 A | 6/1991 | Hofmann et al. |
| 5,662,656 A | 9/1997 | White |

(Continued)

FOREIGN PATENT DOCUMENTS

| | | |
|---|---|---|
| EP | 2685915 B1 | 4/2017 |
| WO | 2011109127 A1 | 9/2011 |

(Continued)

OTHER PUBLICATIONS

Supplementary European Search Report for European Application No. 15835565.1 dated Apr. 4, 2018.
(Continued)

*Primary Examiner* — Andrew Yang
(74) *Attorney, Agent, or Firm* — Heslin Rothenberg Farley & Mesiti P.C.; Victor A. Cardona, Esq.

(57) ABSTRACT

Bone plate systems, resection guides, implants, and methods are disclosed. A bone plate system may include a plate including a plurality of openings and a resection guide. A plate may include a body with a first end and a second end, at least two openings in the body, a first opening positioned in the first end and a second opening positioned in the second end, and an alignment marking disposed on a surface of the body. A guide may include a body with a first end and a second end, at least one first opening in the first end of the body, and at least one second opening in the second end of the body. Surgical methods for using the bone plate system, resection guides, and implants are also disclosed.

9 Claims, 49 Drawing Sheets

Related U.S. Application Data

(60) Provisional application No. 62/151,758, filed on Apr. 23, 2015, provisional application No. 62/043,268, filed on Aug. 28, 2014.

(51) Int. Cl.
*A61B 17/16* (2006.01)
*A61B 17/17* (2006.01)
*A61B 17/14* (2006.01)
*A61B 17/56* (2006.01)

(52) U.S. Cl.
CPC ...... *A61B 17/1682* (2013.01); *A61B 17/1775* (2016.11); *A61B 2017/565* (2013.01)

(56) References Cited

U.S. PATENT DOCUMENTS

| | | |
|---|---|---|
| 5,935,128 A | 8/1999 | Carter et al. |
| 6,423,061 B1 | 7/2002 | Bryant |
| 10,258,351 B2 * | 4/2019 | Biedermann ...... A61B 17/1728 |
| 2007/0276383 A1 * | 11/2007 | Rayhack ................ A61B 17/15 606/86 B |
| 2007/0299452 A1 | 12/2007 | Curry |
| 2008/0015590 A1 | 1/2008 | Sanders et al. |
| 2009/0228047 A1 | 9/2009 | Derouet et al. |
| 2012/0303033 A1 | 11/2012 | Weiner et al. |

FOREIGN PATENT DOCUMENTS

| | | |
|---|---|---|
| WO | 2012123758 A1 | 9/2012 |
| WO | 2014105750 A1 | 7/2014 |

OTHER PUBLICATIONS

International Search Report and Written Opinion of the International Searching Authority issued in PCT Application No. PCT/US2015/047490 dated Nov. 24, 2015.

* cited by examiner

100

100

200

200

300

300

400

500

550

550

600

600

700

800

800

800

PROXIMAL BUNION RESECTION GUIDES AND PLATES AND METHODS OF USE

CROSS REFERENCE TO RELATED APPLICATION

This application claims priority benefit to PCT Application No. PCT/US2015/047490 filed Aug. 28, 2015, which claimed priority benefit to U.S. provisional application Nos. 62/043,268 filed Aug. 28, 2014 and 62/151,758 filed Apr. 23, 2015, all of which are incorporated herein by reference in their entireties.

FIELD OF THE INVENTION

The present invention relates to general surgery, and more particularly orthopedic surgery. More specifically, but not exclusively, the present invention concerns devices and implants used during surgery for resecting bones.

BACKGROUND

One such type of bone resection is bunion deformities which are generally found on a person's foot, more specifically they are found on a person's toes. The bunion is a disease of the joint and soft tissue. A bunion deformity or hallux abducto valgus deformity results from the big toe deviating laterally toward the patient's smallest toe. Due to the lateral movement of the big toe, the first metatarsal bone angles toward the smaller toes on the patient's foot causing the first metatarsal bone to move out of alignment. Bunions may become irritating and in some cases very painful during walking and other weight bearing activities. Bunions may also be painful and debilitating condition that prevents wearing shoes. Genetics and poor shoe design are the causes. The angle between the metatarsal of the second digit is a means to quantify the degree of deformity.

Painful bunions are corrected by surgical soft tissue management and surgical bone reforming. The first metatarsal is corrected by sectioning it with a saw, and moving the head laterally. There are numerous cut locations from the proximal to distal regions, namely the chevron, Ludloff, Mau and proximal. The bones are shifted, and held in place with screws, staples or plates. Sometimes adjacent joints are fused to stabilize the re construction.

Recovery means limited ambulation and is lengthy and painful. Causes of slow healing are multifactorial and include large loads on bones, difficult to position cuts in proper orientation, and difficult to hold bones in close approximation to create a stable and tight surface for osteogenesis. The alignment of bone and plates is challenging, as the bones are relatively small.

Present solutions are conventional plates, and compressing and non compressing screws, staples and more recently formed plates. These utilize a step wise approach to the technique where the cutting is done before and separate from the joining. There are no repeatable landmarks to use in this process.

SUMMARY

In one aspect, provided herein is a bone plate system. The p bone plate system may include, for example, a plate including a plurality of openings and a resection guide.

In another aspect, provided herein is a surgical method for using a proximal bunion resection system. The method may include, for example, obtaining a bone plate system including a plate and a guide, positioning the guide onto a patient's bone, inserting at least one fixation device through the guide and into the bone, forming a resection locator on the bone, resecting the bone into a first bone portion and a second bone portion, positioning the plate on the first bone portion and the second bone portion, and securing the plate to the first bone portion and the second bone portion.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

DETAILED DESCRIPTION

Generally stated, disclosed herein are embodiments of resection plates, guides, and systems. Further, methods of using the resection plates, guides, and systems are also disclosed.

In this detailed description and the following claims, the words proximal, distal, anterior, posterior, medial, lateral, superior, and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Figure 1:
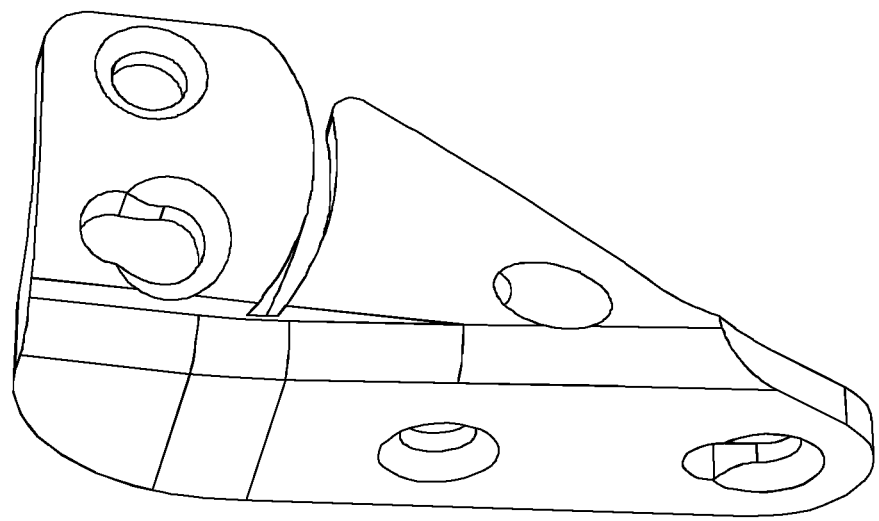
FIG. 1 is a top perspective view of a resection plate, in accordance with an aspect of the present invention.
Figure 2:
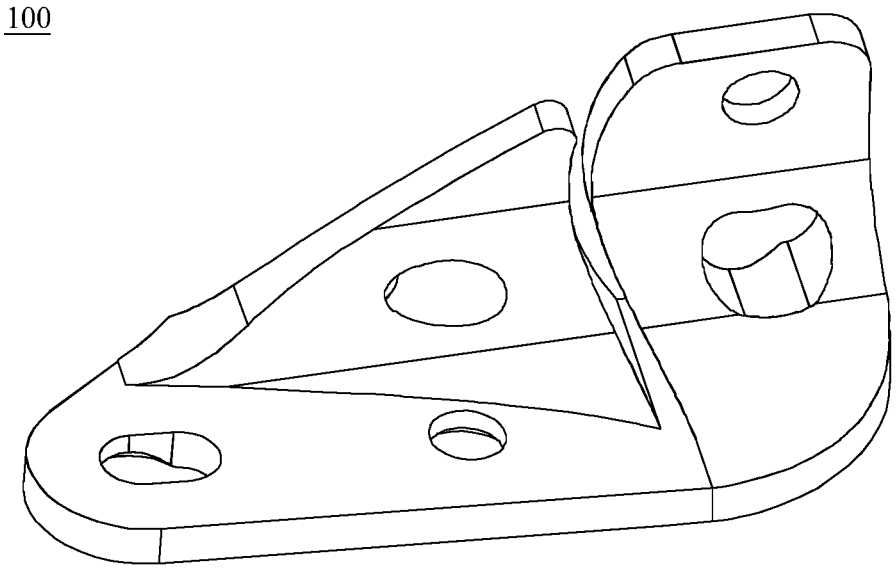
FIG. 2 is a bottom perspective view of the resection plate of FIG. 1, in accordance with an aspect of the present invention.
Figure 3:
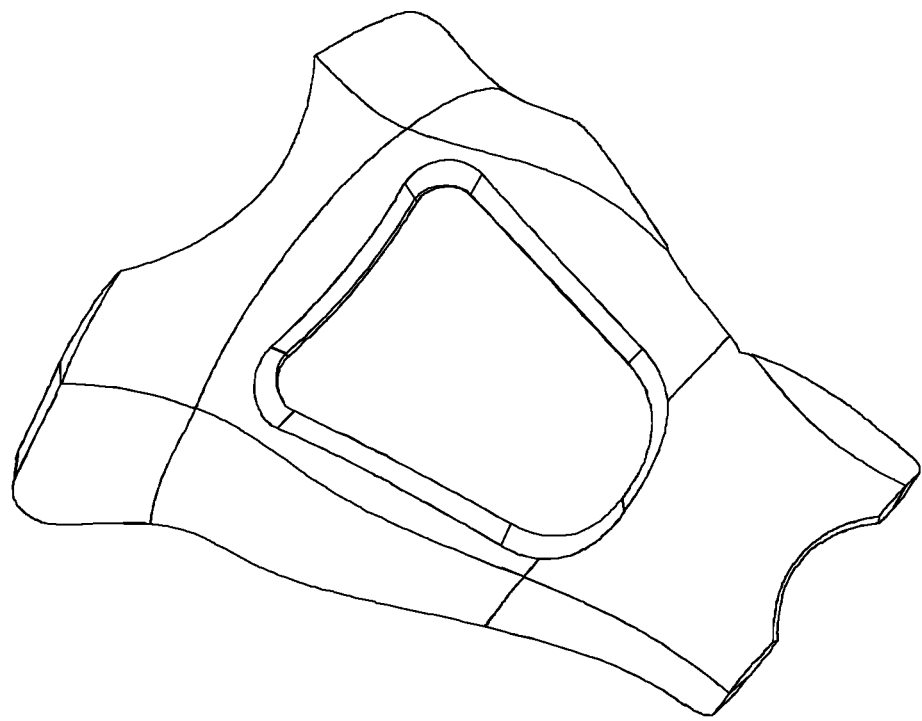
FIG. 3 is a top perspective view of another resection plate, in accordance with an aspect of the present invention.
Figure 4:
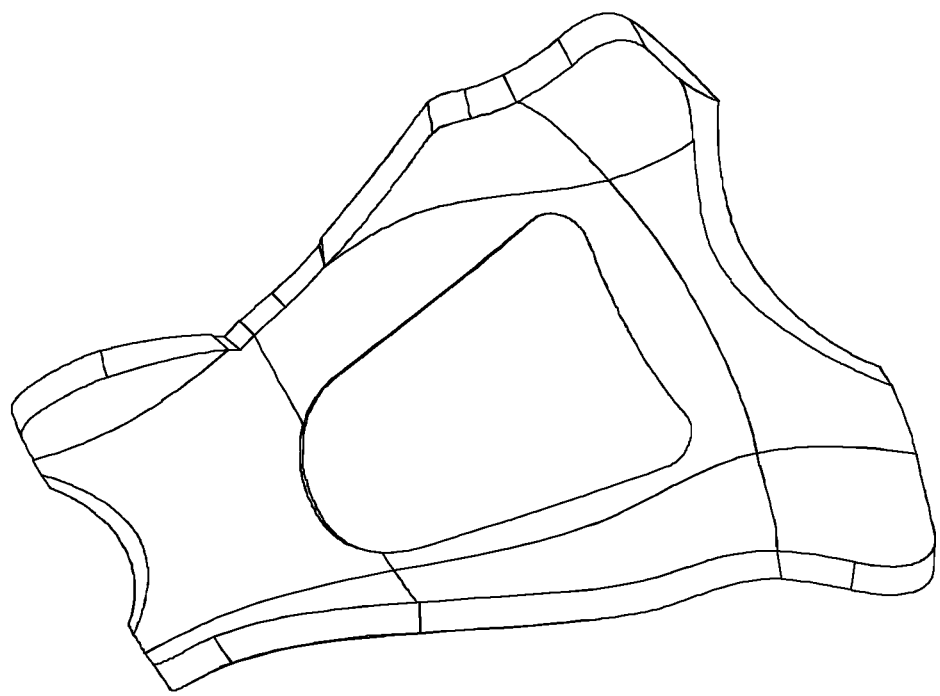
FIG. 4 is a bottom perspective view of the resection plate of FIG. 3, in accordance with an aspect of the present invention.
Figure 5:
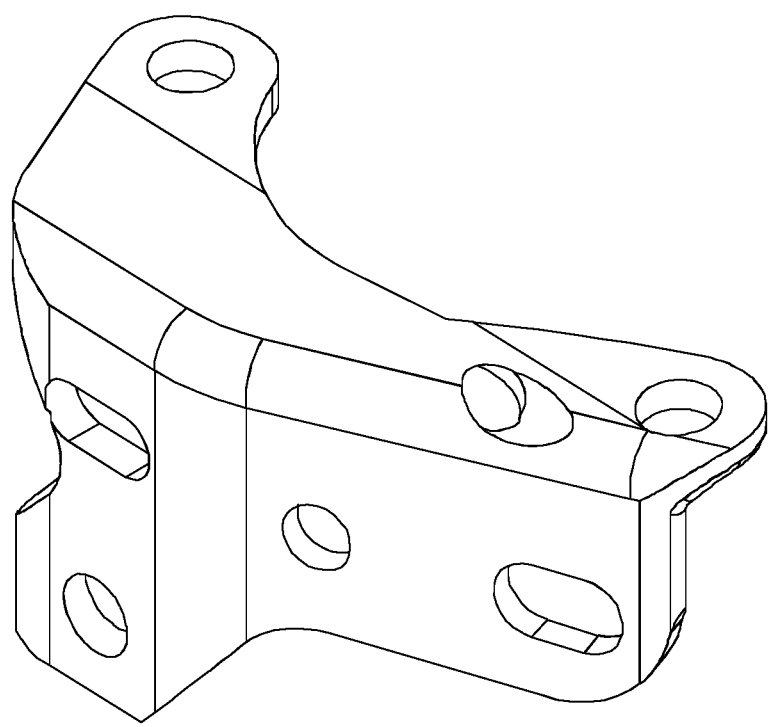
FIG. 5 is a top perspective view of yet another resection plate, in accordance with an aspect of the present invention.
Figure 6:
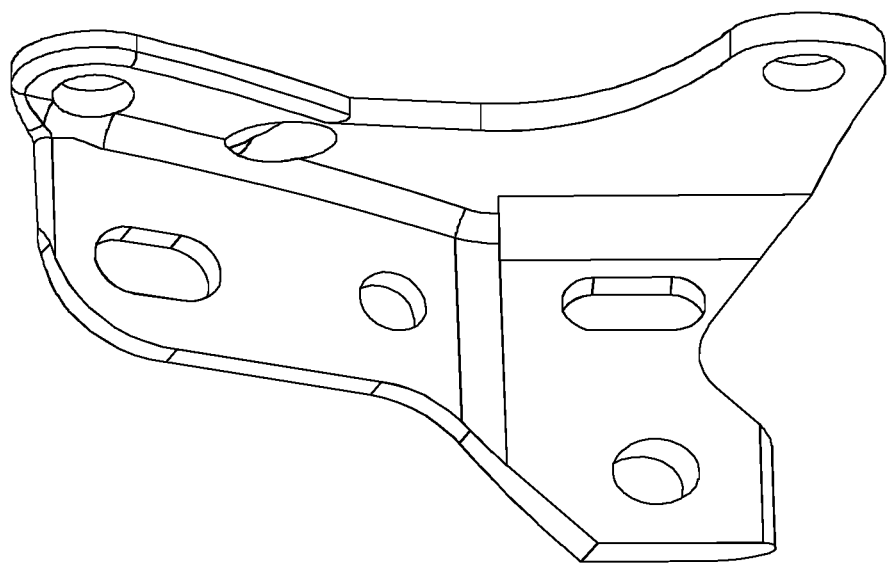
FIG. 6 is a bottom perspective view of the resection plate of FIG. 5, in accordance with an aspect of the present invention.
Figure 7:
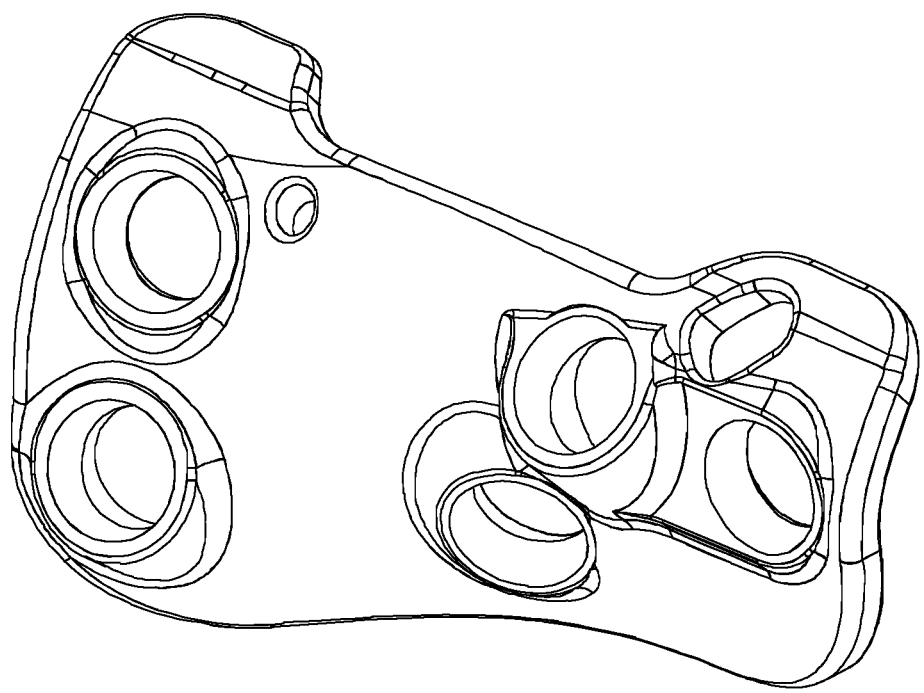
FIG. 7 is a top perspective view of another resection plate, in accordance with an aspect of the present invention.
Figure 8:
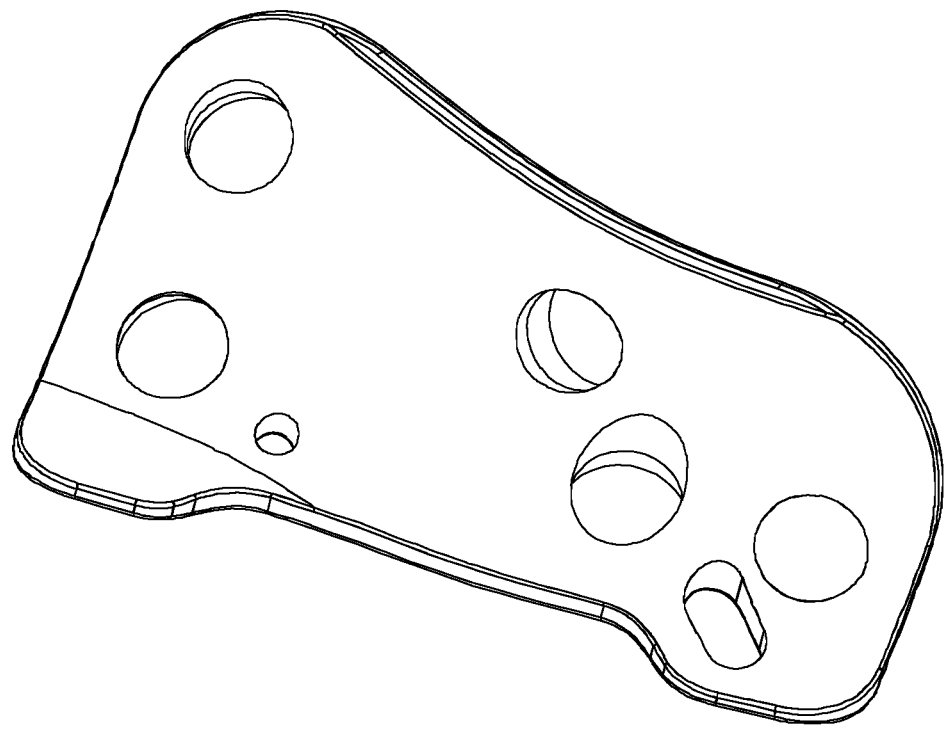
FIG. 8 is a bottom perspective view of the resection plate of FIG. 7, in accordance with an aspect of the present invention.
Figure 9:
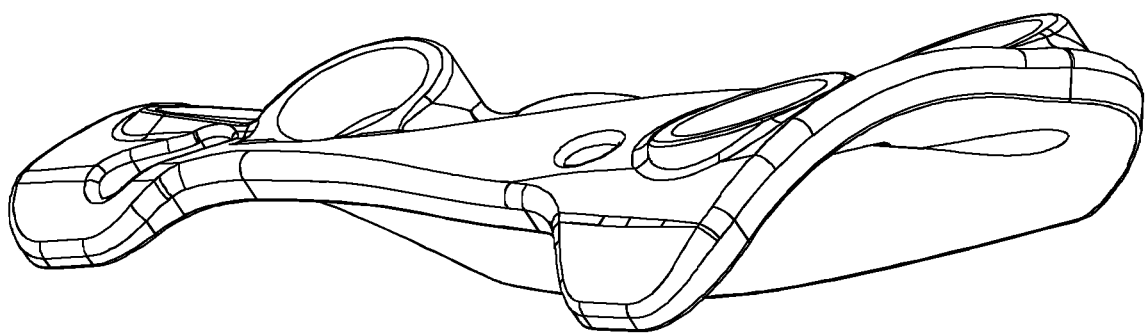
FIG. 9 is a side perspective view of the resection plate of FIG. 7, in accordance with an aspect of the present invention.

Referring to the drawings, wherein like reference numerals are used to indicate like or analogous components throughout the several views, and with particular reference to FIGS. 1-9, there is illustrated alternative embodiments of resection plates. A resection plate 100 is shown in FIGS. 1 and 2. An alternative resection plate 200 is depicted in FIGS. 3 and 4. Referring now to FIGS. 5 and 6, yet another resection plate 300 is shown. FIGS. 7-9 show another alternative resection plate 400.

The plates of FIGS. 1-9, may be used after exposing the bone site. The plates are tethered to the bone using either bone screws or temporary wires or threaded pins. One edge of the plate is used to guide a saw blade to create an osteotomy. A curved section of each plate 100, 200, 300, and 400 will generate a crescentic osteotomy. After the blade is removed, the head of the metatarsal is shifted laterally by rotation. The rotation may be, for example, in two planes. The plate 100, 200, 300, and 400 is then in full contact with the bone, having two general shapes, a proximal contact region and a distal contact region. The angle to correct the bunion deformity is, for example, typically about 13 degrees.

The plates 100, 200, 300, and 400 of FIGS. 1-9 offer several advantages. The plates 100, 200, 300, and 400 keep control of both bone segments during the operation. The plates 100, 200, 300, and 400 also provide a cutting guide integral to the plate to give a truer cut. The cut is oriented to allow the bone movement to be aligned with the desired reduction, and doesn't mal-align the bones as can be the case with free hand cutting techniques. In addition, the bones do not push off from the plate 100, 200, 300, and 400 when screws are introduced resulting in mal-alignment. The more consistent alignment created by the plates 100, 200, 300, and 400 of FIGS. 1-9 provides a better chance for a solid and expedient fusion.

The plates 100, 200, 300, and 400 also create an angular bone movement of the distal fragment during use. The incorporation of a crescent cutting guide embedded into a bone plate may also be used in other osteotomies requiring repositioning.

Additional disclosure of the embodiments of FIGS. 1-9, as disclosed above, is provided in Exhibit A which is attached hereto and is hereby incorporated by reference in its entirety.

Figure 10:
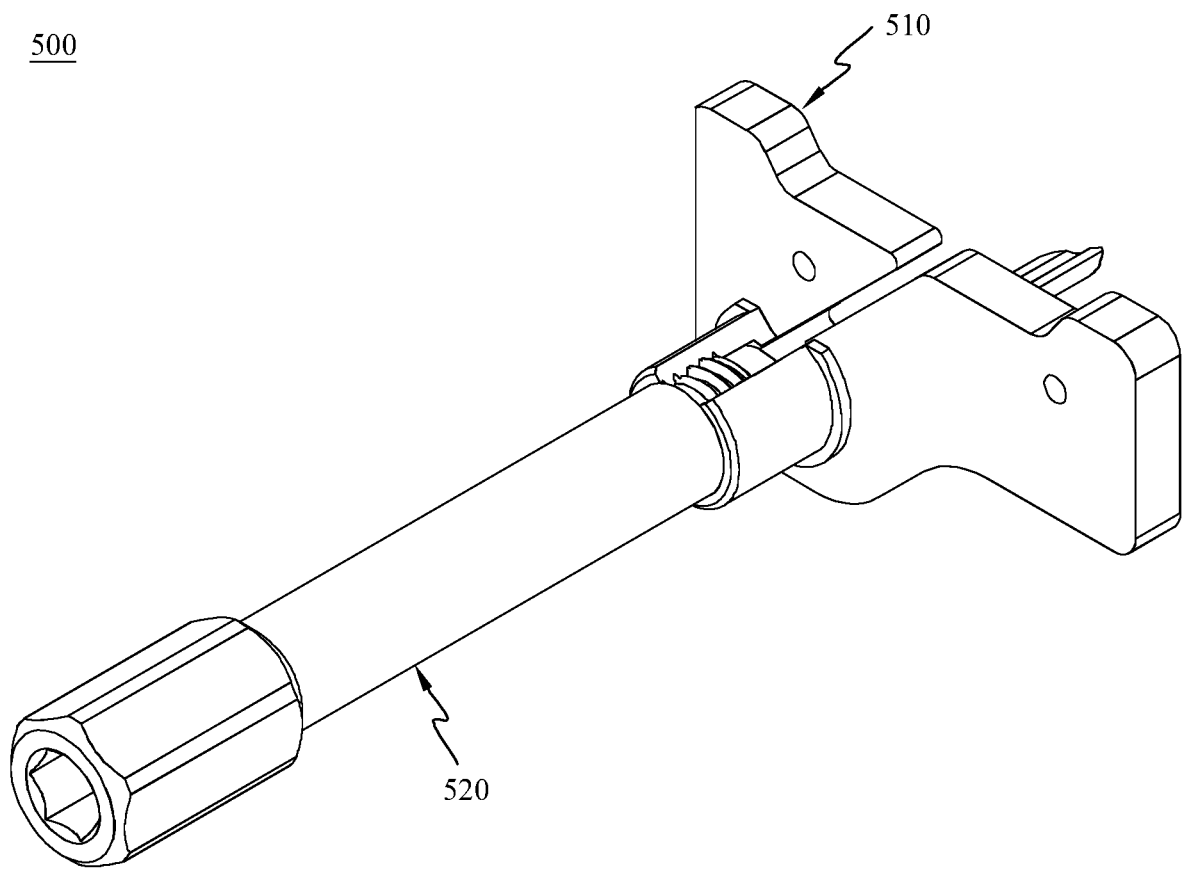
FIG. 10 is a top perspective view of a resection guide system, in accordance with an aspect of the present invention.
Figure 11:
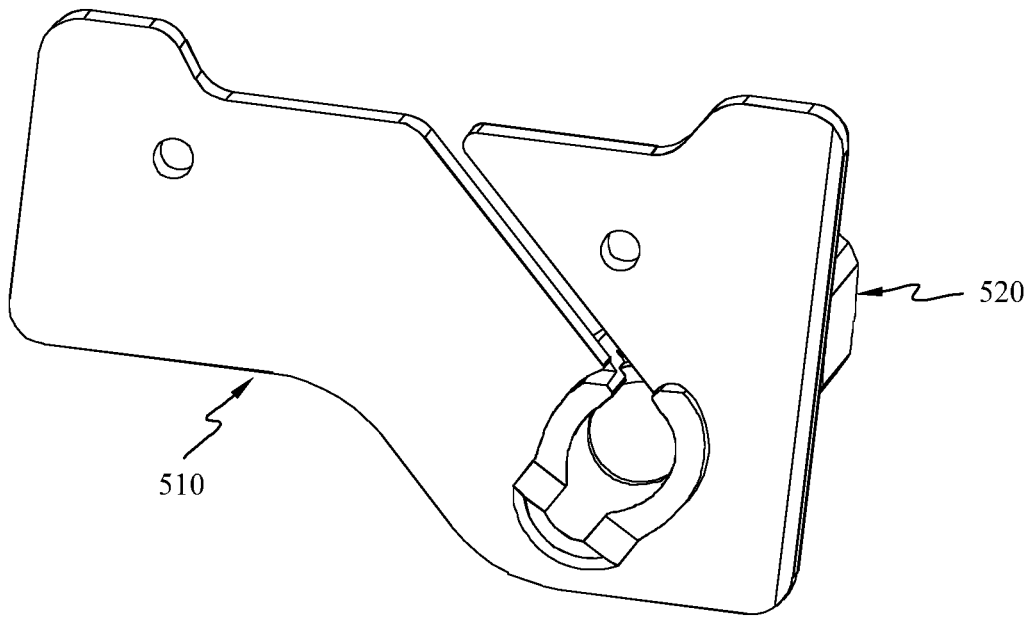
FIG. 11 is a bottom perspective view of the resection guide system of FIG. 10, in accordance with an aspect of the present invention.
Figure 12:
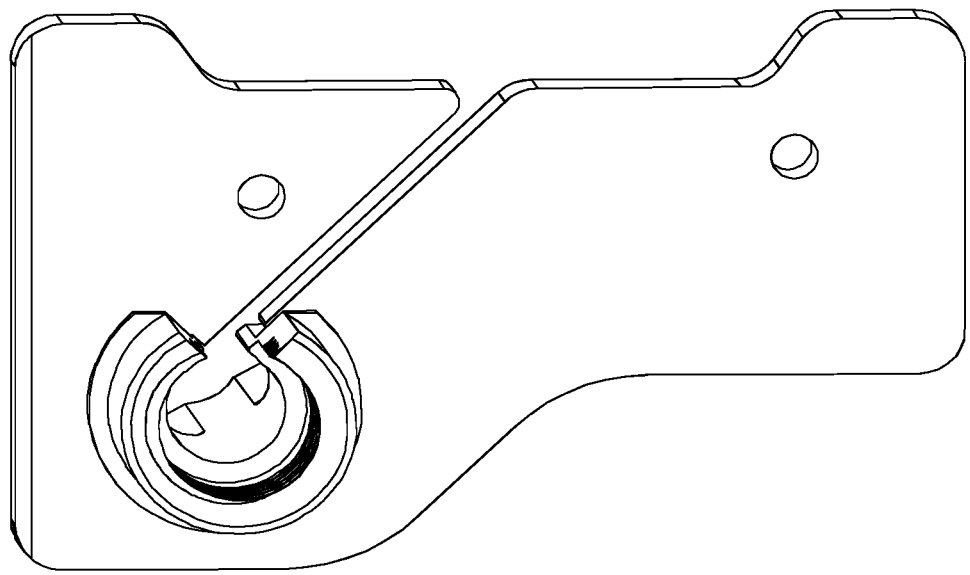
FIG. 12 is a front view of the resection guide of the resection guide system of FIG. 10, in accordance with an aspect of the present invention.
Figure 13:
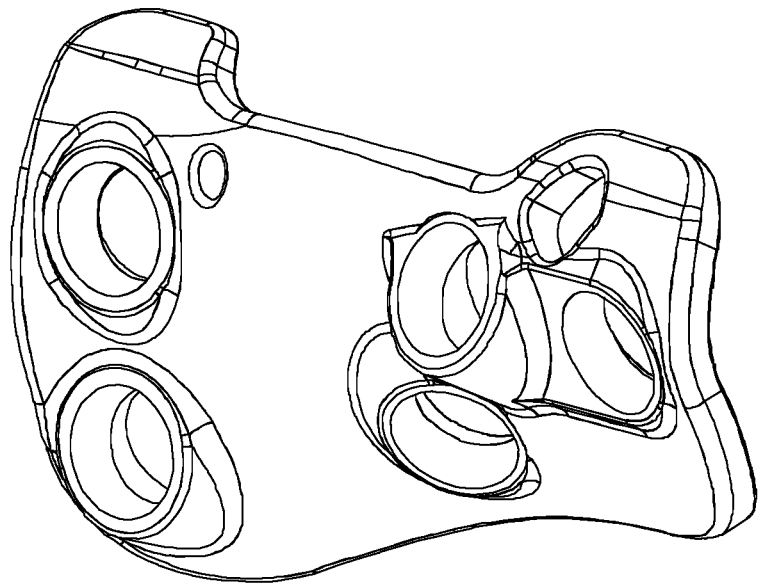
FIG. 13 is a top perspective view of a resection plate, in accordance with an aspect of the present invention.
Figure 14:
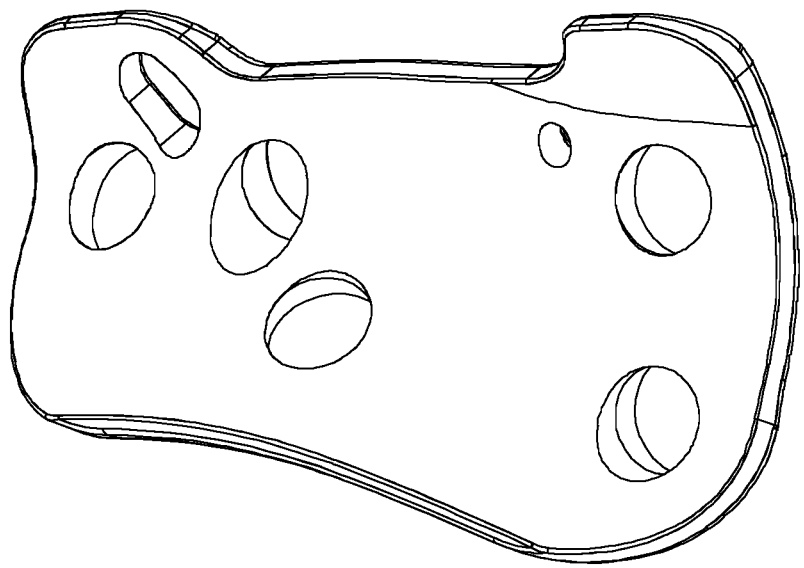
FIG. 14 is a bottom perspective view of the resection plate of FIG. 13, in accordance with an aspect of the present invention.
Figure 15:
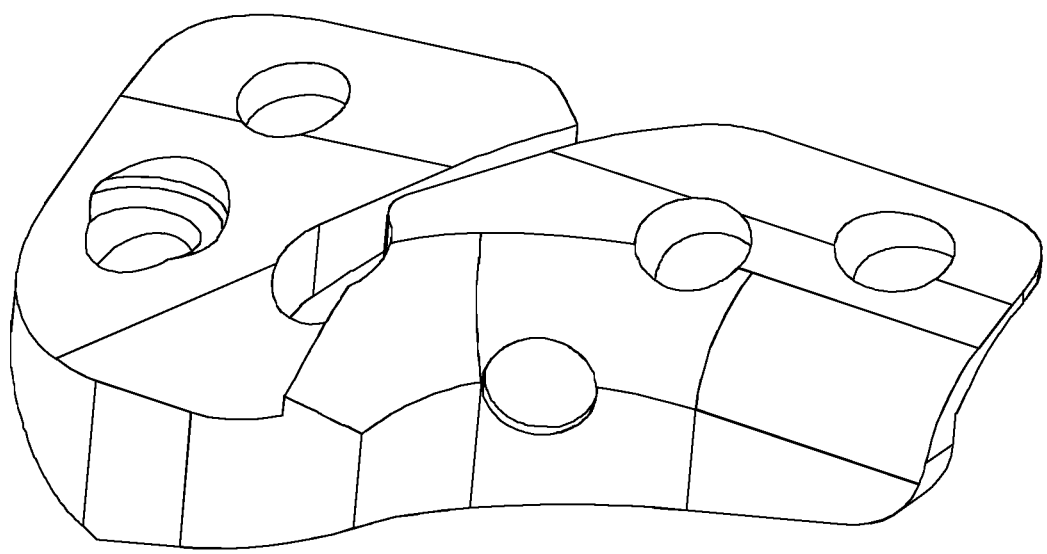
FIG. 15 is a top perspective view of another resection plate, in accordance with an aspect of the present invention.
Figure 16:
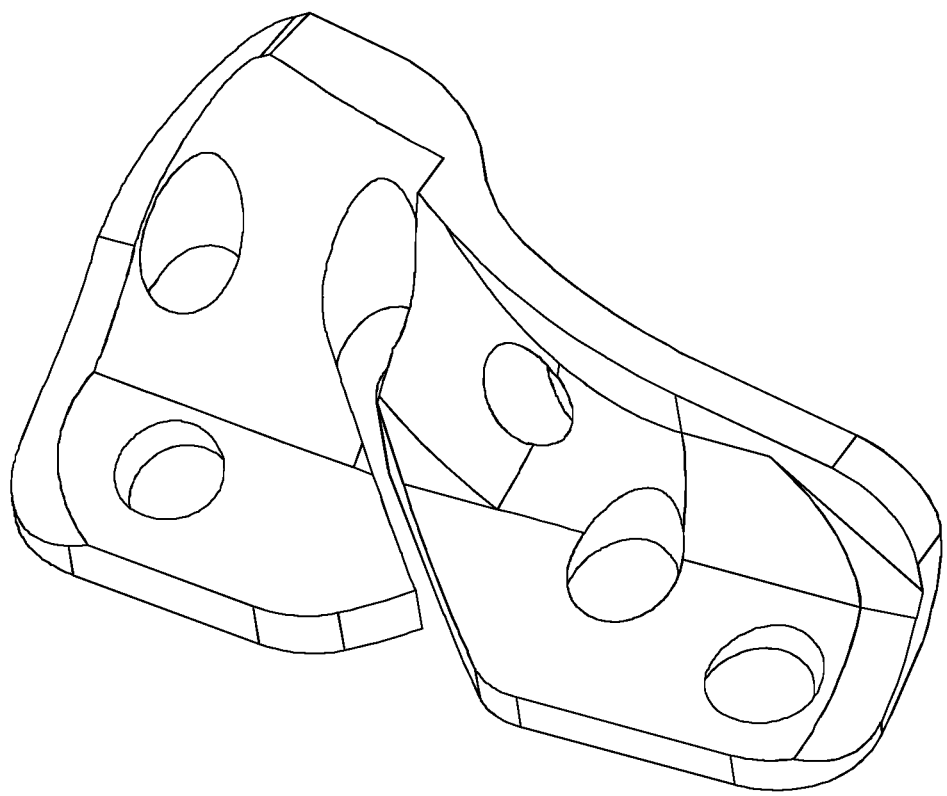
FIG. 16 is a bottom perspective view of the resection plate of FIG. 15, in accordance with an aspect of the present invention.
Figure 17:
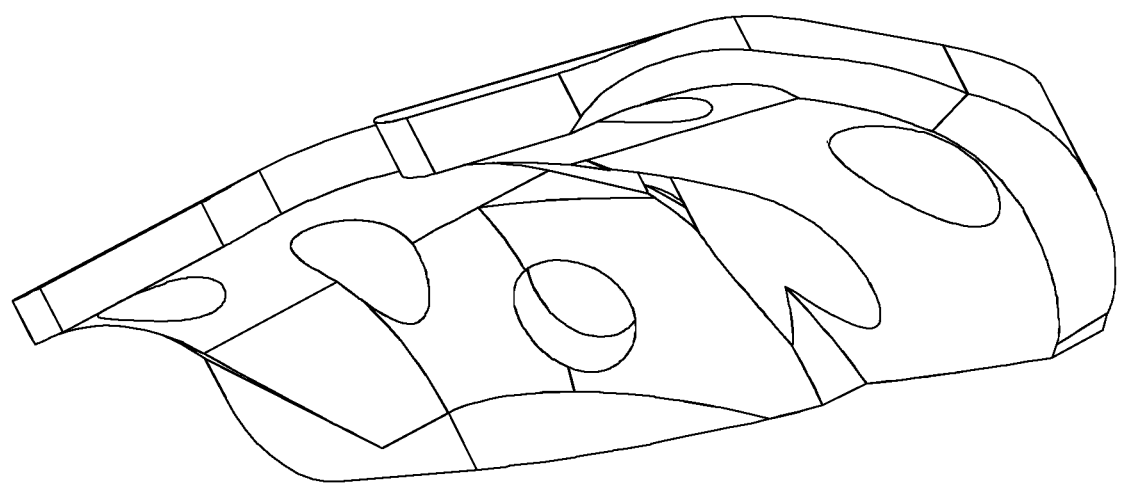
FIG. 17 is a front perspective view of the resection plate of FIG. 15, in accordance with an aspect of the present invention.
Figure 18:
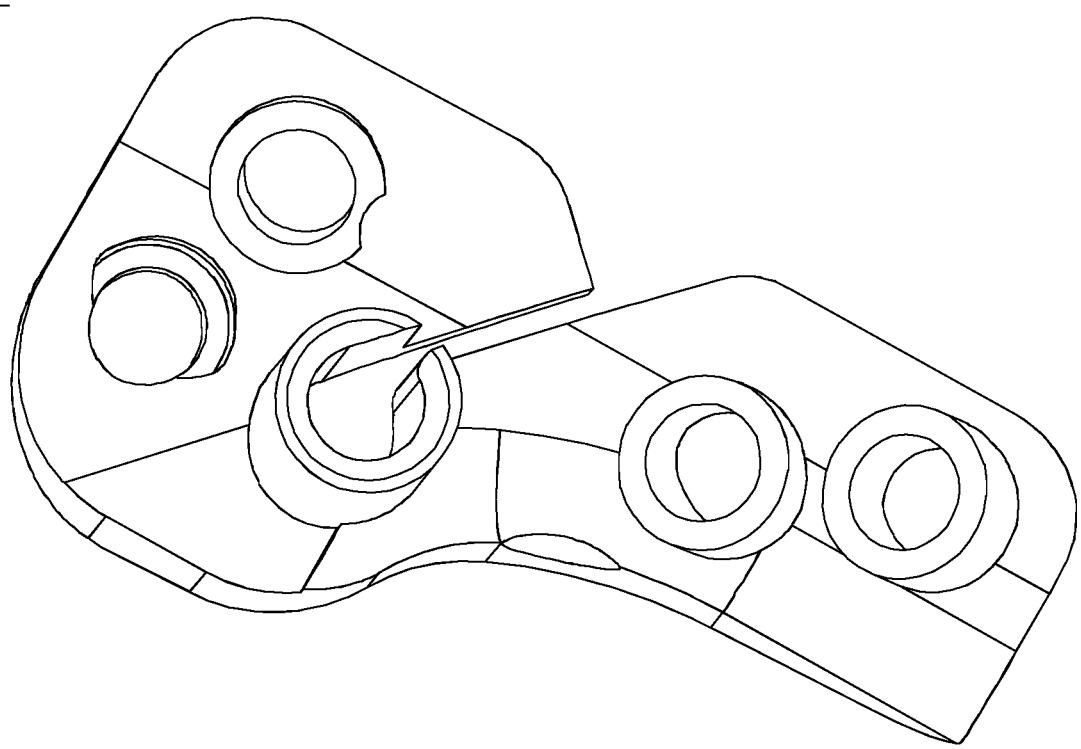
FIG. 18 is a top perspective view of a resection plate, in accordance with an aspect of the present invention.
Figure 19:
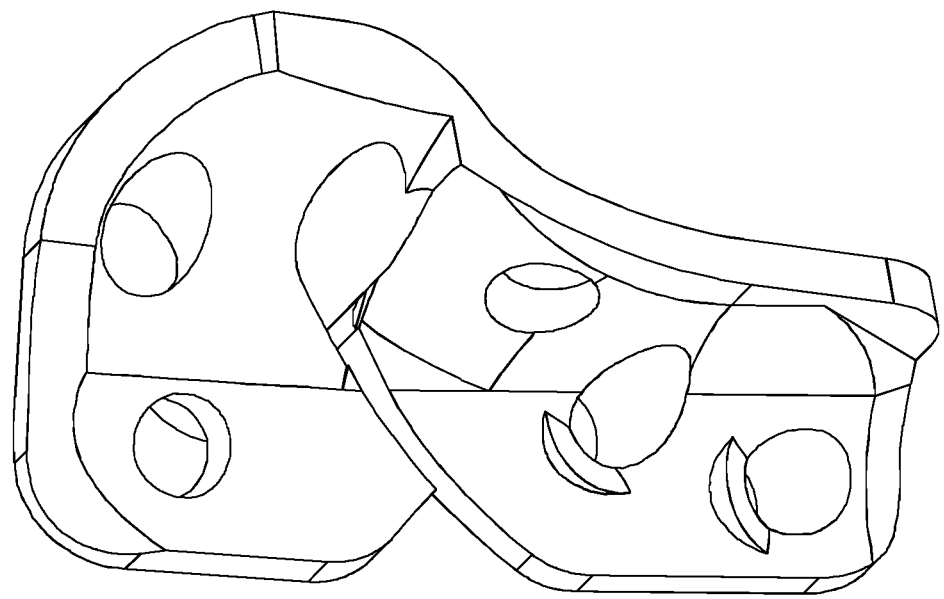
FIG. 19 is a bottom perspective view of the resection plate of FIG. 18, in accordance with an aspect of the present invention.
Figure 20:
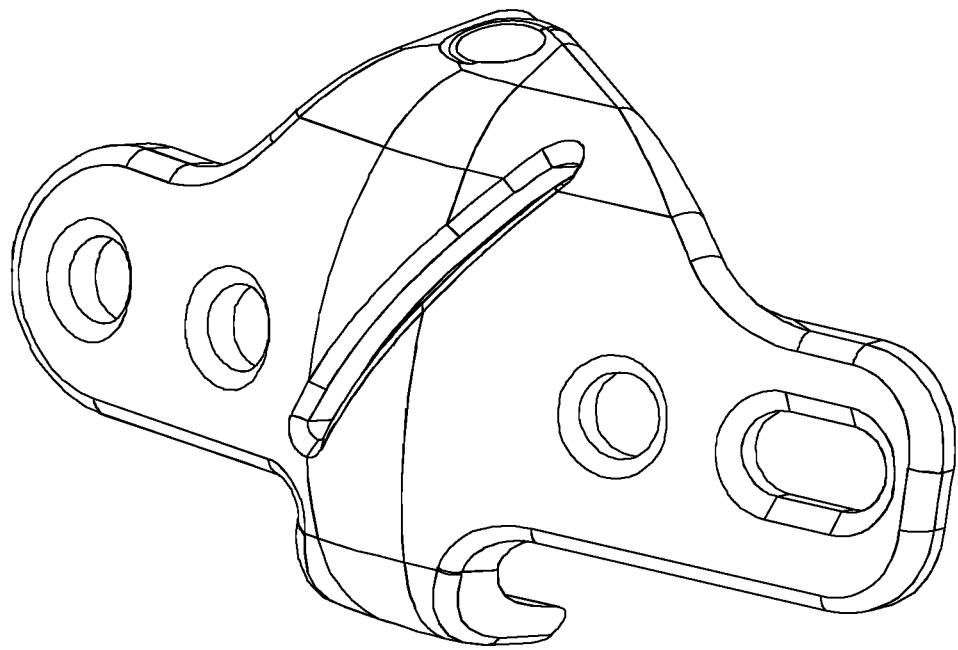
FIG. 20 is a top perspective view of yet another resection plate, in accordance with an aspect of the present invention.
Figure 21:
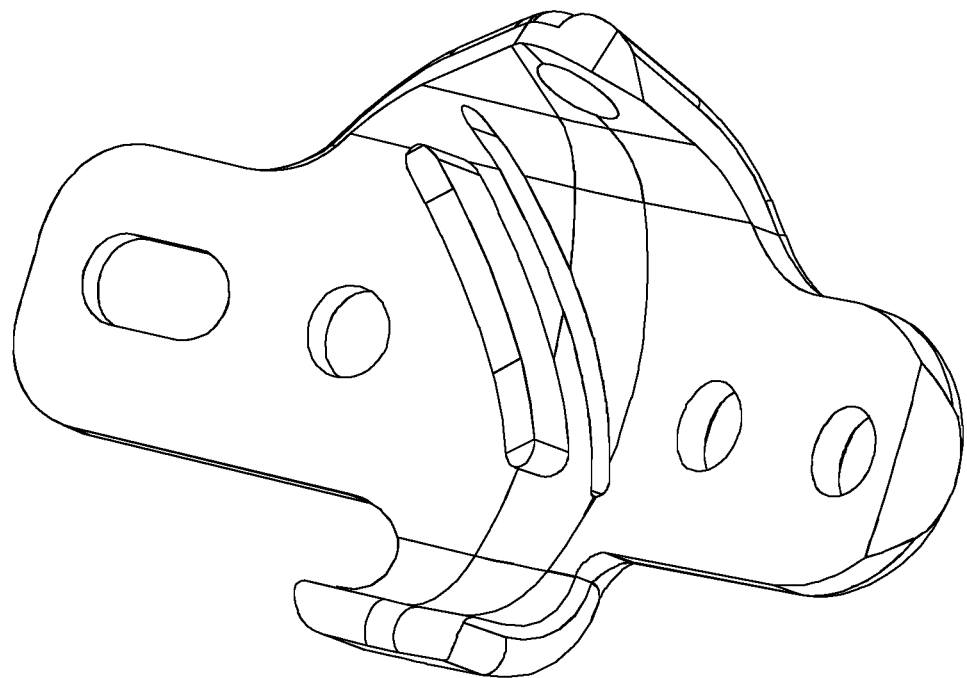
FIG. 21 is a bottom perspective view of the resection plate of FIG. 20, in accordance with an aspect of the present invention.
Figure 22:
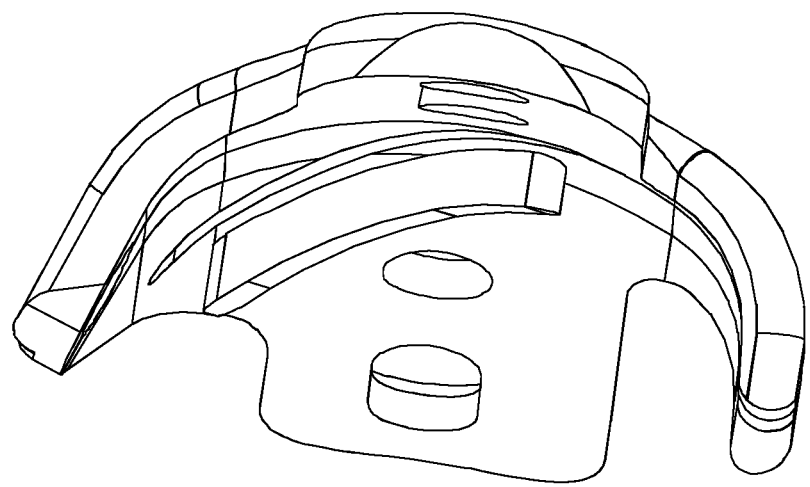
FIG. 22 is a front perspective view of the resection plate of FIG. 20, in accordance with an aspect of the present invention.
Figure 23:
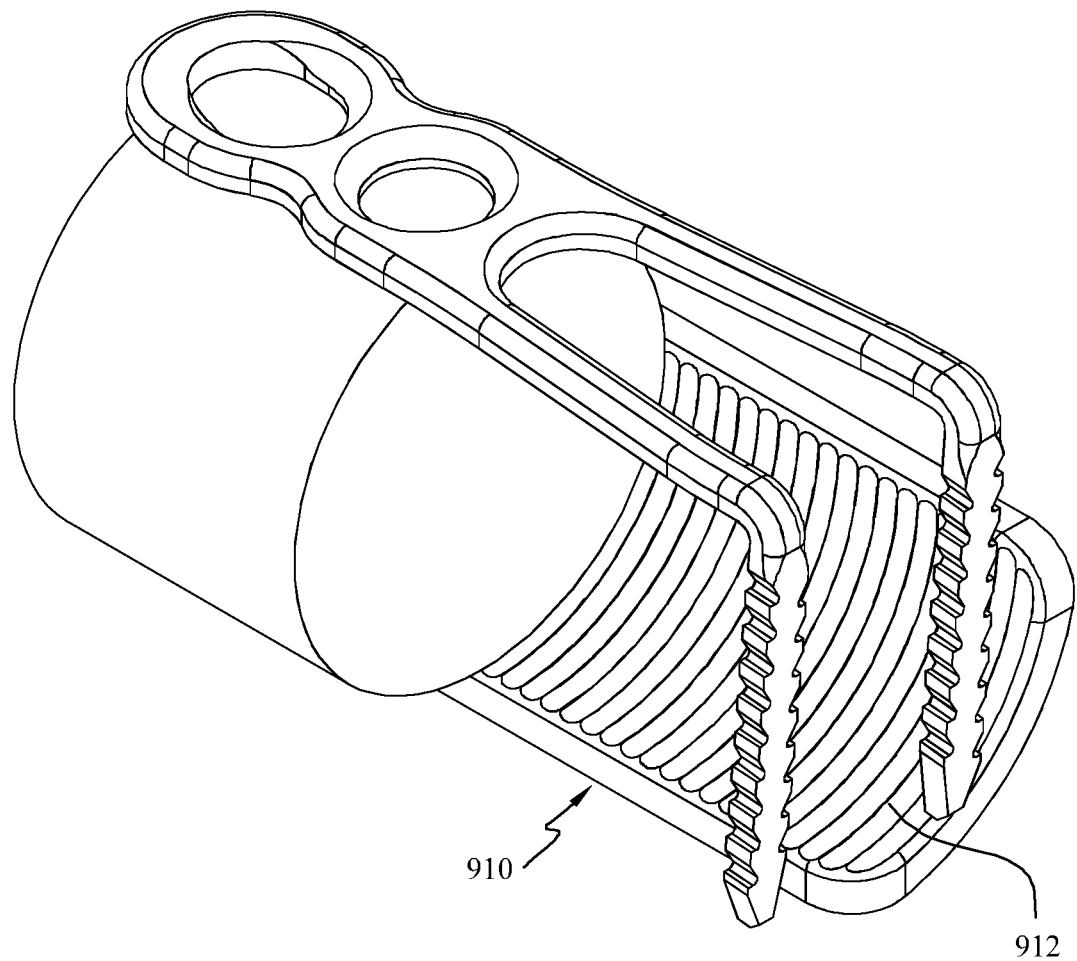
FIG. 23 is a perspective view of a sculpted plate surface for use with the resection plates, in accordance with an aspect of the present invention.
Figure 24:
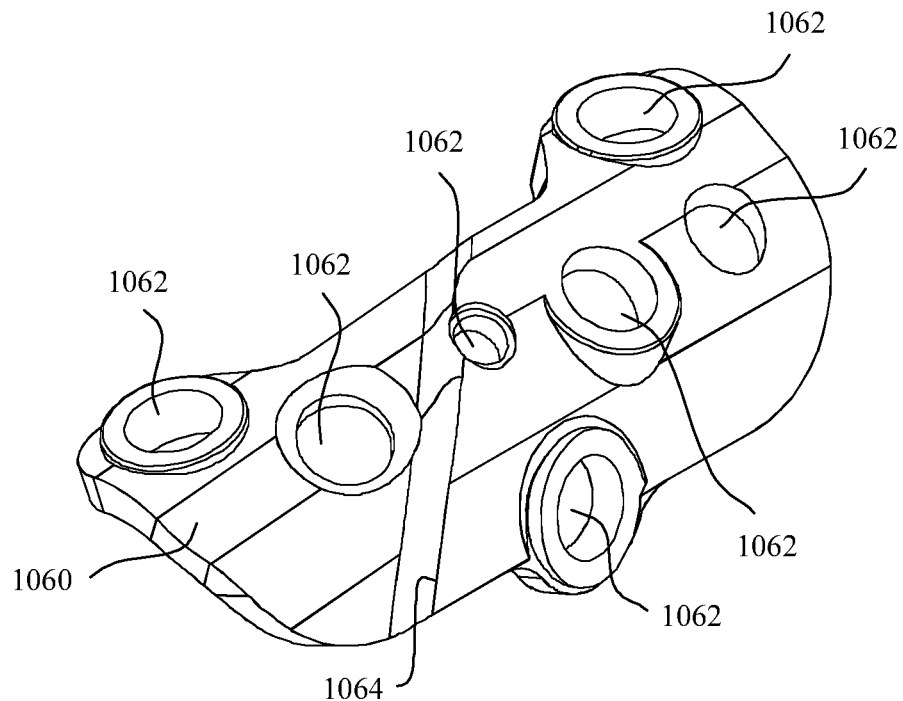
FIG. 24 is a top perspective view of another resection plate, in accordance with an aspect of the present invention.
Figure 25:
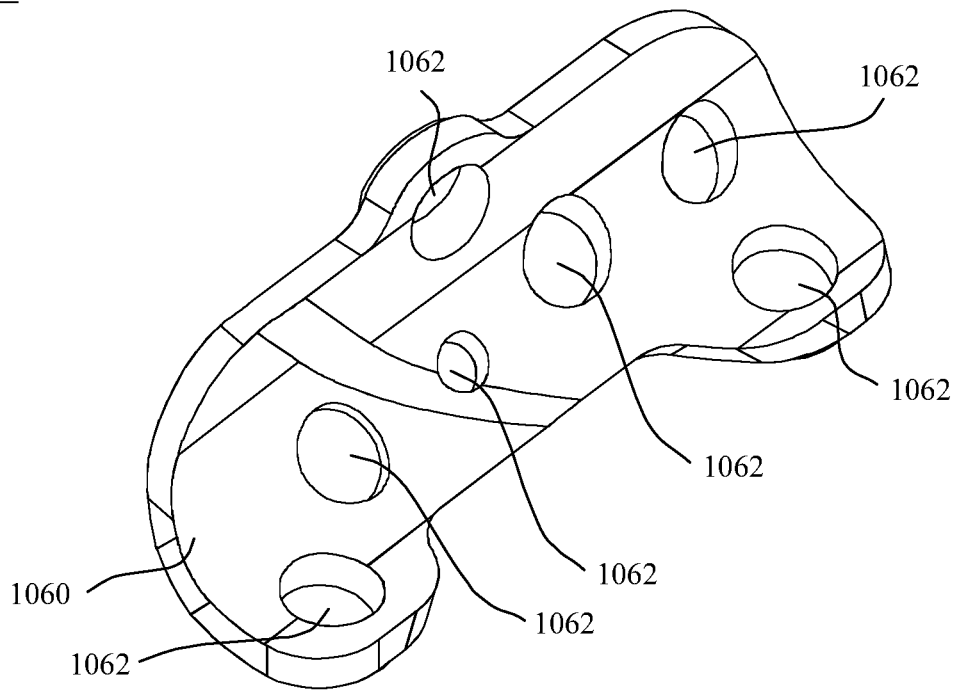
FIG. 25 is a bottom perspective view of the resection plate of FIG. 24, in accordance with an aspect of the present invention.
Figure 26:
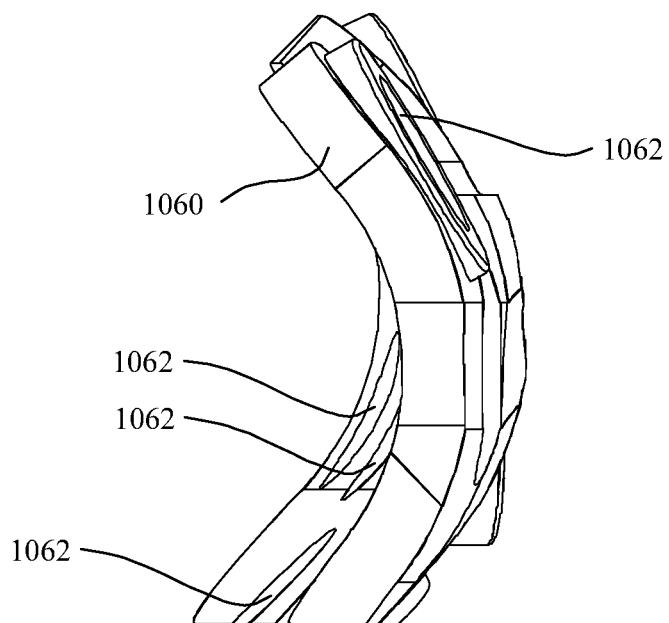
FIG. 26 is a first end view of the resection plate of FIG. 24, in accordance with an aspect of the present invention.
Figure 27:
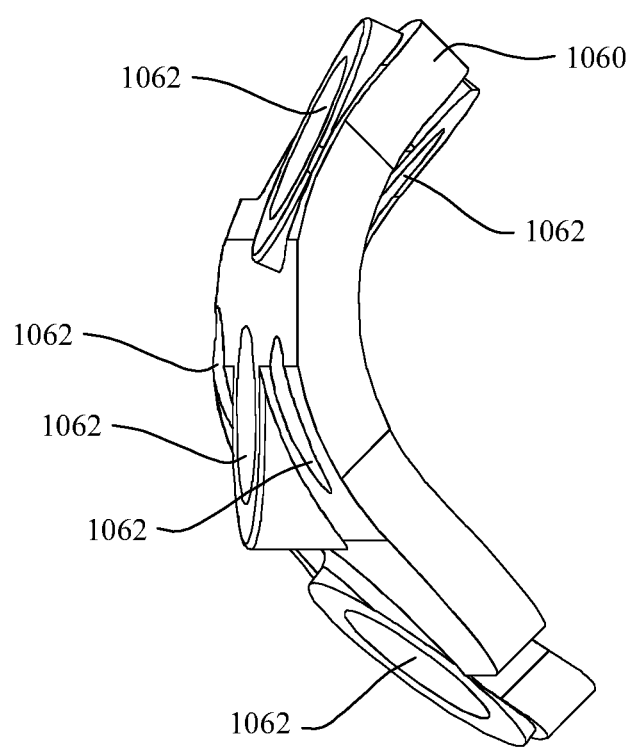
FIG. 27 is a second end view of the resection plate of FIG. 24, in accordance with an aspect of the present invention.
Figure 28:
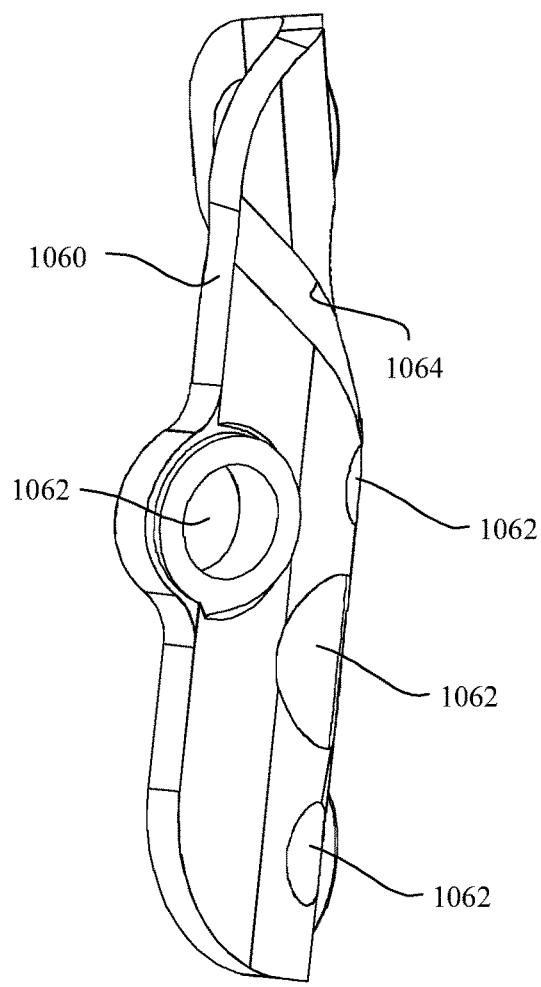
FIG. 28 is a first side view of the resection plate of FIG. 24, in accordance with an aspect of the present invention.
Figure 29:
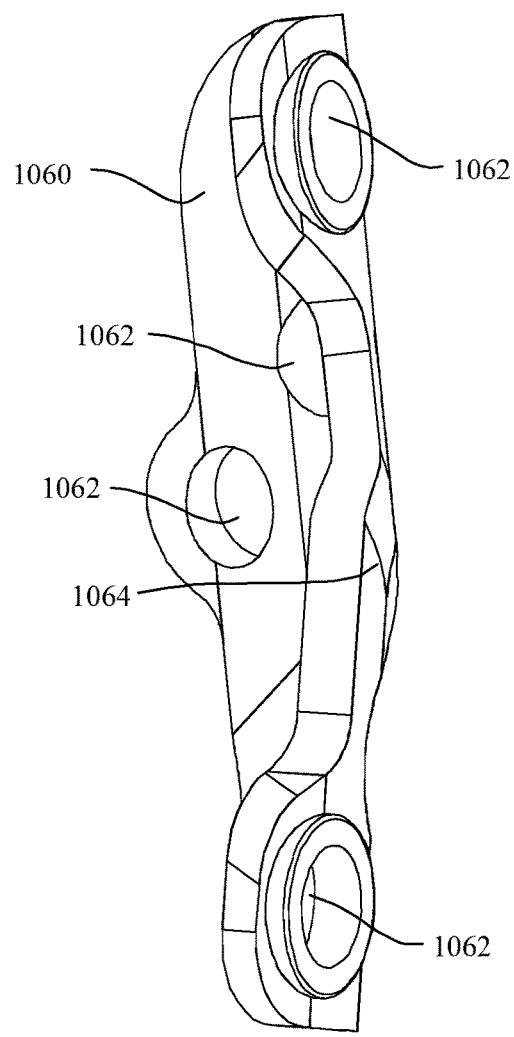
FIG. 29 is a second side view of the resection plate of FIG. 24, in accordance with an aspect of the present invention.
Figure 30:
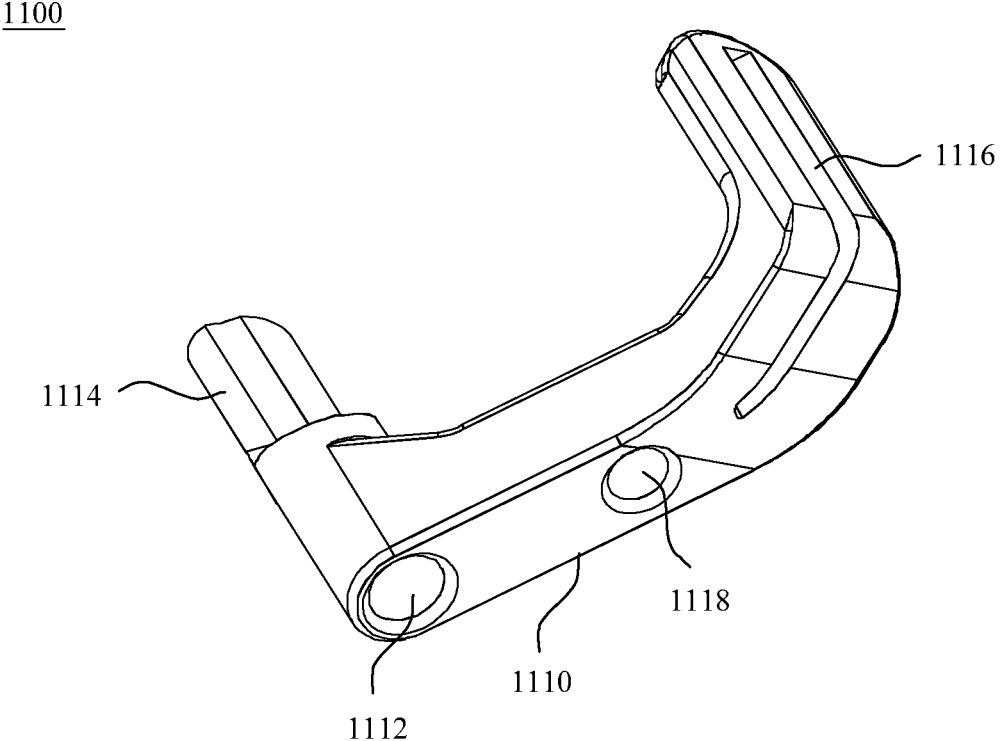
FIG. 30 is a top perspective view of a resection guide, in accordance with an aspect of the present invention.
Figure 31:
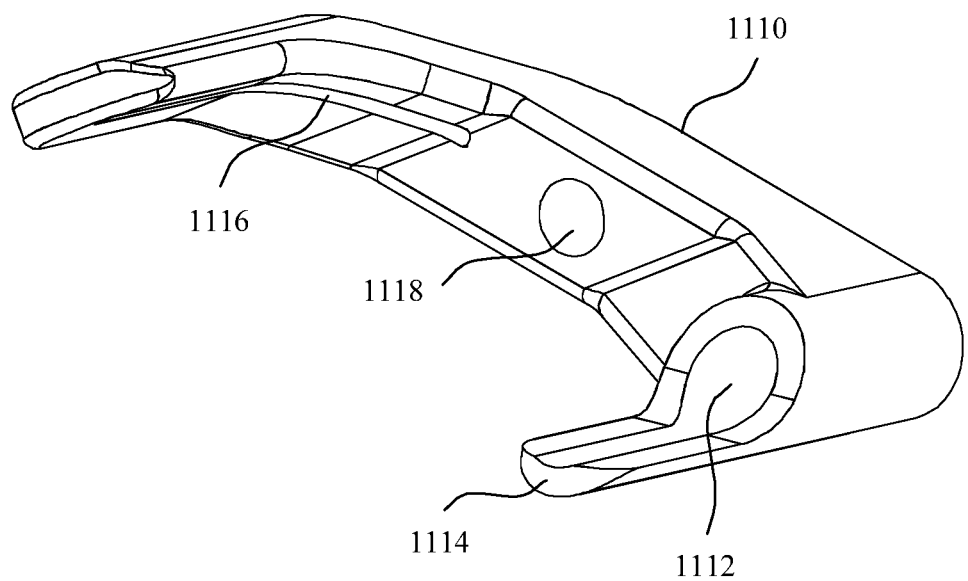
FIG. 31 is a bottom perspective view of the resection guide of FIG. 30, in accordance with an aspect of the present invention.
Figure 32:
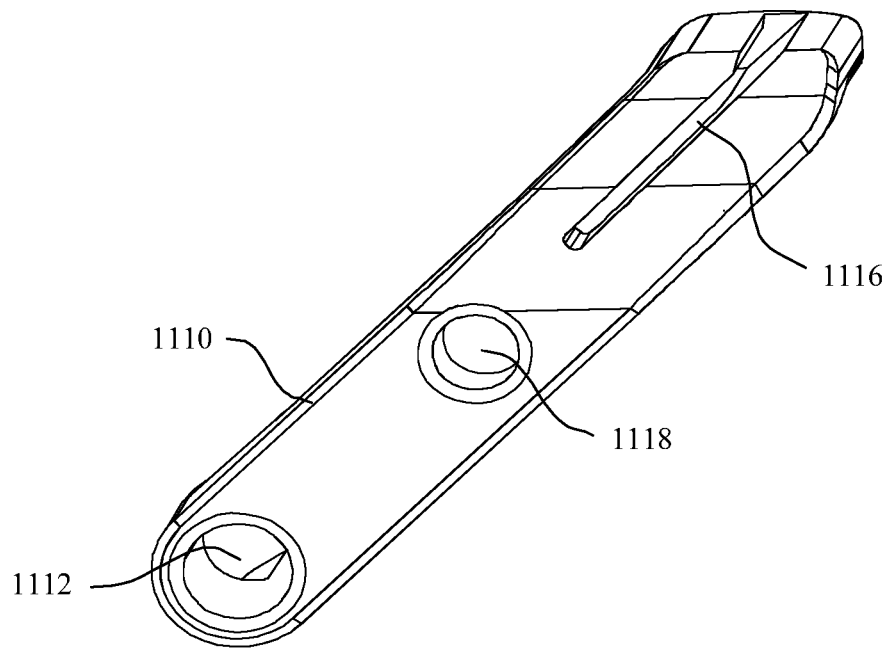
FIG. 32 is a front view of the resection guide of FIG. 30, in accordance with an aspect of the present invention.
Figure 33:
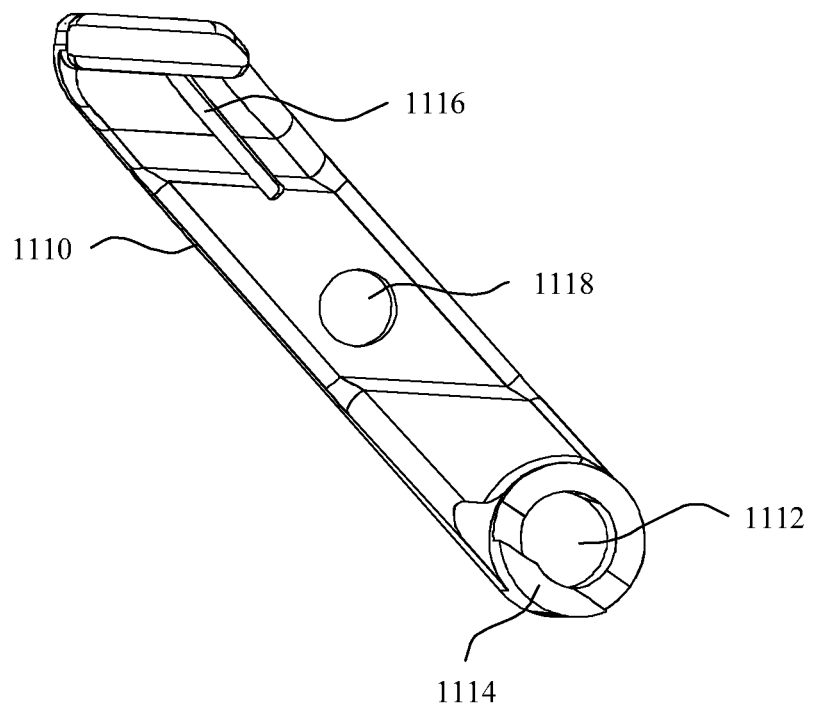
FIG. 33 is a back view of the resection guide of FIG. 30, in accordance with an aspect of the present invention.
Figure 34:
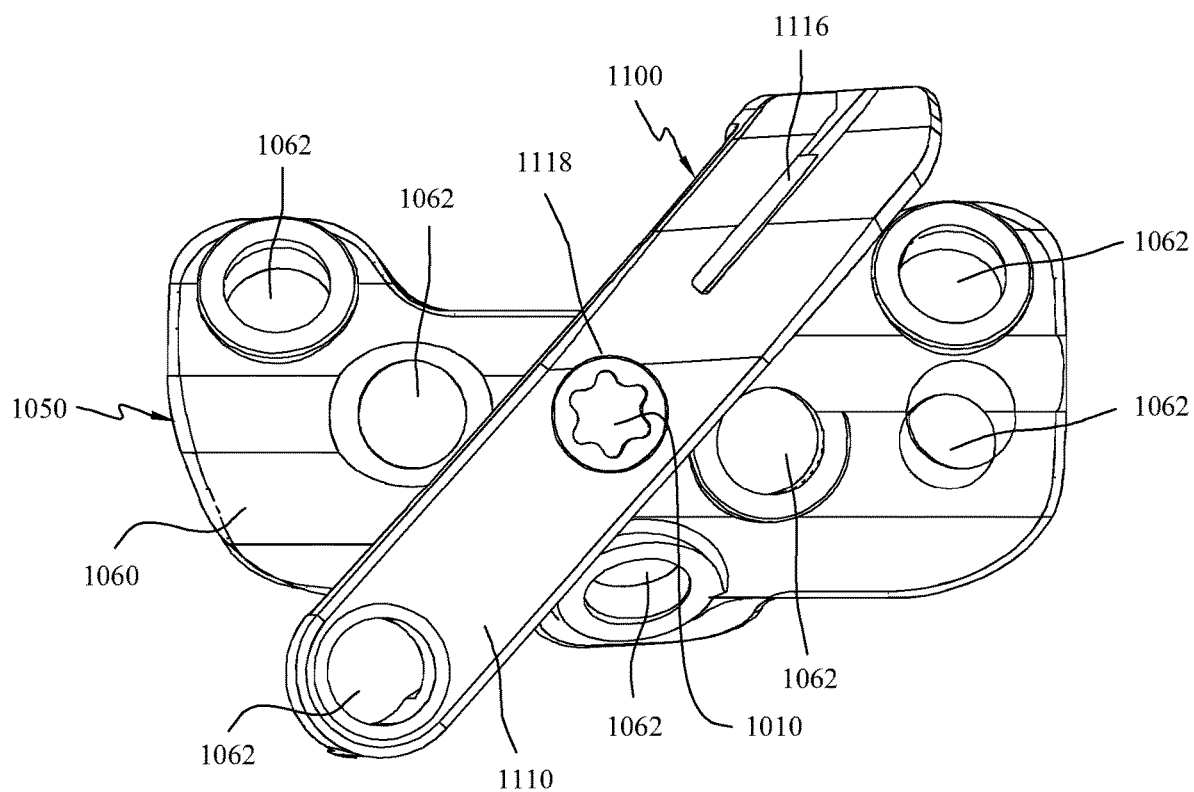
FIG. 34 is a front view of a resection system including the plate of FIG. 24 and guide of FIG. 30, in accordance with an aspect of the present invention.
Figure 35:
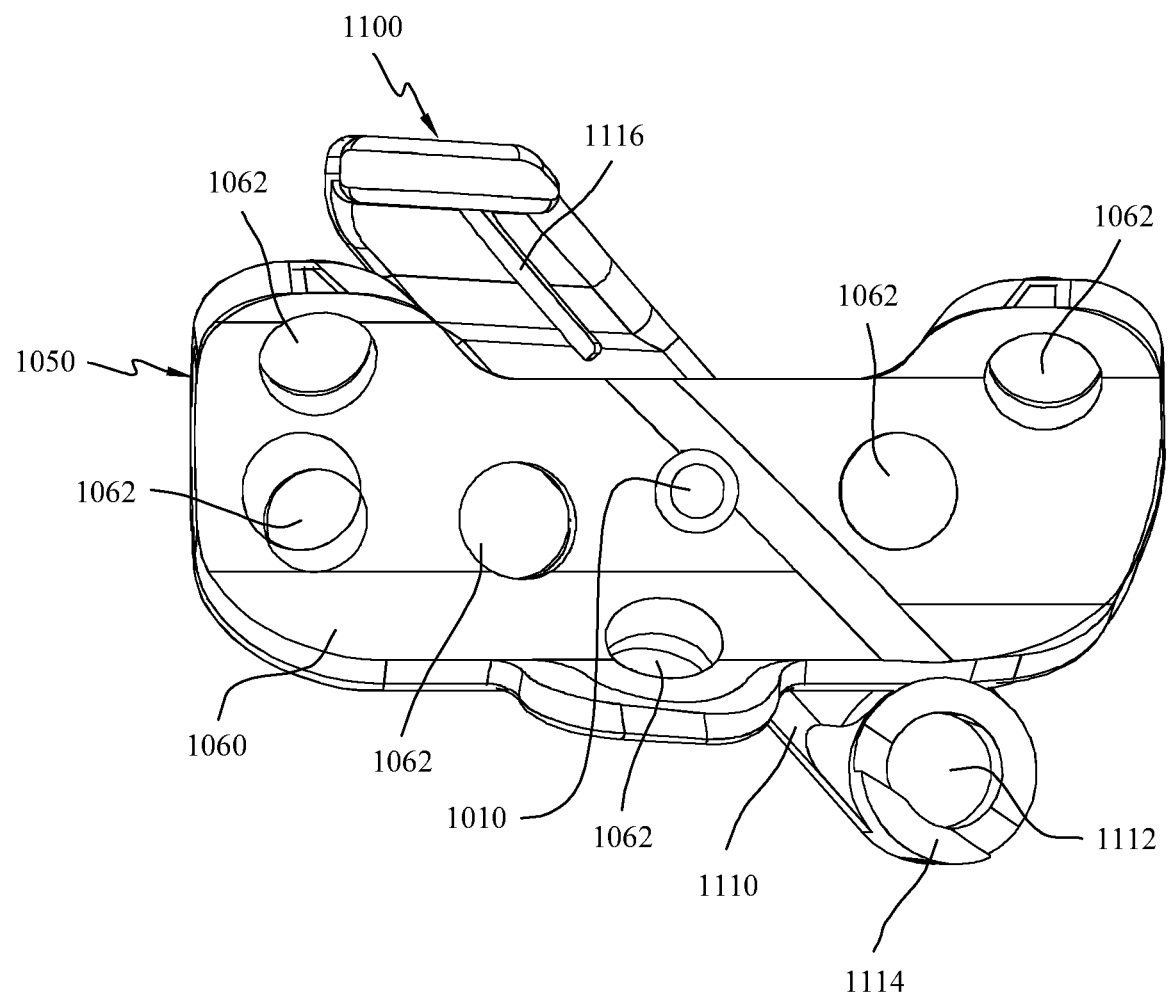
FIG. 35 is a back view of the resection system of FIG. 34, in accordance with an aspect of the present invention.
Figure 36:
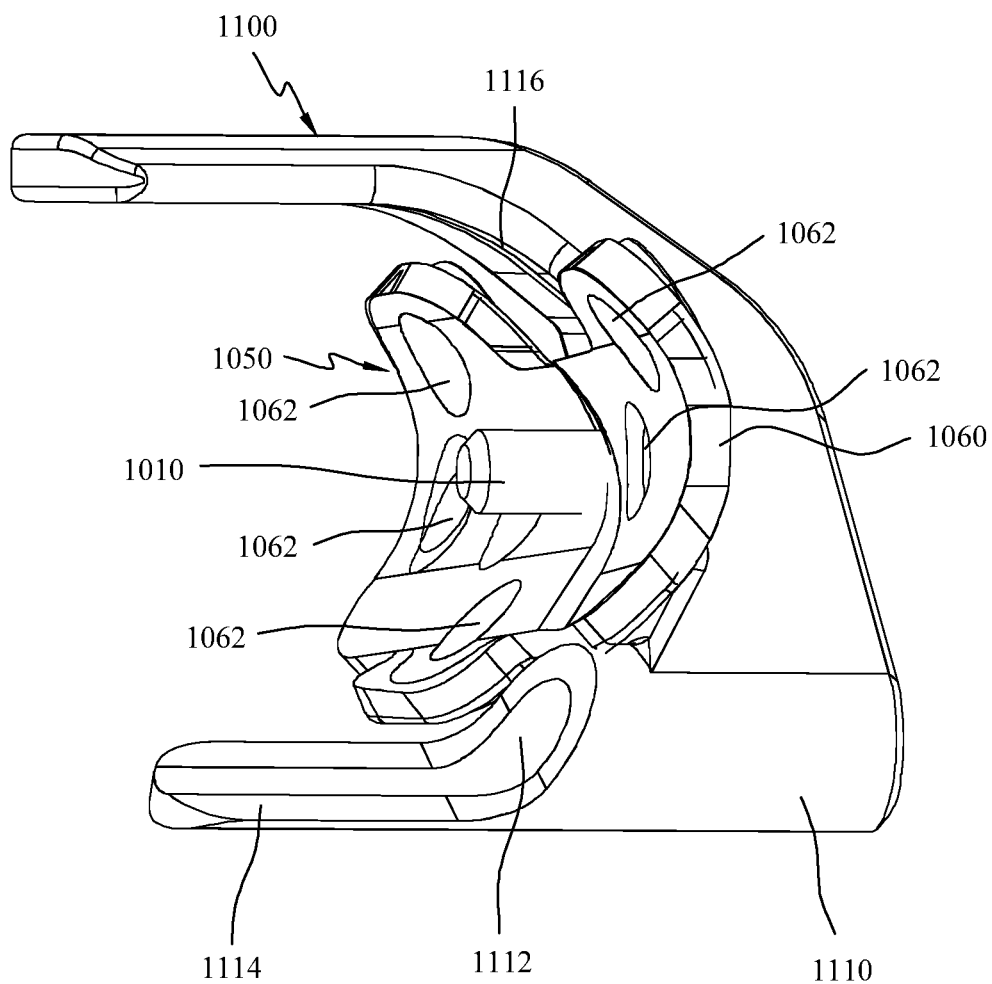
FIG. 36 is a first end view of the resection system of FIG. 34, in accordance with an aspect of the present invention.
Figure 37:
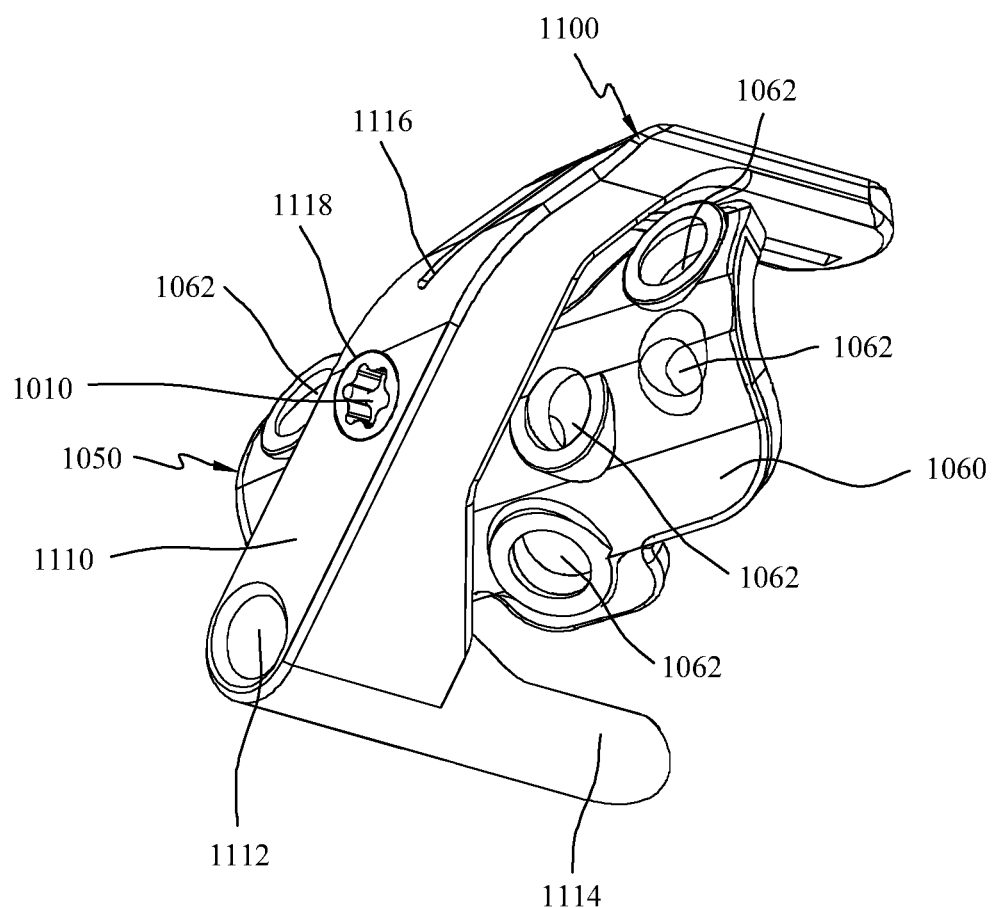
FIG. 37 is a top perspective view of the resection system of FIG. 34, in accordance with an aspect of the present invention.
Figure 38:
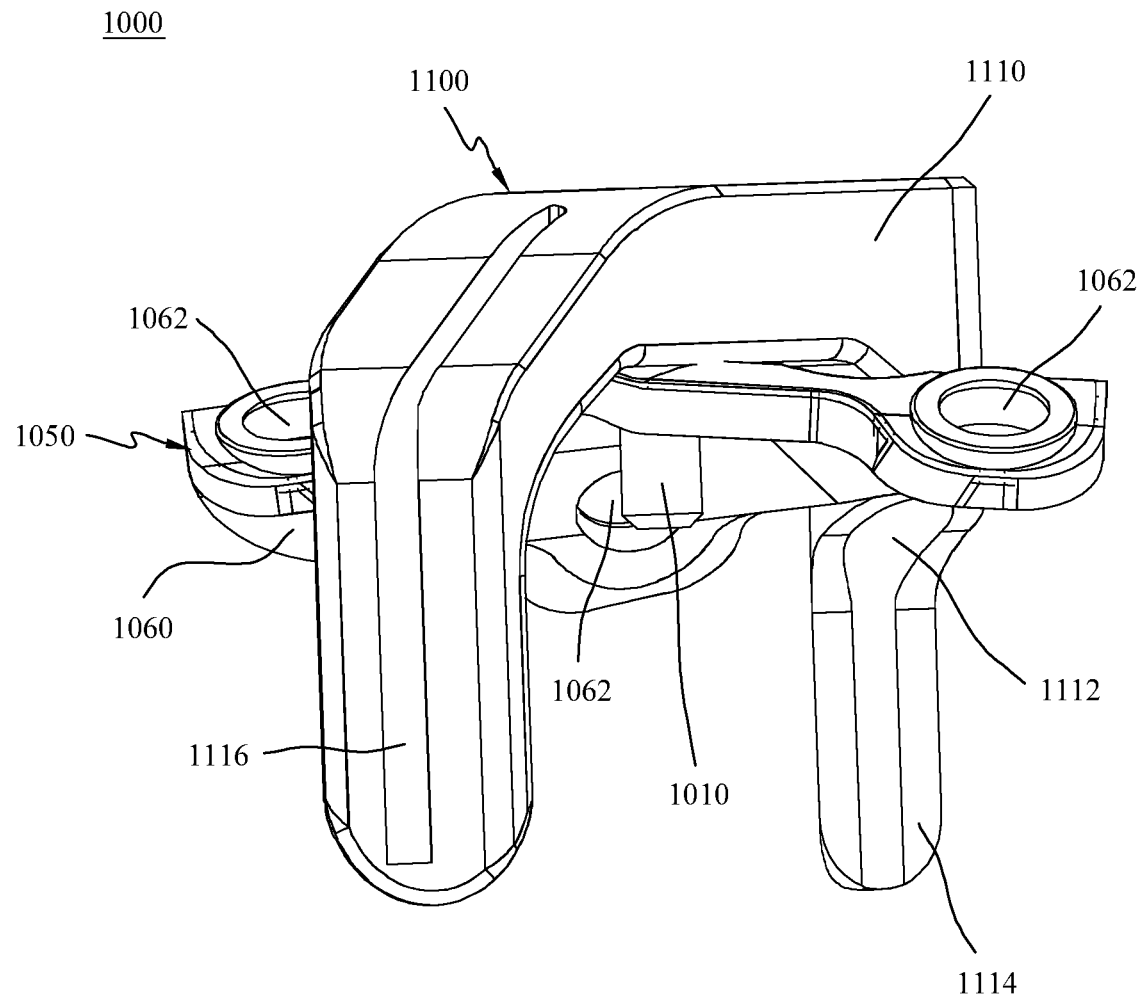
FIG. 38 is a top view of the resection system of FIG. 34, in accordance with an aspect of the present invention.

Referring now to FIGS. 10-23, various alternative embodiments of proximal bunion resection guides and plates are shown. FIGS. 10-12 show a resection guide system 500 including a cutting guide 510 and a drilling guide 520. The resection guide system 500 of FIGS. 10-12 has a corresponding resection plate 550 which is shown in FIGS. 13 and 14. Another resection plate 600 is shown in FIGS. 15-17. Another alternative resection plate 700 is shown in FIGS. 18 and 19. Still another alternative resection plate 800 is depicted in FIGS. 20-22.

The plates 550, 600, 700, and 800 of FIGS. 15-22, may provide a guide for cutting the patient's bone at an angle to the bone axis as well as a means to drill a hole to allow for shortening of the length. In addition, the drilled hole may provide for an interlocking bone geometry to support a load by direct contact. The plates 550, 600, 700, and 800 of FIGS. 15-22 may be secured to the patient's bones by guide screws on both sides of the fusion site and at least one screw crossing the osteotomy to provide for a stable osteotomy Additional disclosure of the embodiments of FIGS. 10-25 as disclosed above is provided in Exhibit B which is attached hereto and is hereby incorporated by reference in its entirety.

Referring now to FIGS. 26-38, a resection system 1000 including a plate 1050 and resection guide 1100 is shown in FIGS. 34-38. The plate 1050 is shown in greater detail in FIGS. 24-29 and the resection guide 1100 is shown in greater detail in FIGS. 30-33. The plate 1050 includes a body 1060 including a plurality of openings 1062. The plurality of openings 1062 may be sized and shaped to receive, for example, pins, screws, locking mechanisms, and the like to temporarily and/or permanently secure the plate 1050 to the bone and to temporarily secure the resection guide 1100 to the plate 1050. The openings 1062 may be, for example, tapered threaded locking holes which may receive screws with dual lead tapered locking threads on the heads. The plate 1050 may also include an alignment marking 1064 for aligning with the cut surface of the distal portion of the metatarsal after resection.

As shown in FIGS. 30-38, the resection guide 1100 includes a body 1110 with a first opening 1112 which extends into a flange 1114, a slot 1116 on a side opposite the first opening 1112, and an attachment opening 1118 positioned between the first opening 1112 and the slot 1116. The first opening 1112 and flange 1114 are design to receive a drill to drill a hole into the patient's bone without damaging the surrounding tissue. The slot 1116 is designed to receive a blade to cut the patient's bone. The position of the first opening 1112 and the slot 1116 are such that the cut performed using the slot 1116 will intersect the hole drilled using the first opening 1112 to fully cut the patient's bone.

As shown in FIGS. 34-38, the resection guide 1100 is secured to the plate 1050 using an opening 1062 near the center of the plate 1050. The resection guide 1100 may be secured to the plate 1050 using a securement mechanism 1010. The securement mechanism 1010 may be, for example, a biased spring, locking element, mouse trap spring, external knob, screw, or the like, which will allow for attachment and removal of the resection guide 1100 to the plate 1050. When the resection guide 1100 is secured to the plate 1050, the resection guide 1100 is positioned at an angle with respect to the longitudinal axis of the plate 1050.

Many contoured bone plates, such as plate 1050, are shaped to restore damaged bones to anatomic shape. They are designed by looking at average bone shapes and sizes and making a plate or series of plates that mimic the healthy bone shape. They are held in place with a series of screws that may include a crossing screw. Locking and non-locking screws are selectively employed.

The bone plate 1050 of FIGS. 24-29 and 34-38 may be contoured to provide specific angulation or re-angulation after bone alteration, i.e. an osteotomy. The plate 1050 provides the ability to create an angular change to the axis of the bone by forming the angle into the bone contour surfaces, which differ from one end to the other. The bone plate 1050 may form an interlocking osteotomy that is shorter than a standard osteotomy. The bone plate 1050 may be inserted using minimally invasive procedures. The bone plate 1050 may also include protruding ridges or other shapes to provide additional rigidity of the bone construct while the plate 1050 is snugged down to bone with screws or fasteners (not shown). A large radius tool can be used to create these features which are generally perpendicular to the load axis of the bone. The plate 1050 may also accommodate an osteotomy cut after angular reduction with contact of the perioisteum. Each of the plates disclosed herein may be secured to the bone with speed nuts.

The osteotomies performed with the plate 1050 of FIGS. 24-38 may provide angular correction of the first metatarsal the degree of angulation may be, for example, between approximately 2° and 20°, and more specifically approximately 5°, 7.5°, 10°, or 12.5° or 15° . The plates and guides of FIGS. 24-38 may provide a guide for cutting the patient's bone at an angle to the bone axis as well as a means to drill a hole to allow for shortening of the length. In addition, the drilled hole may provide for an interlocking bone geometry to support a load by direct contact. The plate 1050 may be secured to the patient's bones by guide screws on both sides of the fusion site and at least one screw crossing the osteotomy to provide for a stable osteotomy.

The plate 1050, as well as additional plates disclosed herein which include the cutting and/or drill guide in or attachable to the plate, provide for a contiguous location of the plate using temporary threaded wires or other temporary fixation mechanisms. The temporary threaded wires or temporary fixation mechanisms maintain control of both bone fragments during the duration of the procedure. Speed nuts provide for hands free cut guide retention to the bone and hands free plate retention to the bone. The plate 1050 and guide 1100 allow for a means to centralize the drill for a locking screw, both locking and non-locking screw options, and the ability to lock the position of the screw axis to the plate. The lock screw may have a pitch equal to that of the bone thread.

The resection system 1000 also provides for a repeatable contact location of the cut guide placement using the plantar tang or flange 1114. The resection system 1000 also provides for soft tissue protection during the osteotomy creation. The resection system 1000 may also include a means to align the cute guide which may function as a handle to manipulate the guide 1100. The resection system 1000 may also include threaded guide wires for retention of the plate 1050. Further, the resection system 1000 may have male threaded fasteners with alternating thread contact regions to allow for a rapid axial advancement until thread engagement and locking forces are needed. The guide 1100 of the resection system 1000 is an angle adjustable osteotomy guide.

A method of using the resection system 1000 may include positioning the plate 1050 on a bone and locking the plate to a proximal portion of the bone with a first screw. Next a pin may be inserted into the distal portion of the bone. The resection guide 1100 may then be attached and locked to the plate 1050 using a center opening 1062 in the plate 1050. Then a hole may be drilled into the bone through the first opening 1112. After the hole is drilled, the osteotomy may be finished by inserting a saw or blade into the slot 1116 to cut the bone at an angle. Once the cut is complete the saw or blade and guide 1100 may be removed. Next reduction occurs by pivoting and sliding the distal bone laterally. Once the desired position is reached a cross screw may be inserted across the cut to secure the proximal and distal portions together. Next the other screws may be inserted into the openings 1062 to secure the plate to the proximal and distal portions. Finally, the pin may be removed from the distal portion and the patient's incision closed.

Additional disclosure of the embodiments of FIGS. 34-38 disclosed are provided in Exhibit C which is attached hereto, is hereby incorporated by reference in its entirety.

The plates of the present application, as described in greater detail above, may include a micro or macro grooved or irregular bone contacting surface to aid in bone plate stability and fixation. The bone contacting surface 912 as shown on a plate 910 in FIG. 23 may be, for example, a series of grooves, waves, serrations, scallops, or other contoured surface structures.

Referring now to FIGS. 39-63, another resection system including a resection guide 1200 and plate 1250 is shown. The resection guide 1200 is shown in FIGS. 39-44. The resection guide 1200 includes a body 1202 with a first end 1204 and a second end 1206. The body 1202 may also include a first extension 1208 positioned away from a first side of the body 1202 and a second extension 1210 positioned away from a second side of the body 1202. The first extension 1208 may be angled towards the second end 1206 of the body. The second extension 1210 may be positioned near the first end 1204 of the body. For example, the first extension 1208 may extend in an anterior and superior direction and the second extension 1210 may extend in a posterior and inferior direction from the body 1202. The second extension 1210 may include, for example, a first section 1212 extending away from the body 1202 at an angle toward the first end 1204 and a second section 1214 extending away from the first section 1212 at a relatively perpendicular angle towards the second end 1206.

Figure 39:
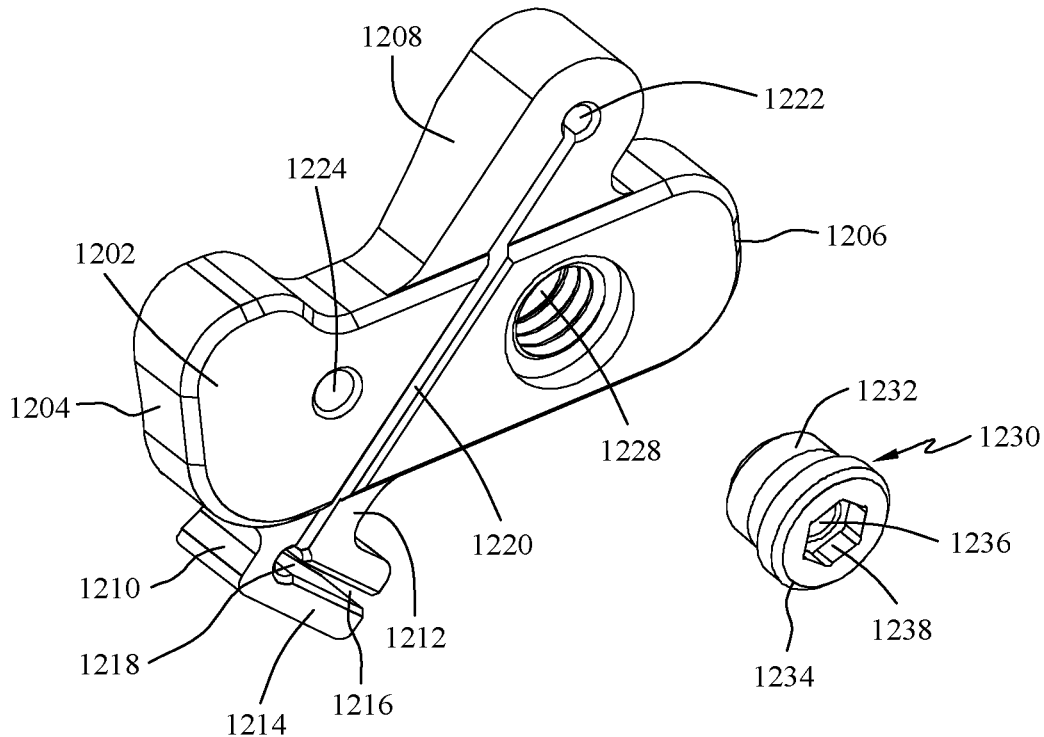
FIG. 39 is an exploded, perspective view of a resection guide, in accordance with an aspect of the present invention.
Figure 40:
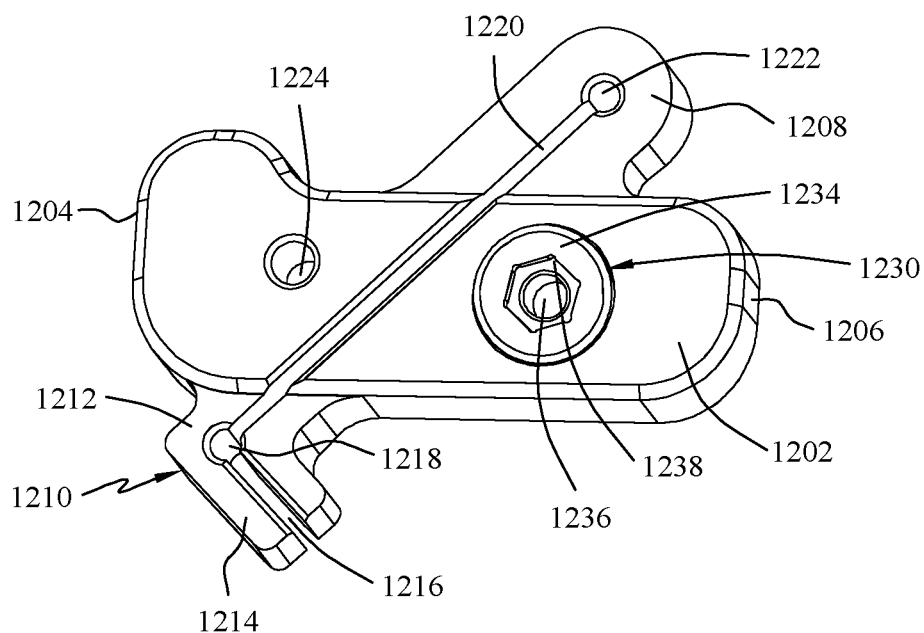
FIG. 40 is a front view of the assembled resection guide of FIG. 39, in accordance with an aspect of the present invention.
Figure 41:
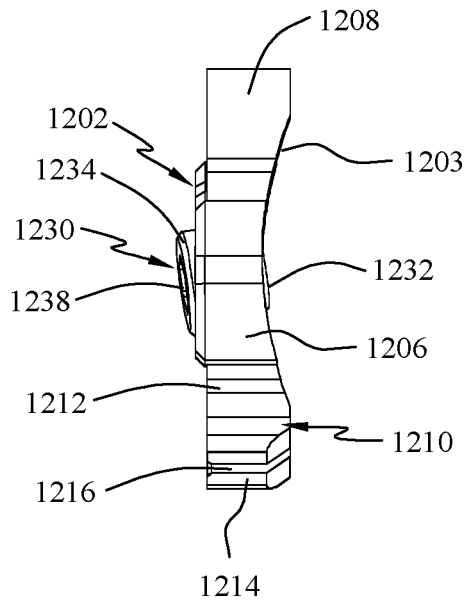
FIG. 41 is a first end view of the resection guide of FIG. 39, in accordance with an aspect of the present invention.
Figure 42:
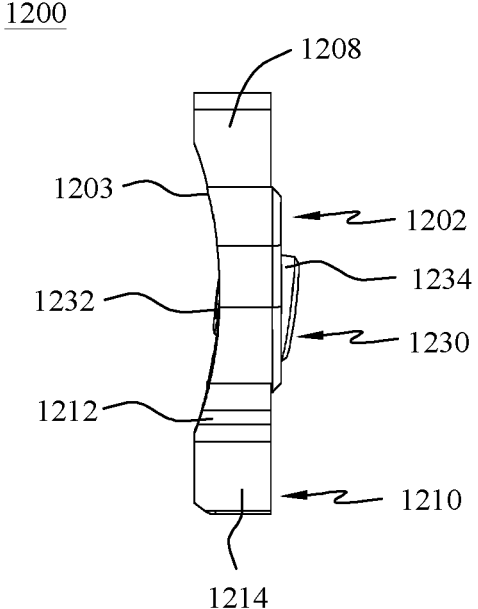
FIG. 42 is a second end view of the resection guide of FIG. 39, in accordance with an aspect of the present invention.
Figure 43:
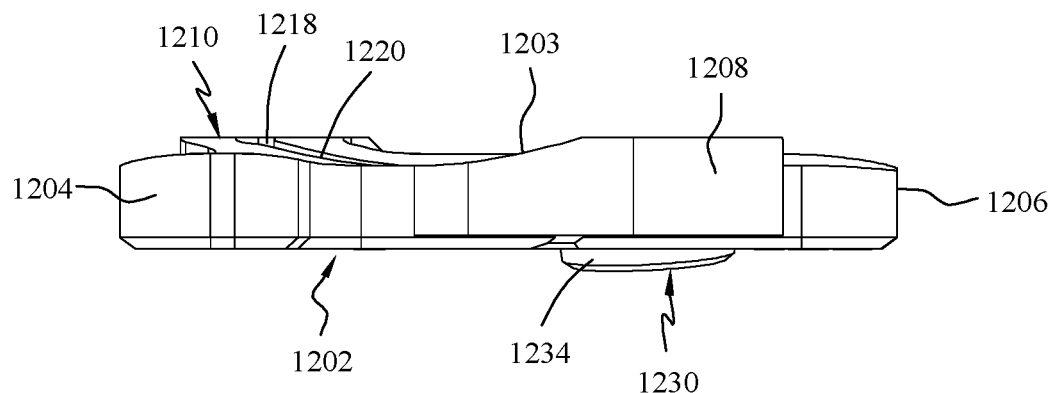
FIG. 43 is a top view of the resection guide of FIG. 39, in accordance with an aspect of the present invention.
Figure 44:
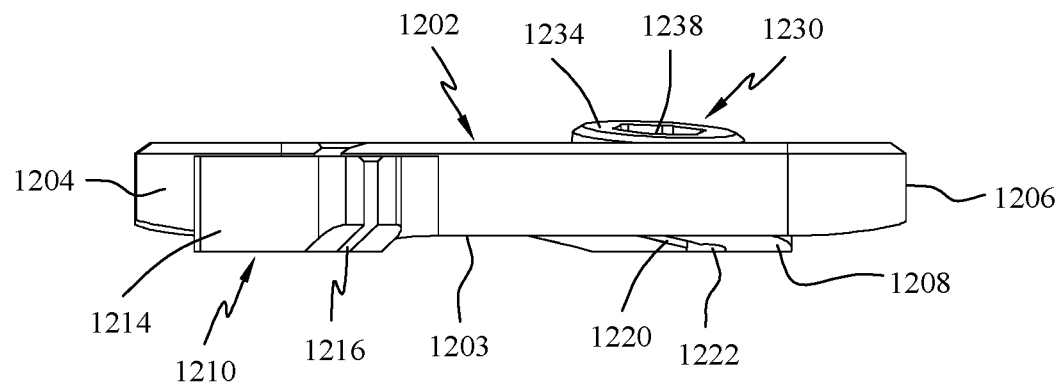
FIG. 44 is a bottom view of the resection guide of FIG. 39, in accordance with an aspect of the present invention.
Figure 45:
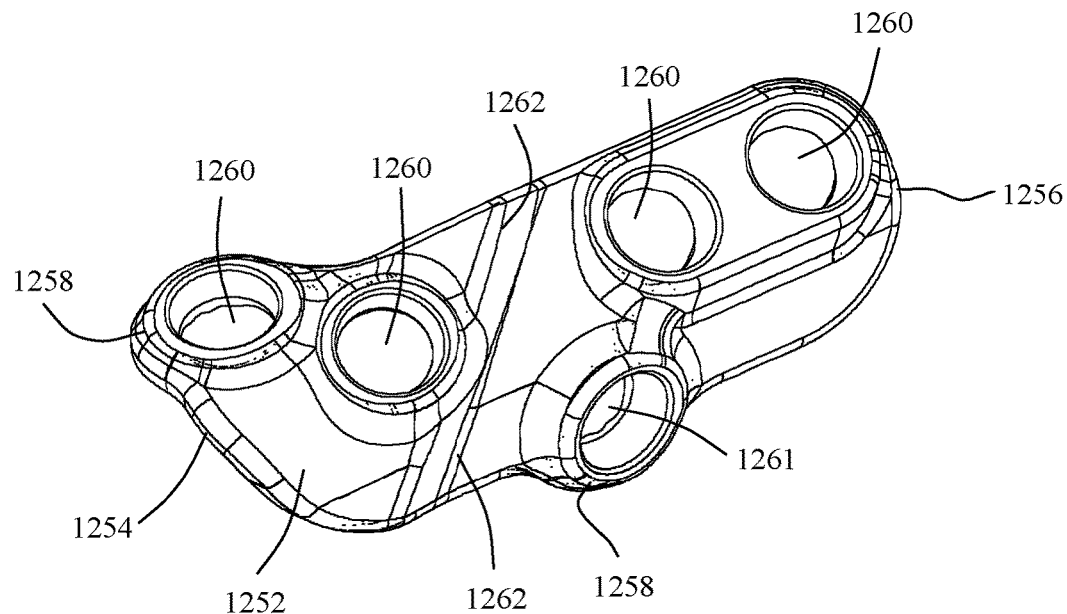
FIG. 45 is a perspective view of a bone plate, in accordance with an aspect of the present invention.
Figure 46:
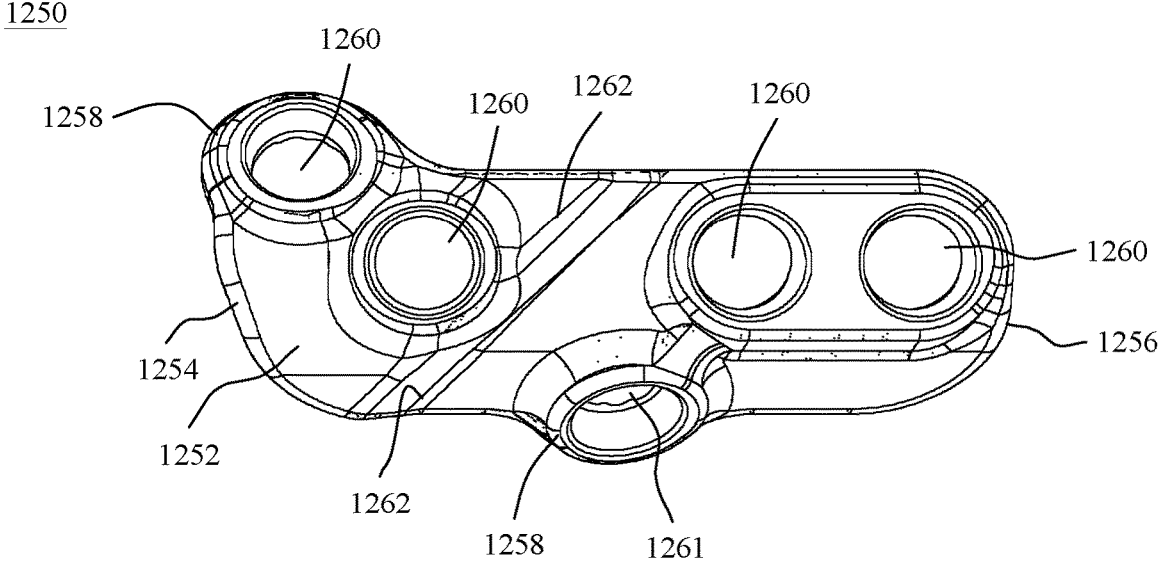
FIG. 46 is a top view of the plate of FIG. 45, in accordance with an aspect of the present invention.

As shown in FIGS. 39 and 40, the first slot 1216 may extend into the second extension 1210 until engaging a first opening 1218 positioned in the second extension 1210. A second slot 1220 may extend from the first opening 1218 in the second extension 1210 across the body 1202 at an angle and into the first extension 1208 at the same angulation as the first extension 1208. The second slot 1220 may end at a second opening 1222 positioned in the first extension 1208. The first and second slots 1216, 1220 and the first and second openings 1218, 1222 may extend through the entire thickness of the guide 1200. The first and second slots 1216, 1220 may be, for example, configured to receive a saw blade (not shown). The first and second openings 1218, 1222 may be configured for a saw blade (not shown) to engage and to receive a k-wire or pin. The resection guide 1200 may also include a third opening 1224 positioned between a midpoint of the resection guide 1200 and the first end 1204. The third opening 1224 may be used, for example to secure the resection guide 1200 to a bone for resection.

The resection guide 1200 may also include a fourth opening 1228, as shown in FIG. 39. The fourth opening 1228 may be, for example, a threaded opening and configured to receive a bushing 1230. The bushing 1230 may include a body or sleeve 1232 with a head 1234 at a first end. The bushing 1230 may also include an opening 1236 extending through the sleeve 1232 and the head 1234 along a longitudinal axis of the bushing 1230. The opening 1236 may be sized to receive a fastener (not shown) to secure the guide 1200 to a patient's bone. The head 1234 may also include a recessed opening 1238 for coupling to a tool for inserting and removing the bushing 1230 from the body 1202. The recessed opening 1238 may have a, for example, hexagonal shape or any other polygonal shape to couple to a tool (not shown). As shown in FIGS. 41-44, the bottom surface 1203 of the body 1202 of the resection guide 1200 may be, for example, curved to match the curvature of the bone being resected.

Figure 63:
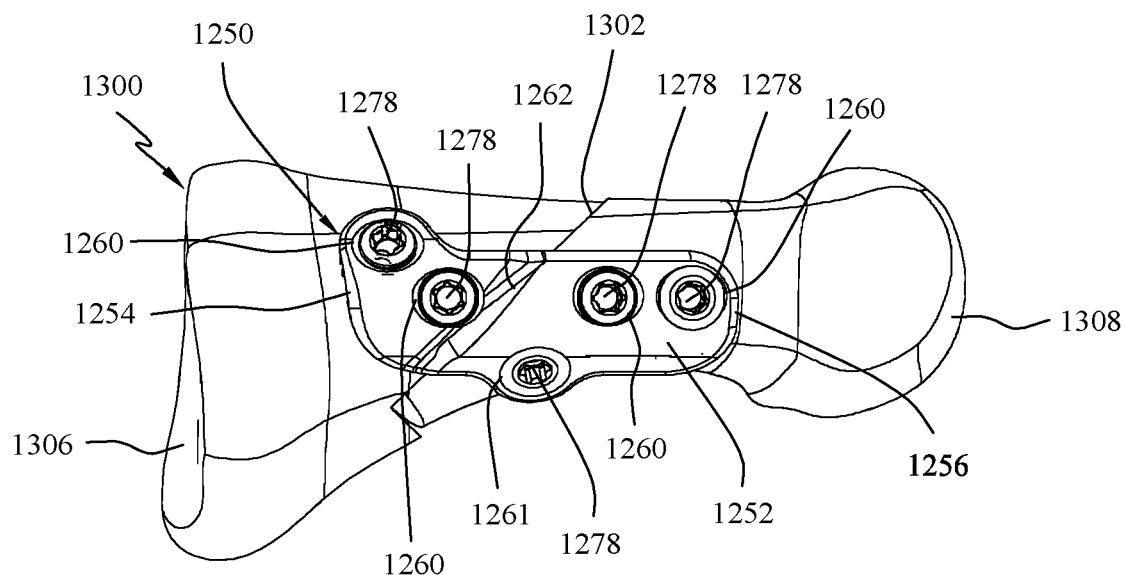
FIG. 63 is a side, perspective view of the plate of FIG. 45 secured to the cut bone with four fasteners, in accordance with an aspect of the present invention.
Figure 64:
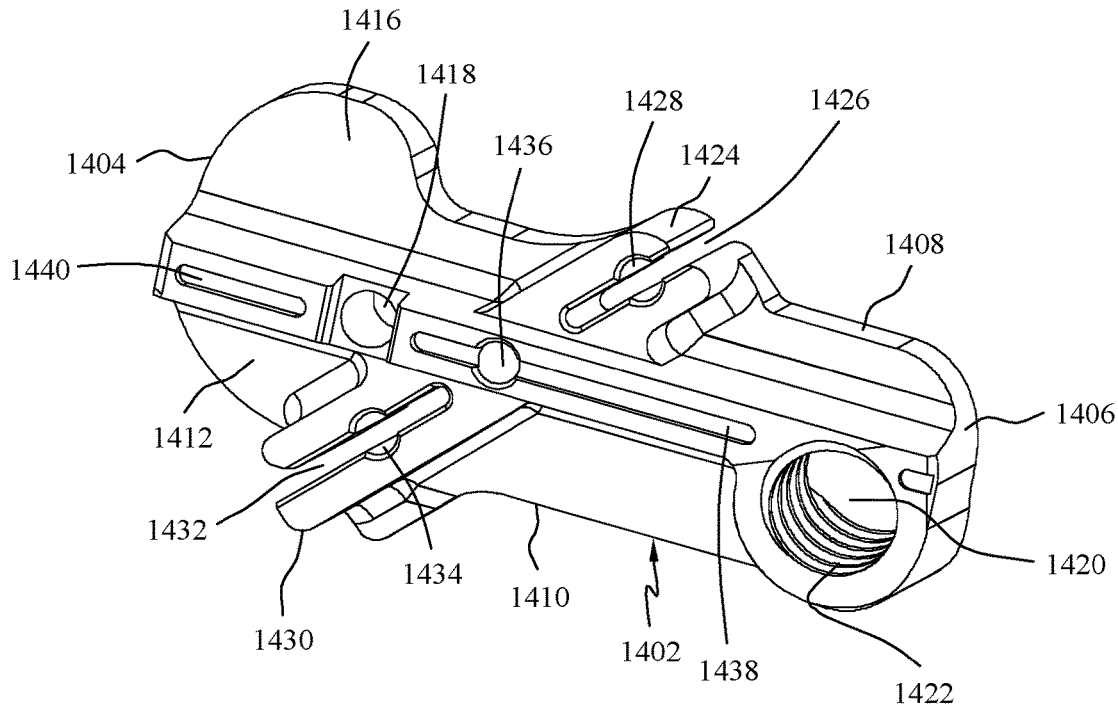
FIG. 64 is a front, perspective view from a first end of another k-wire guide, in accordance with an aspect of the present invention.
Figure 65:
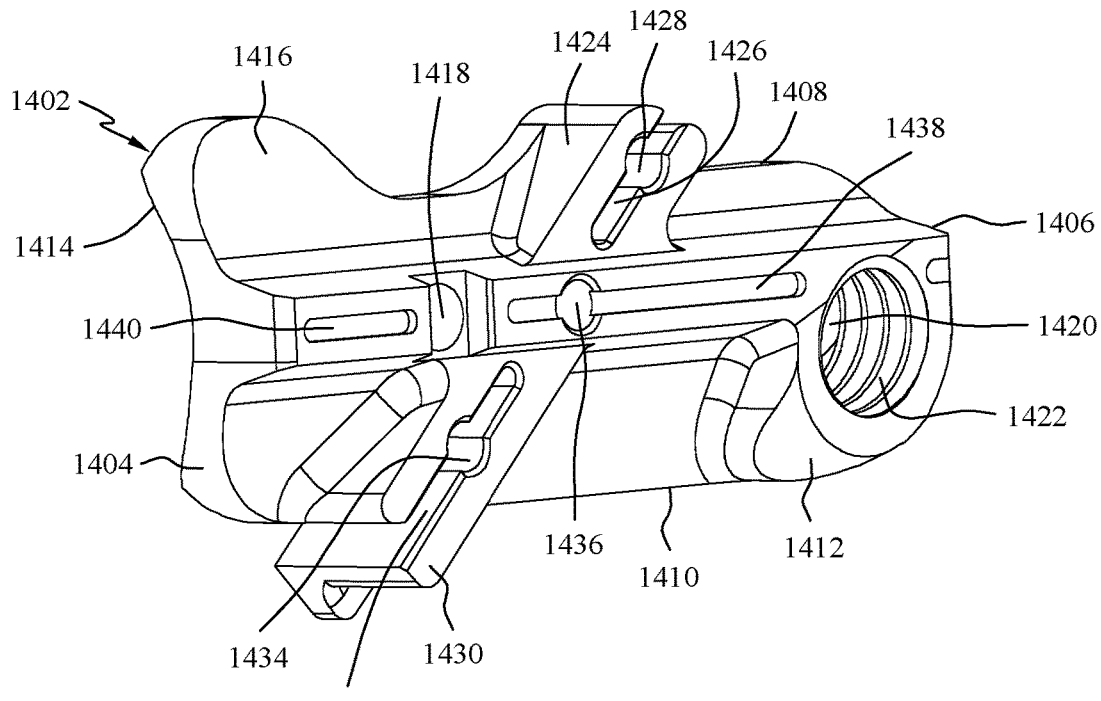
FIG. 65 is a perspective view from a second end of the k-wire guide of FIG. 64, in accordance with an aspect of the present invention.
Figure 66:
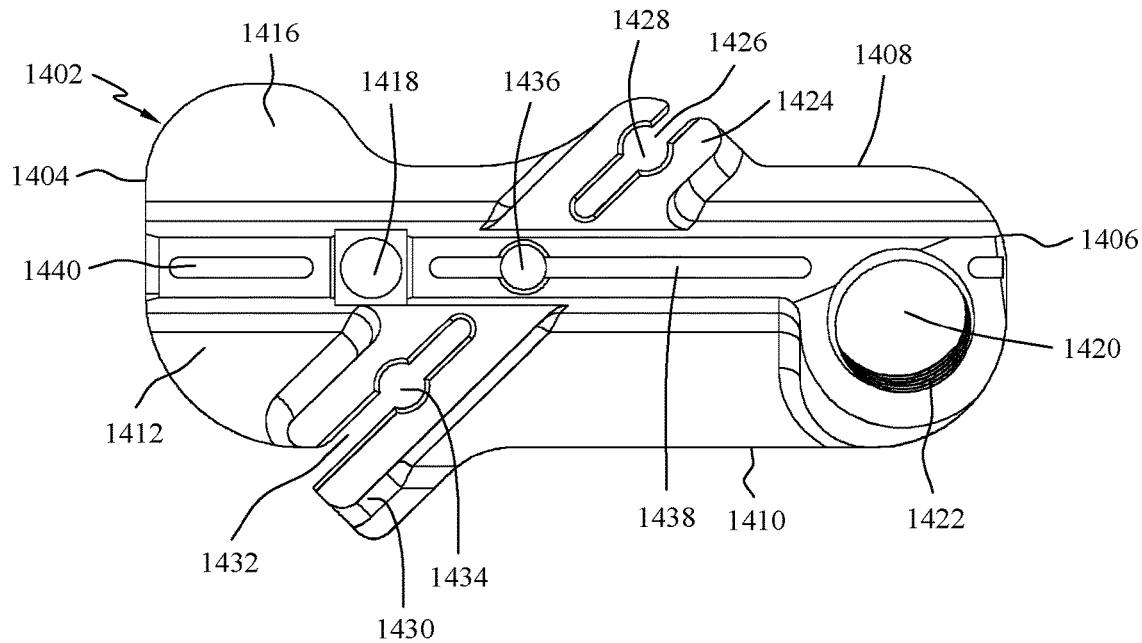
FIG. 66 is a front view of the k-wire guide of FIG. 64, in accordance with an aspect of the present invention.
Figure 67:
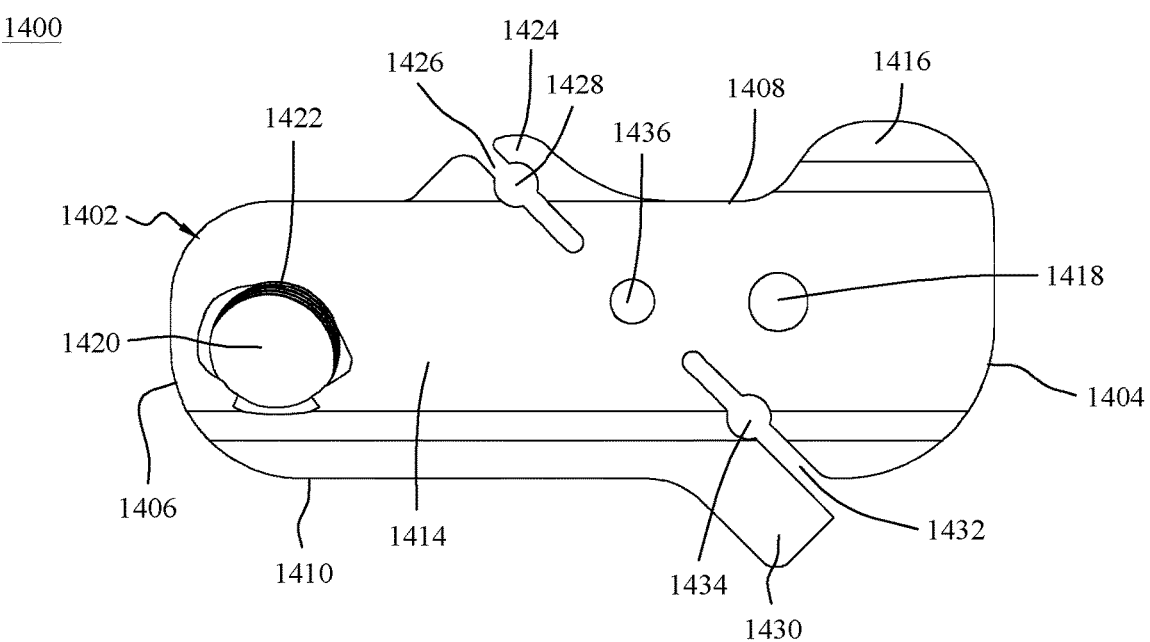
FIG. 67 is a back view of the k-wire guide of FIG. 64, in accordance with an aspect of the present invention.
Figure 68:
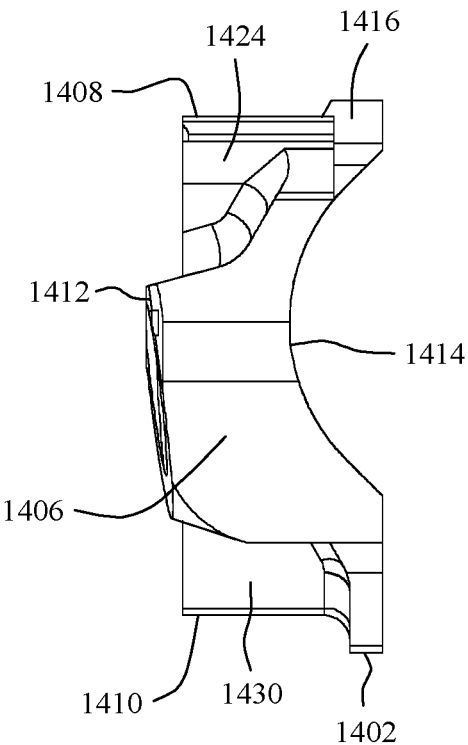
FIG. 68 is a first end view of the k-wire guide of FIG. 64, in accordance with an aspect of the present invention.
Figure 69:
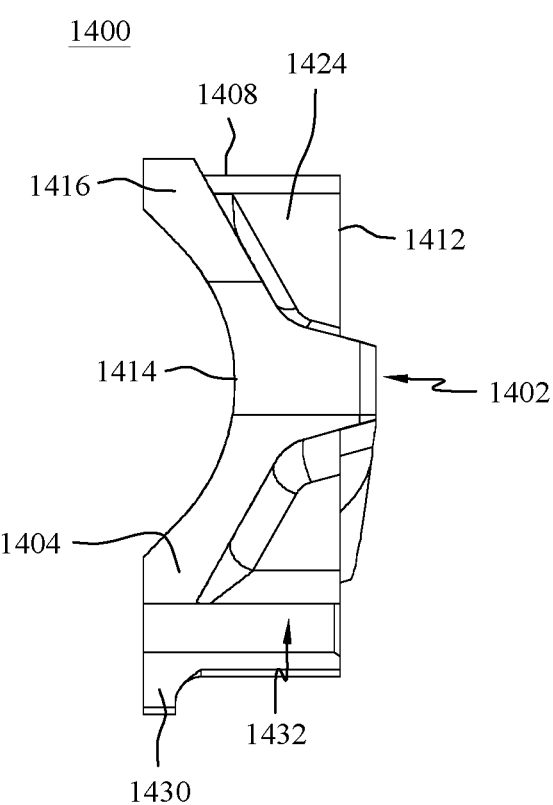
FIG. 69 is a second end view of the k-wire guide of FIG. 64, in accordance with an aspect of the present invention.
Figure 70:
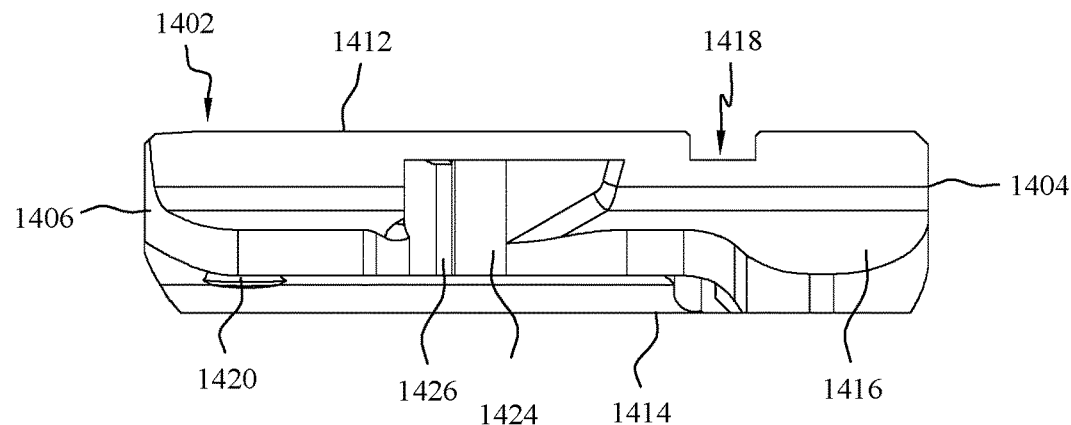
FIG. 70 is a first side view of the k-wire guide of FIG. 64, in accordance with an aspect of the present invention.
Figure 71:
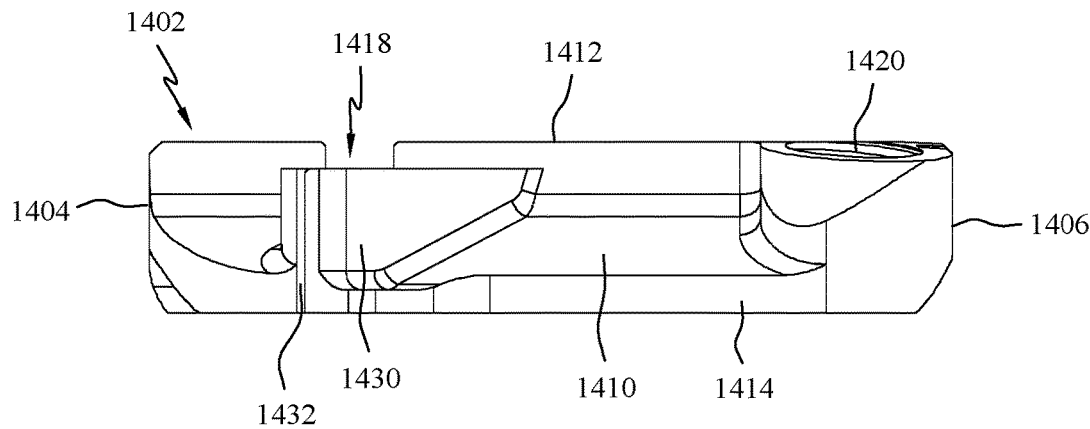
FIG. 71 is a second side view of the k-wire guide of FIG. 64, in accordance with an aspect of the present invention.

Referring now to FIGS. 45-51, a bone plate 1250 is shown. The bone plate 1250 may come in multiple sizes based on the desired angle of correction, for example, the bone plate 1250 may be offered in sizes to provide for between 2° and 20° of angular correction, or more specifically, approximately 5°, 7.5°, 10°, 12.5°, or 15° of angular correction. The angle of correction provided by each plate 1250 may be measured by measuring the angle between the proximal bone axis and distal bone axis after the osteotomy is performed. The bone plate 1250 may also be configured for placement on either the right side of the bone or the left side of the bone. The bone plate 1250 may include a body 1252 with a first end 1254 and a second end 1256. The bone plate 1250 may also include at least one tab portion 1258 extending away from the body 1252. The depicted bone plate 1250 includes a first tab portion 1258 extending away from a first side near the first end 1254 and a second tab portion 1258 extending away from a second side near the middle of the plate 1250. The bone plate 1250 may also include a plurality of openings 1260, 1261 for securing the bone plate 1250 to a bone, as shown in FIG. 63. As depicted, the bone plate 1250 may include, for example, five openings 1260, 1261 with two openings 1260 positioned near the first end 1254 of the plate 1250, two openings 1260 positioned near the second end 1256 of the plate 1250, and one opening 1261 positioned near a mid-point of the plate 1250. The openings 1260, 1261 may be, for example, threaded or tapered openings configured to receive locking or non-locking bone fasteners or screws. The opening 1261 may be positioned in the second tab portion 1258. The opening 1261 may be, for example, angled to allow for a fastener (not shown) to be inserted through the opening 1261 across the cut bone to engage both portions of bone. The bone plate 1250 may also include at least one alignment marking 1262 for aligning with the osteotomy surface of the bone, for example, with the distal portion of a metatarsal bone after resection.

Figure 47:
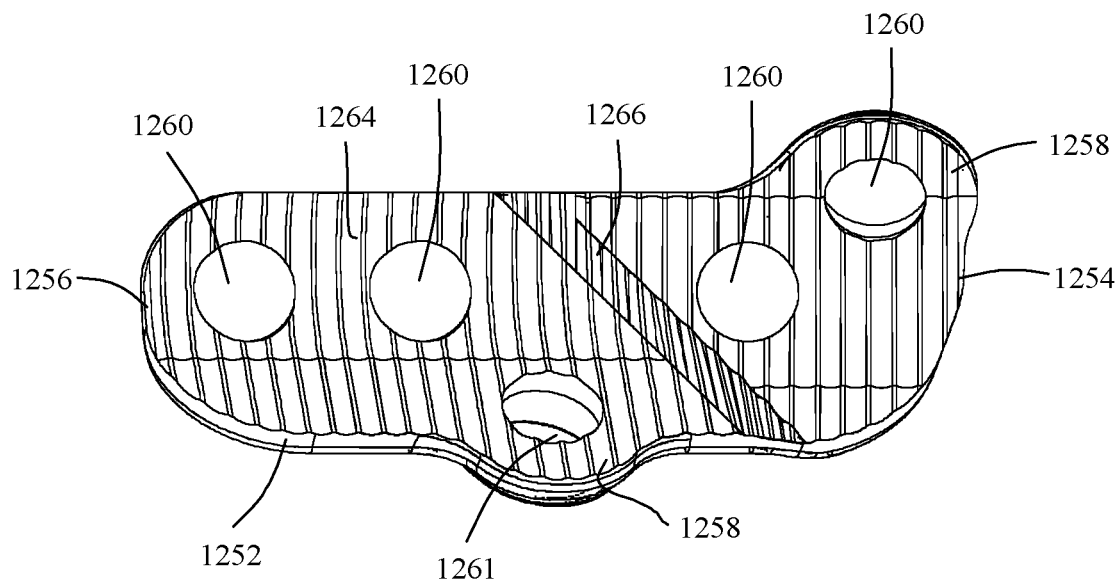
FIG. 47 is a bottom view of the plate of FIG. 45, in accordance with an aspect of the present invention.
Figure 48:
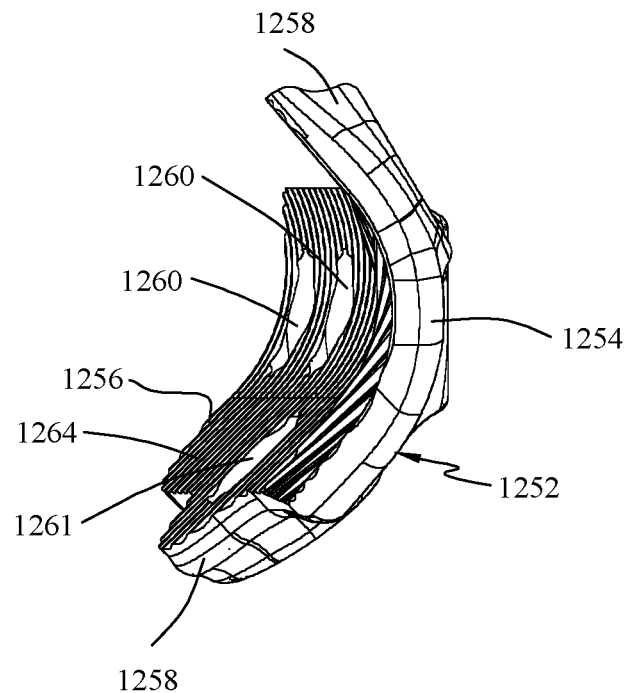
FIG. 48 is a first end view of the plate of FIG. 45, in accordance with an aspect of the present invention.
Figure 49:
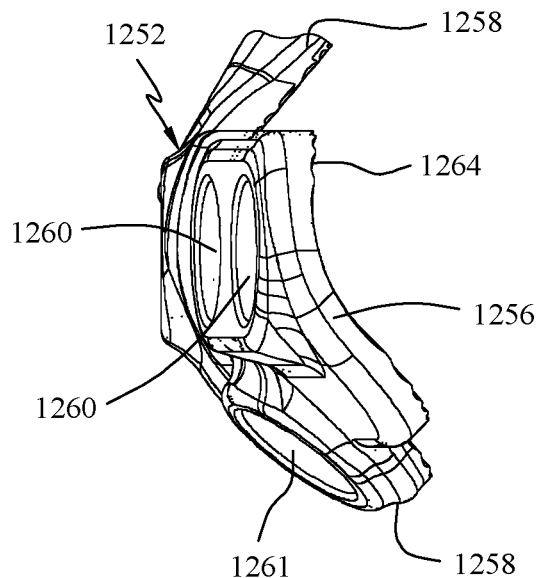
FIG. 49 is a second end view of the plate of FIG. 45, in accordance with an aspect of the present invention.
Figure 50:
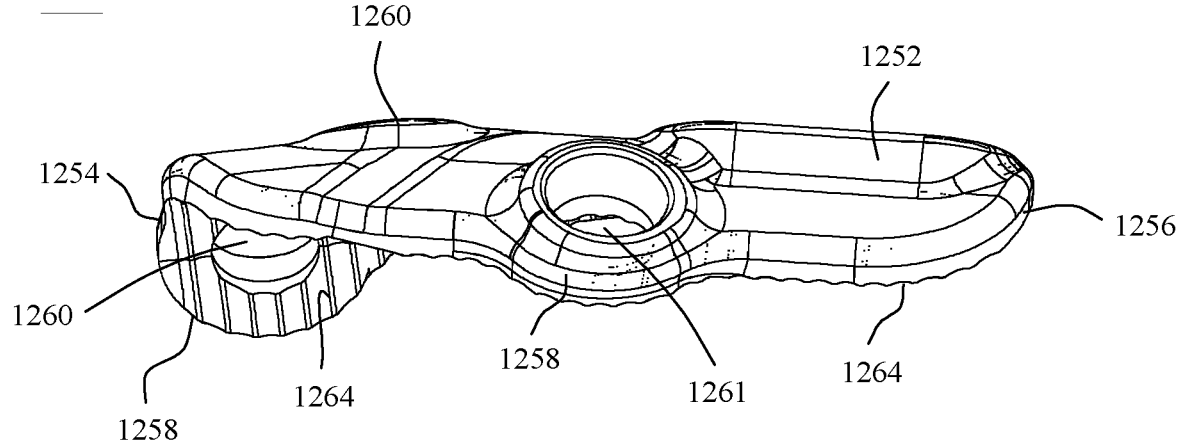
FIG. 50 is a first side view of the plate of FIG. 45, in accordance with an aspect of the present invention.
Figure 51:
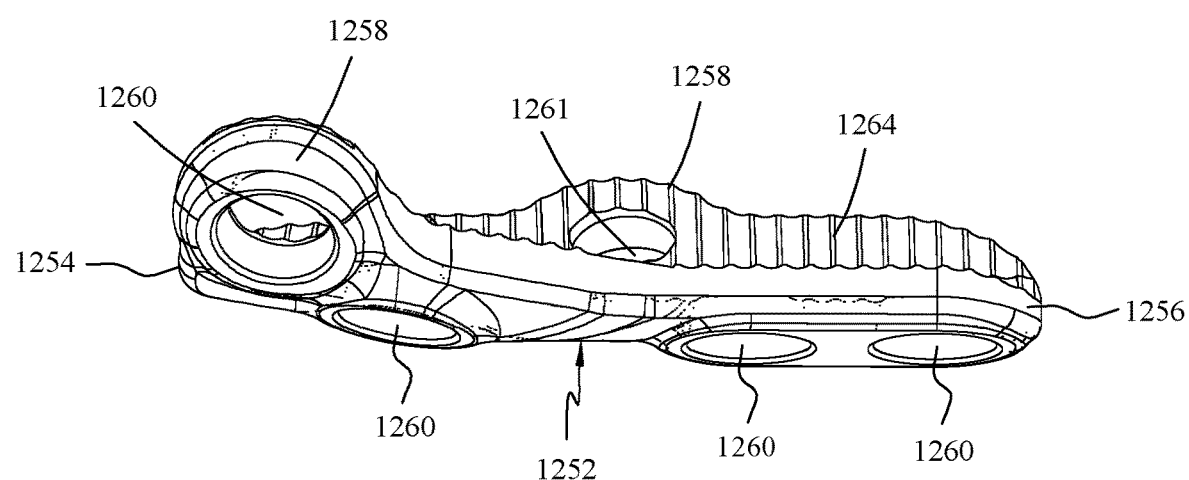
FIG. 51 is a second side view of the plate of FIG. 45, in accordance with an aspect of the present invention.

As shown in FIG. 47, the bottom or back surface of the bone plate 1250 may have, for example, a first bone contacting surface 1264 and a second bone contacting surface 1266 positioned to align with the cut surface of the bone. The first bone contacting surface 1264 may comprise the entire bottom surface of the bone plate 1250 except where the second bone contacting surface 1266 is positioned. The bone contacting surfaces 1264, 1266 may have the same surface texture or a different surface texture and may be, for example, a micro or macro grooved or irregular bone contacting surface to aid in bone plate stability and fixation. The bone contacting surface may be, for example, a series of grooves, waves, serrations, scallops, or other contoured surface structures.

As shown in FIGS. 48-51, the bone plate 1250 may be, for example, curved to match the curvature of the outer surface of the bone being resected to mimic a healthy bone shape. The plate 1250 may be contoured to provide specific angulation or re-angulation after bone alteration, i.e., an osteotomy. The plate 1250 provides the ability to create an angular change to the long axis of the bone by forming the angle in the bone contour surfaces, which are different from one end to the other. The tabs 1258 may provide additional rigidity for the bone-plate construct.

Figure 52:
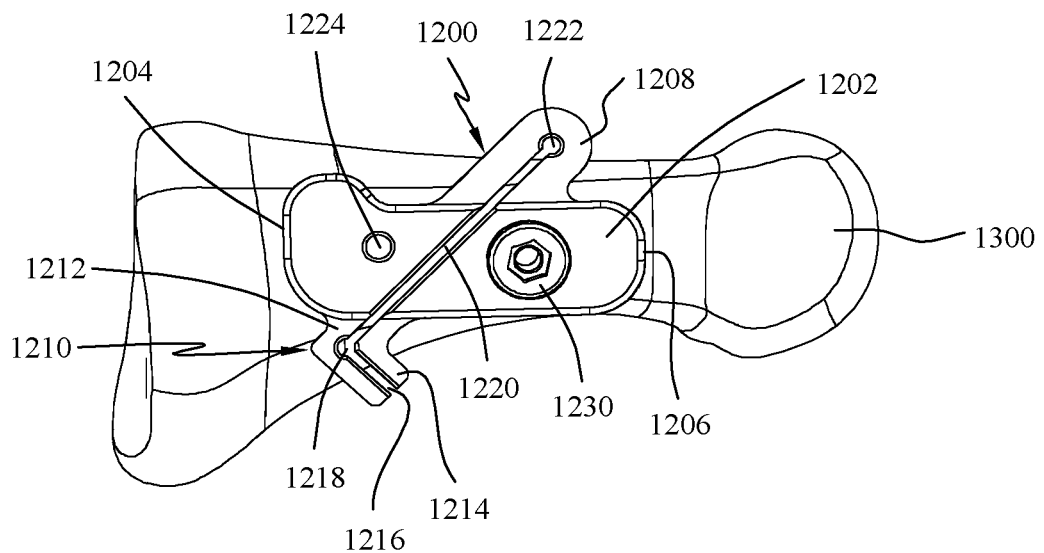
FIG. 52 is a front view of the resection guide of FIG. 39 aligned on a bone, in accordance with an aspect of the present invention.
Figure 53:
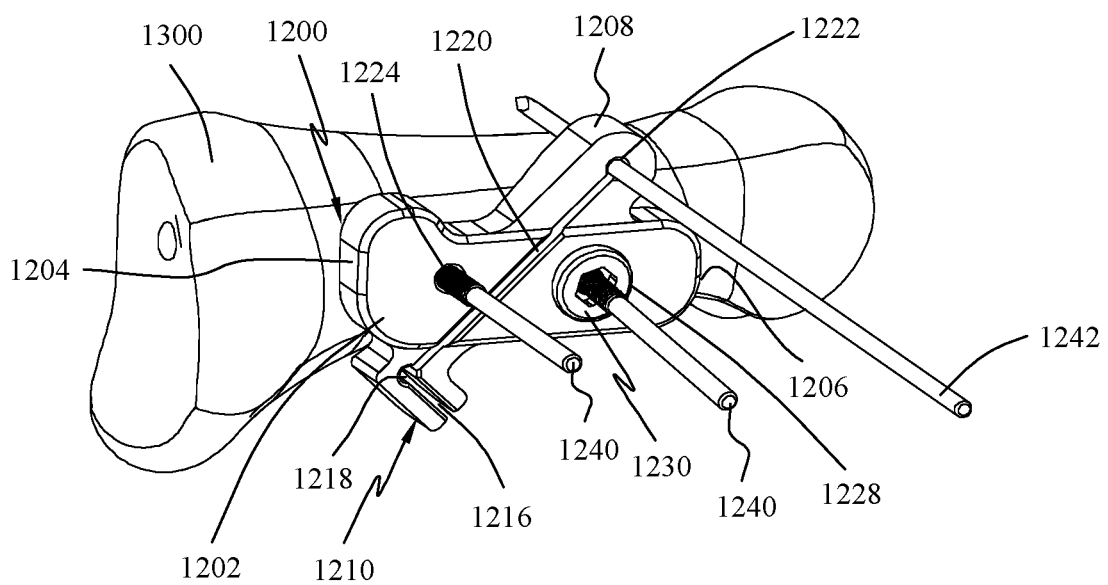
FIG. 53 is a perspective view of the resection guide of FIG. 39 with fasteners inserted into the bone, in accordance with an aspect of the present invention.
Figure 54:
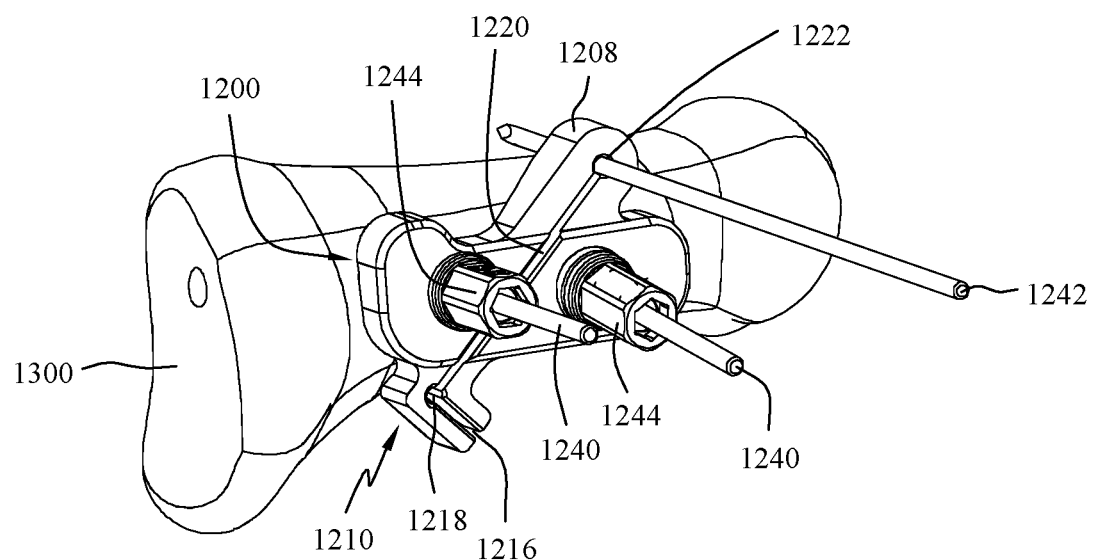
FIG. 54 is a perspective view of the resection guide of FIG. 39 with nuts securing the resection plate to the bone, in accordance with an aspect of the present invention.

Referring now to FIGS. 52-63, a method of using the resection guide 1200 and the plate 1250 is shown. The method may include positioning the resection guide 1200 onto a bone 1300, for example, a metatarsal bone, as shown in FIG. 52. The resection guide 1200 may be positioned, for example, on the tension side of the bone 1300. The resection guide 1200 may also be positioned, for example, below the equator or midline of the bone 1300 to provide a smoother medial final construct. Once the guide 1200 is in the desired position, a first threaded pin 1240 may be inserted through the third opening 1224 and into the bone 1300 and a second threaded pin 1240 may be inserted through the opening 1236 and into the bone 1300, as shown in FIG. 53. Also shown in FIG. 53, a k-wire 1242 may be inserted through the second opening 1222 to confirm the proper placement of the guide 1200. Next, as shown in FIG. 54, nuts or other like securement members 1244 may be inserted over the pins 1240 and the interior surface of the nuts 1244 may be threaded to engage the threads of the pins 1240. The nuts 1244 may be tightened to secure the guide 1200 to the patient's bone 1300.

Figure 55:
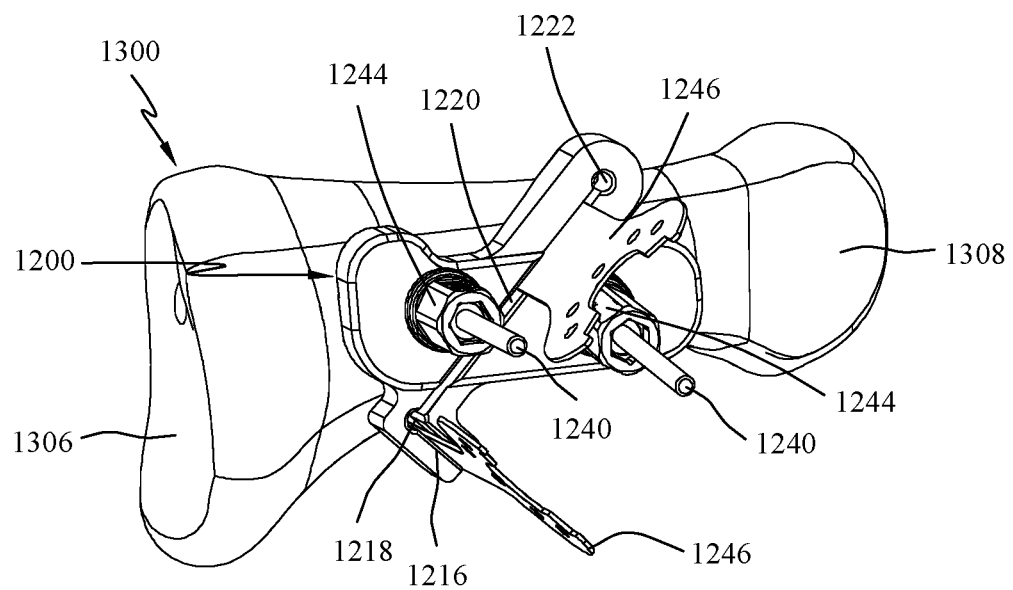
FIG. 55 is a perspective view of the resection guide of FIG. 39 with the bone saw blades positioned to cut the bone, in accordance with an aspect of the present invention.
Figure 56:
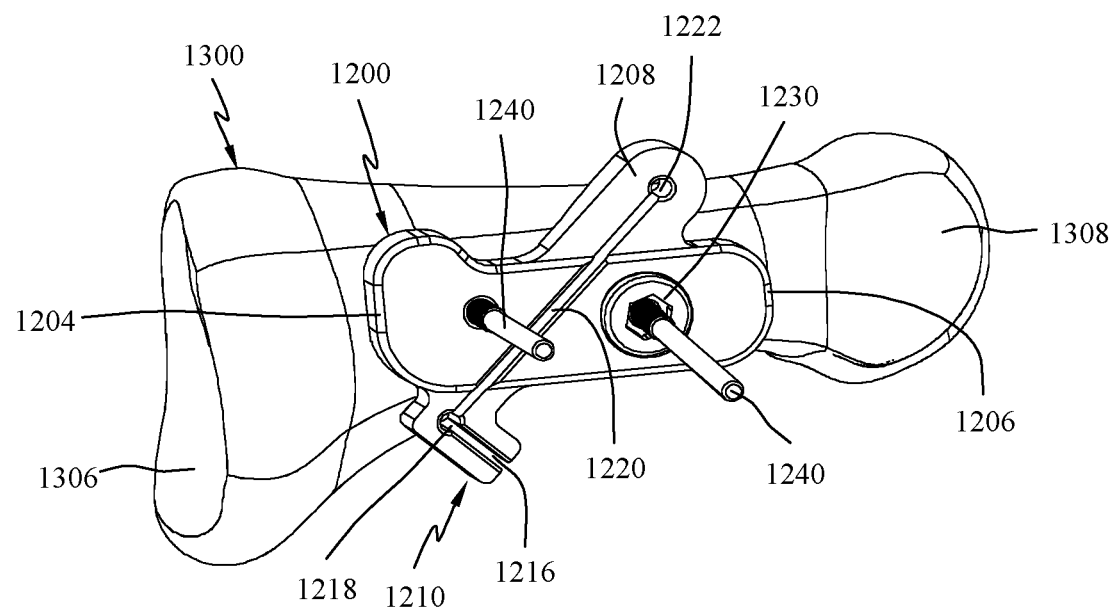
FIG. 56 is a perspective view of the resection guide of FIG. 39 after the bone is cut and the bone saw blades and nuts are removed, in accordance with an aspect of the present invention.
Figure 57:
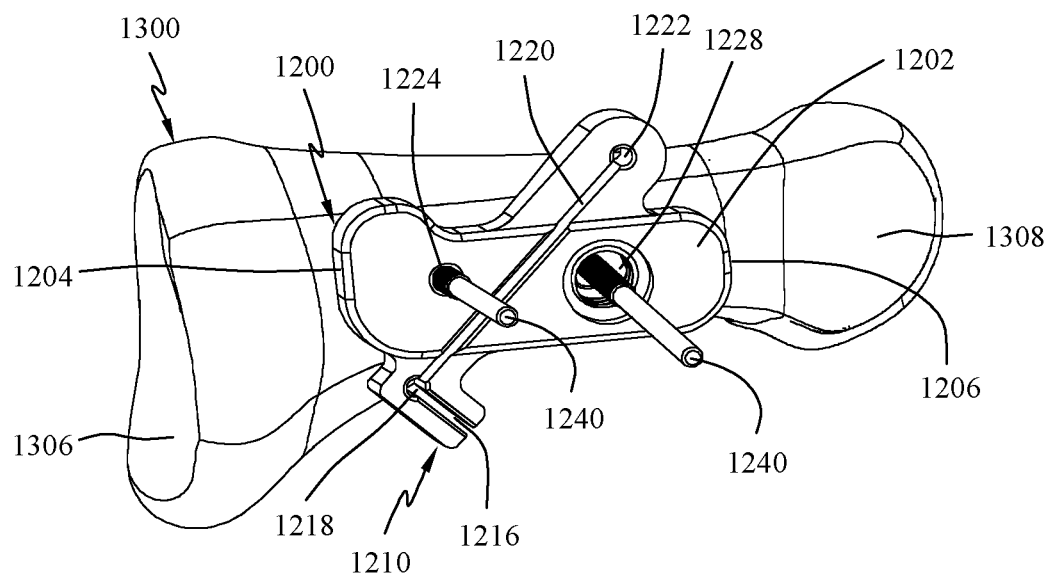
FIG. 57 is a perspective view of the resection guide of FIG. 39 after the distal bushing is removed, in accordance with an aspect of the present invention.
Figure 58:
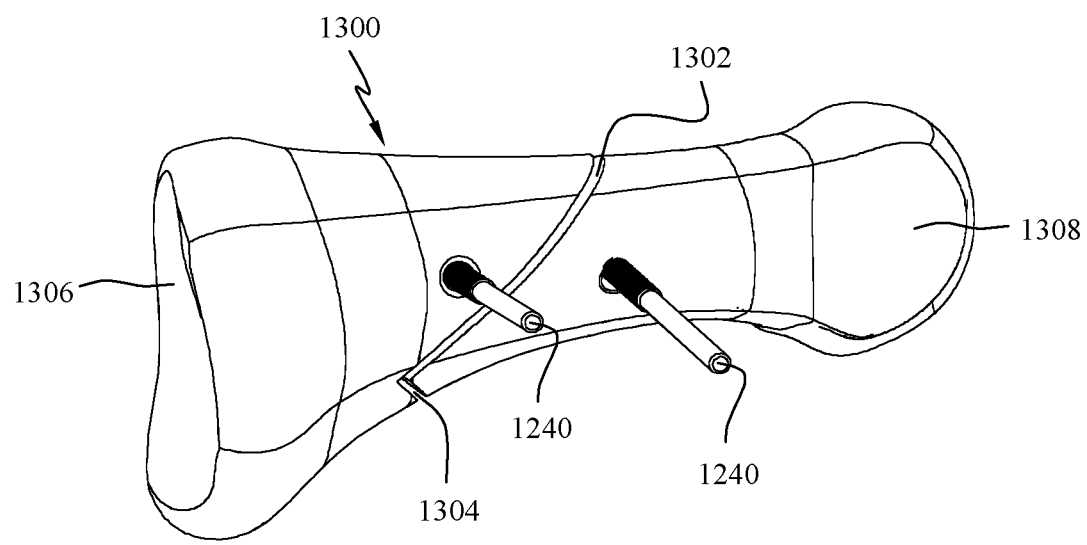
FIG. 58 is a perspective view of the cut bone with the two fasteners positioned in the bone after the resection guide is removed, in accordance with an aspect of the present invention.
Figure 59:
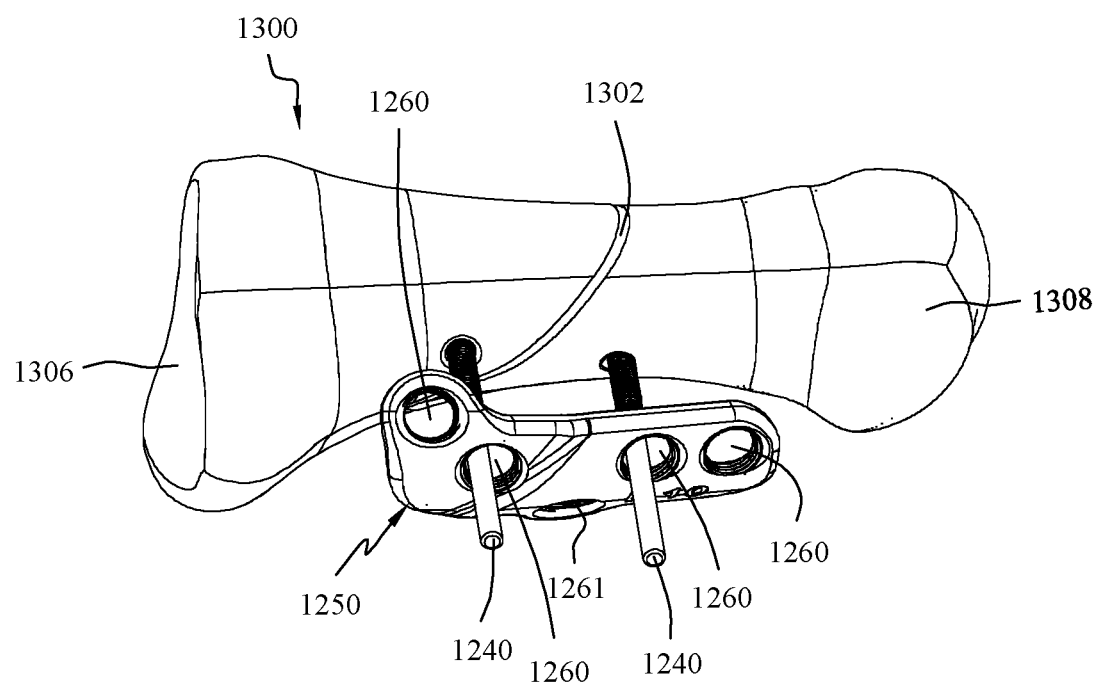
FIG. 59 is a perspective view of the cut bone with a plate being positioned on the two fasteners, in accordance with an aspect of the present invention.
Figure 60:
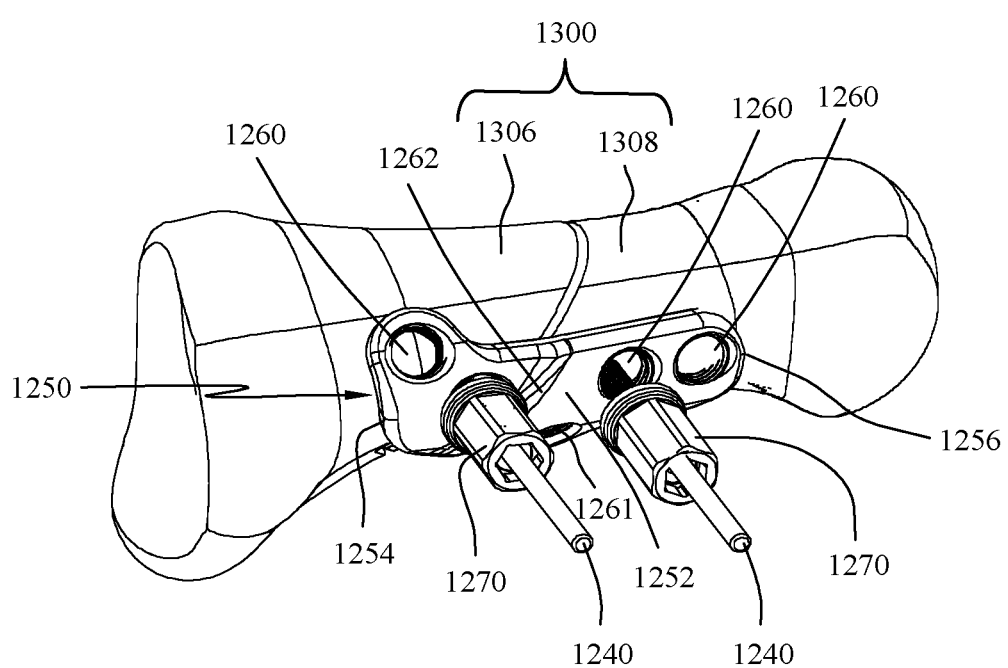
FIG. 60 is a perspective view of the cut bone with the plate of FIG. 45 positioned on the bone and secured with two nuts, in accordance with an aspect of the present invention.
Figure 61:
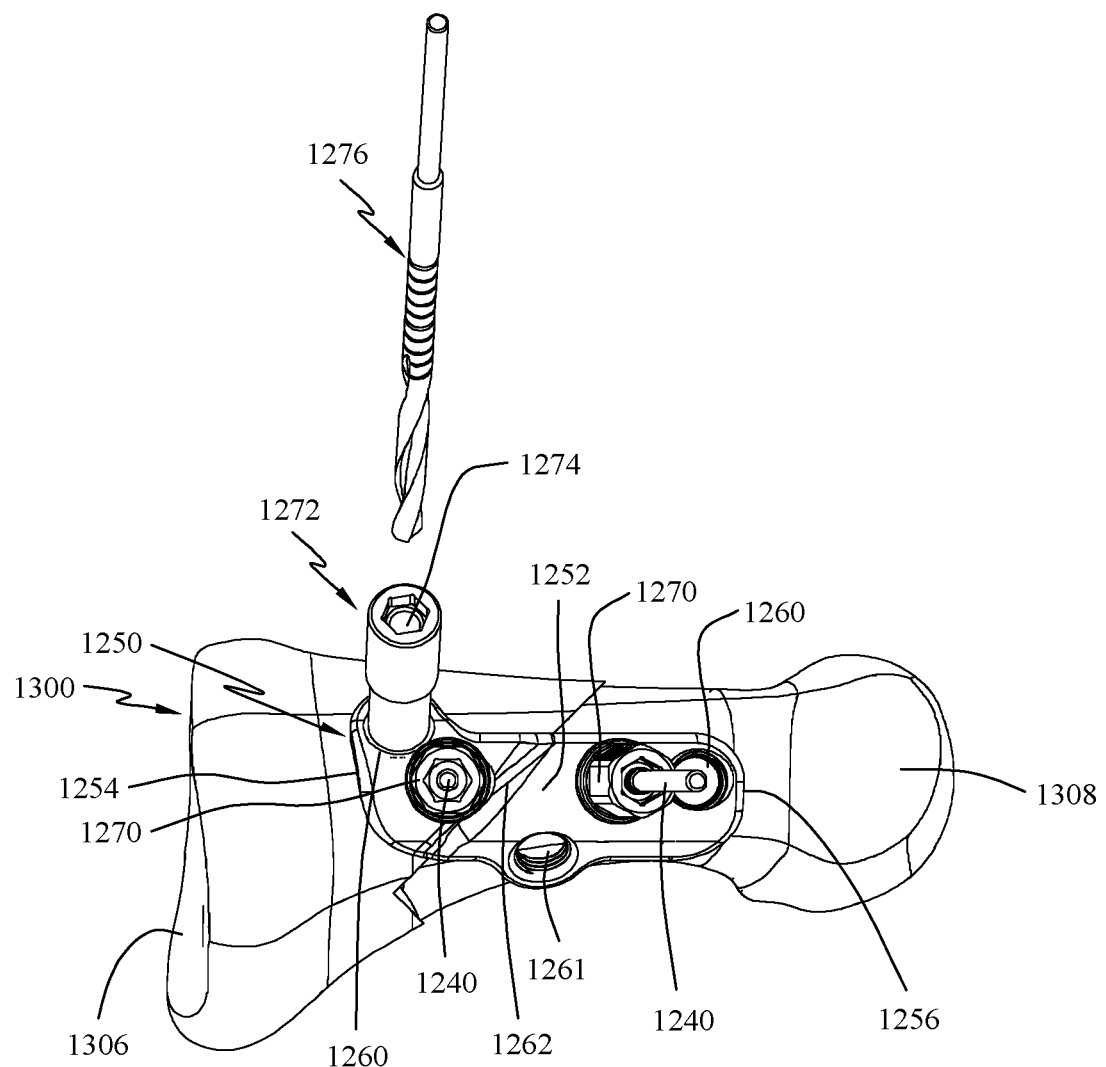
FIG. 61 is a side, perspective view of the cut bone and the plate of FIG. 45 with a drill sleeve inserted into the plate and a portion of a drill being inserted into the drill sleeve, in accordance with an aspect of the present invention.

After the resection guide 1200 is secured to the bone 1300, a saw may be used to perform the osteotomy by, for example, inserting a saw blade 1246 into each of the first and second slots 1216, 1220, as shown in FIG. 55. The first and second slots 1216, 1220 allow for two cuts to be made on the bone 1300. For example, a first cut 1302 may be made using the second slot 1220 and a second cut 1304 may be made using the first slot 1216. The first and second cuts 1302, 1304 may divide the bone 1300 into a first portion 1306 and a second portion 1308. Once the cuts are performed, the saw blades 1246 and nuts 1244 may be removed from the guide 1200, as shown in FIG. 56. The bushing 1230 may also be removed from the body 1202 of the guide, as shown in FIG. 57. Then, the guide 1200 may be removed from the bone 1300, leaving the first and second threaded pins 1240 in the bone 1300. As shown in FIG. 58, the first pin 1240 may be inserted into the first bone portion 1306 and the second pin 1240 may be inserted into the second bone portion 1308. Next, as seen in FIG. 59, a plate 1250 may be aligned with and inserted over the pins 1240. The pins 1240 may be inserted through two openings 1260 in the plate 1250. Once the plate 1250 is positioned on the bone portions 1306, 1308, two nuts 1270 may be inserted over the pins 1240 and the interior surface of the nuts 1270 may be threaded to engage the threads of the pins 1240, as shown in FIG. 60. As the nuts or other like securement members 1270 are tightened on the pins 1240 the bones 1306, 1308 are reduced and realigned, as shown in FIG. 61. The plate 1250 is moved into the desired position.

Figure 62:
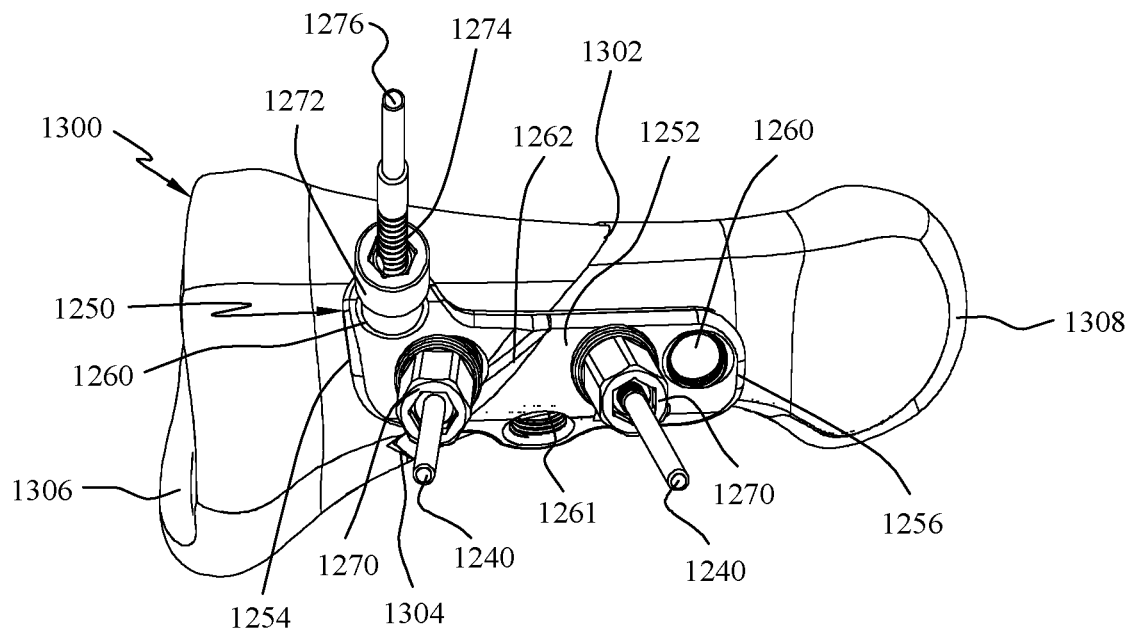
FIG. 62 is a side, perspective view of the cut bone and the plate of FIG. 45 with the portion of the drill inserted into the drill sleeve, in accordance with an aspect of the present invention.

As seen in FIGS. 61 and 62, a drill sleeve or drill tube 1272 may be coupled to one of the openings 1260, 1261 and a drill bit 1276 may be inserted into the opening 1274 in the drill tube 1272 to drill a hole into the bone 1300. After the first hole is drilled, the drill bit 1276 and drill tube 1272 may be removed from the plate 1250. Next, a fastener 1278, for example, a locking or non-locking bone screw, may be inserted into the hole to secure the plate 1250 to the bone 1300. Additional fasteners 1278 may be inserted into the bone 1300 through each of the openings 1260, 1261 in the plate 1250, as shown in FIG. 63. The additional fasteners 1278 may be inserted into holes in the bone 1300 that were created by the drill bit 1276 following the above sequence. The first hole may be drilled, for example, in the first bone portion 1306 to secure the plate 1250 to the first bone portion 1306. Then, a second hole may be drilled, for example, in the second bone portion 1308 to secure the plate 1250 to the second bone portion 1308 and secure the re-aligned bone 1300 in the desired position. Next, the additional openings 1260, 1261 which do not include a pin 1240 may be drilled and a fastener 1278 inserted. Once at least one fastener 1278 is inserted into each of the first and second bone portions 1306, 1308, the nuts 1270 may be removed either one at a time or simultaneously from the pins 1240 and holes may be drilled into the bone 1300. The holes may be drilled as discussed above in greater detail and which will not be described again here for brevity sake. Fasteners 1278 may be inserted into the holes through the openings 1260, 1261 to secure the plate 1250 to the bone portions 1306, 1308. The patient's incision may then be closed.

Referring now to FIGS. 64-71, a k-wire guide 1400 is shown. The k-wire guide 1400 may include a body 1402 and a bushing, such as bushing 1230 of FIG. 39. The body 1402 may have a first end 1404, a second end 1406, a first side 1408, a second side 1410, a front surface 1412, and a back surface 1414. The body 1402 may also include a projection 1416 extending away from the first side 1408 of the body 1402. The body 1402 may also include a first opening 1418 positioned between a midpoint of the body 1402 and the first end 1404 and a second opening 1420 positioned near the second end 1406. The second opening 1420 may include, for example, threads 1422. The second opening 1420 may be sized to receive a bushing 1230. The body 1402 may have a first extension 1424 projecting out from the first side 1408 near the center of the body 1402 and a second extension 1430 projecting out from the second side 1410 near the center of the body 1402. The first extension 1424 may include a first slot 1426 extending from an end of the first extension 1424 toward the center of the body 1402. The first extension 1424 may also include a first hole 1428 extending from the front surface 1412 to the back surface 1414. The first hole 1428 may be positioned along the first slot 1426. The second extension 1430 may include a second slot 1432 extending from an end of the second extension 1430 toward the center of the body 1402. The second extension 1430 may also include a second hole 1434 extending from the front surface 1412 to the back surface 1414. The second hole 1434 may be positioned along the second slot 1432. The body 1402 may also include a third hole 1436 positioned along the same angle axis that aligns and is between the first slot 1426 and the second slot 1432. The front surface 1412 may also include a first recess 1438 and a second recess 1440 positioned along the longitudinal axis of the body 1402. The third hole 1436 may be positioned along the first recess 1438.

Figure 72:
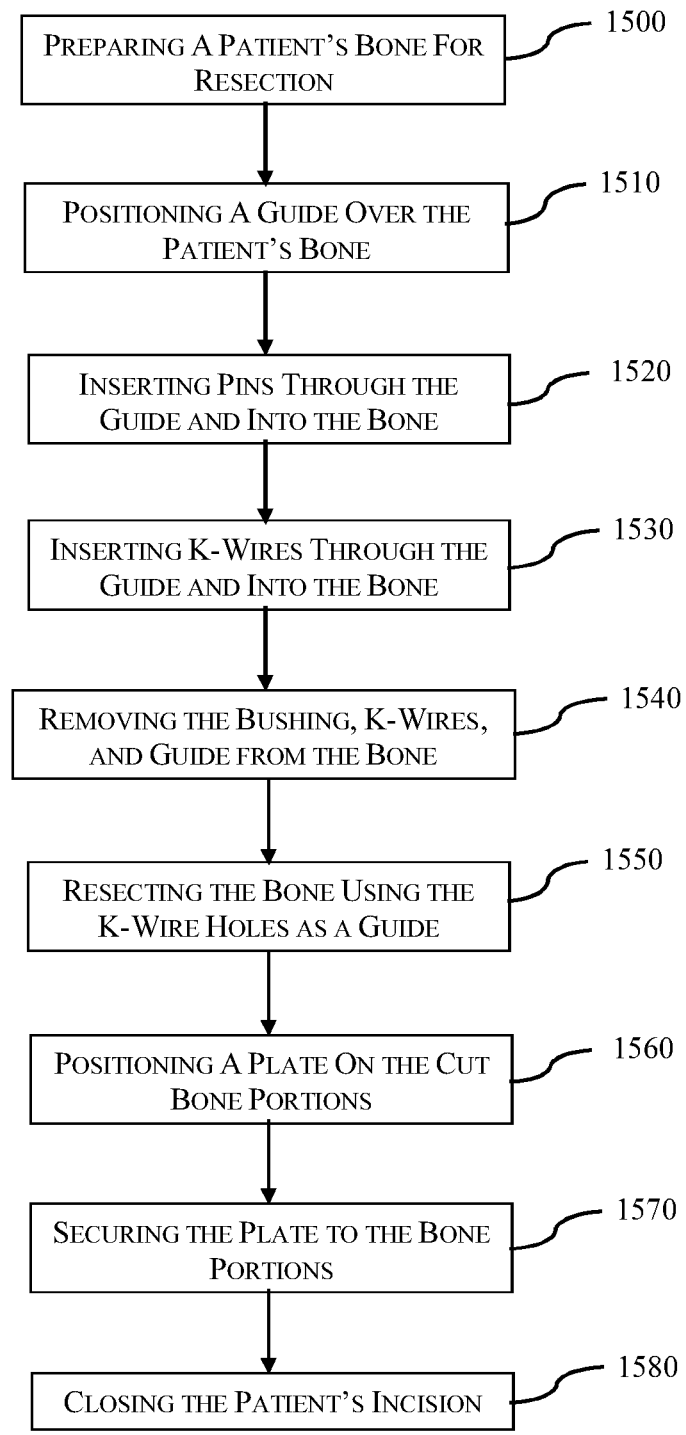
FIG. 72 depicts a method of using the k-wire guide of FIG. 64, in accordance with an aspect of the present invention.

As shown in FIG. 72, a method for using the k-wire guide 1400 and the plate 1250 in accordance with one or more aspects of the present invention may include, for instance: preparing a patient's bone for resection 1500 and positioning the guide over the patient's bone 1510. The method may also include inserting at least two pins through the guide and into the patient's bone 1520 and inserting k-wires through the guide and into the patient's bone 1530. In addition, the method may include removing the bushing, k-wires, and guide from the bone 1540 and resecting the bone using the k-wire holes as a guide 1550. The method may further include positioning the plate with respect to the bone portions 1560 and securing the plate to the bone portions 1570. Finally, the method may include closing the patient's incision 1580.

The method for using the k-wire guide 1400 and the plate 1250 may include preparing a patient's bone for resection. Next, the guide 1400 may be positioned over the bone and pins, for example, pins 1240 of FIGS. 53-62, may be inserted to hold the guide 1400 on the bone. A first pin (not shown) may be inserted into the first opening 1418 of the guide 1400 and a second pin (not shown) may be inserted into through the bushing 1230 in the second opening 1420 of the guide 1400. Then, k-wires (not shown) may be inserted through the first hole 1428, the second hole 1434, and the third hole 1436 and into the bone. Alternatively, the slots 1426, 1432 may be used to score the bone with a blade to provide a guide for the surgeon to cut the patient's bone. After the k-wires are inserted into the bone or the bone has been scored in the slots 1426, 1432, the bushing 1230 may be removed from the k-wire guide 1400. The k-wires may also be removed from the bones leaving three holes in the bone to act as a cut guide for the resection. In addition, the k-wire guide 1400 may be removed from the bone to expose the holes formed by the k-wires. The surgeon may then perform the resection cutting the patient's bone along the holes created by the k-wires. The surgeon may complete the resection by performing an optional scarf cut. The patient's bone will then have a first portion and a second portion, such as, first portion 1306 and second portion 1308 as shown in FIG. 58, and the first pin may be positioned in the first bone portion and the second pin may be positioned in the second bone portion. Next, a plate 1250 may be aligned with and inserted over the pins, such as shown in FIG. 59. The pins may be inserted through two openings 1260 in the plate 1250. Once the plate 1250 is positioned on the bone portions the plate may be secured to the bone portions as described in greater detail above with reference to FIGS. 60-63. After the plate 1250 is secured to the bone portions, the patient's incision may then be closed.

Referring now to FIGS. 73-79, which are transparent depictions of a wire guide 1600 is shown. The wire guide 1600 may be, for example, a solid material, a semi-transparent material, a transparent or clear material and/or any combination thereof. The wire guide 1600 may include a body 1602 and a bushing, such as bushing 1230 of FIG. 39. The body 1602 may have a first end 1604, a second end 1606, a first side 1608, a second side 1610, a front surface 1612, and a back surface 1614. The body 1602 may also include a projection 1616 extending away from the first side 1608 of the body 1602. The body 1602 may also include a first opening 1618 positioned between a midpoint of the body 1602 and the first end 1604 and a second opening 1620 positioned near the second end 1606. The first opening 1618 may be, for example, sized to receive a guide wire (not shown) or alternatively may include a wire guide 1619. The wire guide 1619 may, for example, have an outer diameter sized to mate with the first opening 1618 and an inner diameter sized to receive a wire. The wire guide 1619 may also include, for example, threads or other similar mechanisms on the interior to couple to threads on the guide wire (not shown). In addition, the wire guide 1619 may include, for example, threads on the outer diameter for mating with threads in the first opening 1618. The second opening 1620 may include, for example, threads 1622. The second opening 1620 may be sized to receive a bushing 1230.

Figure 73:
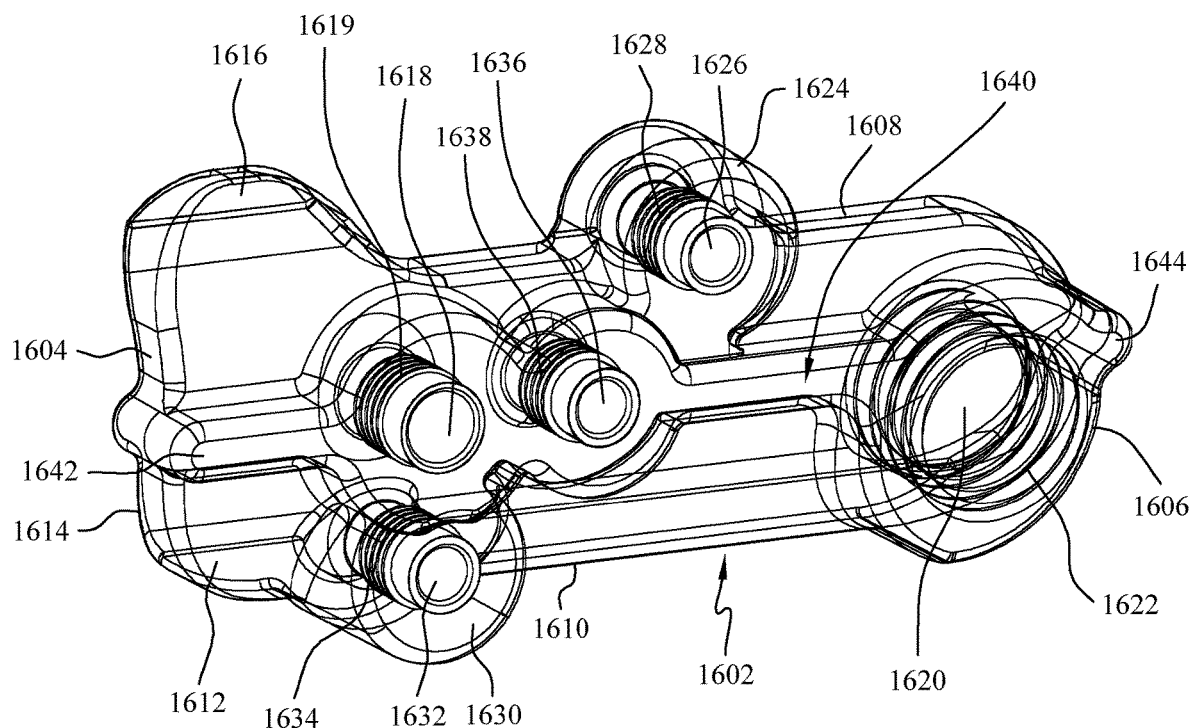
FIG. 73 is a perspective transverse view of a guide, in accordance with an aspect of the present invention.
Figure 74:
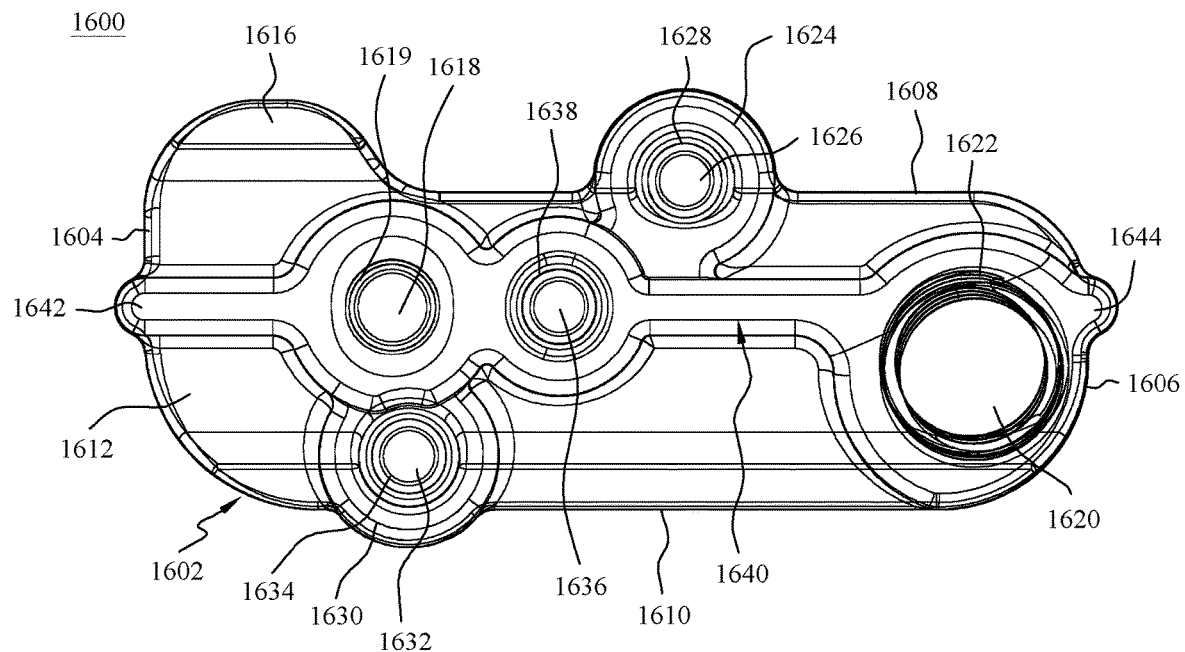
FIG. 74 is a top transverse view of the guide of FIG. 73, in accordance with an aspect of the present invention.
Figure 75:
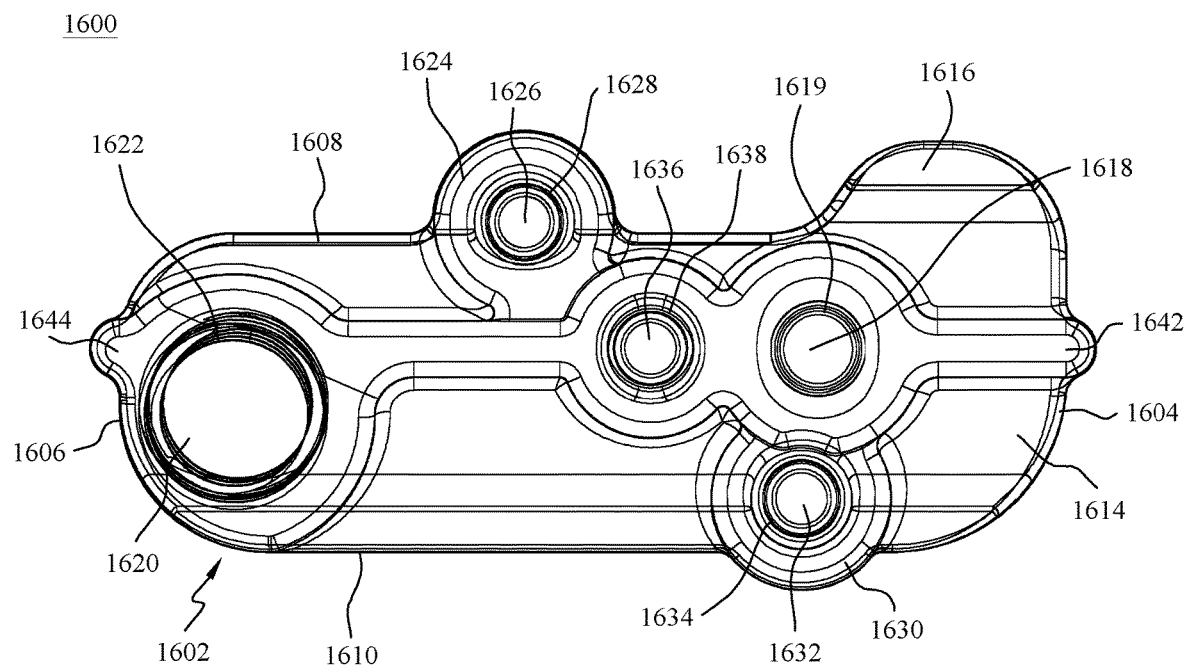
FIG. 75 is a bottom transverse view of the guide of FIG. 73, in accordance with an aspect of the present invention.
Figure 76:
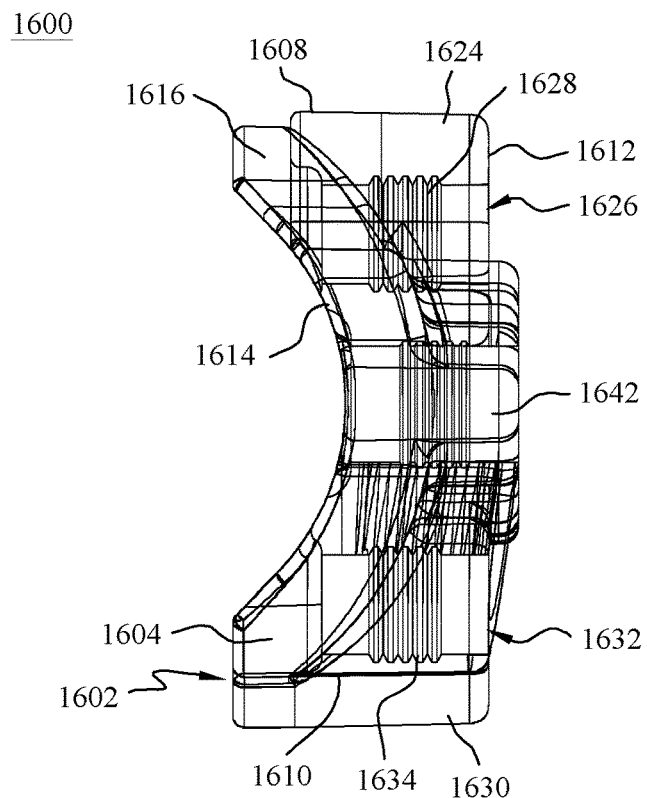
FIG. 76 is a first end transverse view of the guide of FIG. 73, in accordance with an aspect of the present invention.
Figure 77:
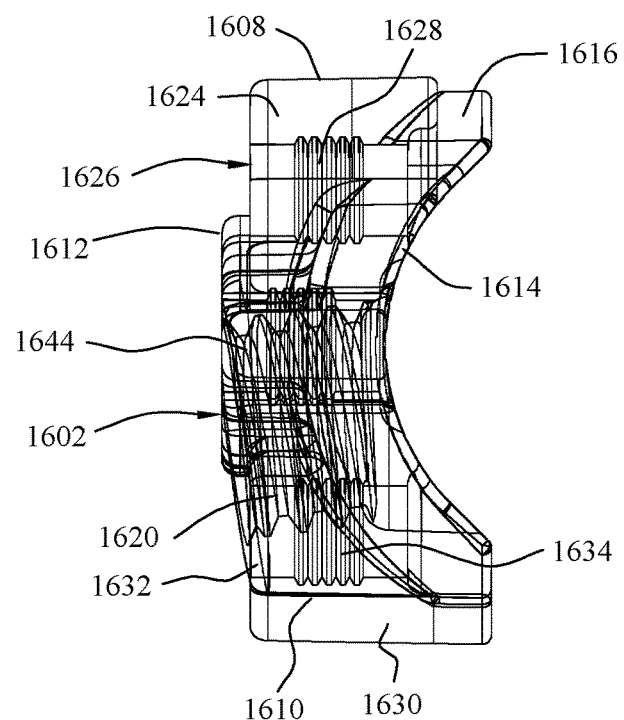
FIG. 77 is a second end transverse view of the guide of FIG. 73, in accordance with an aspect of the present invention.
Figure 78:
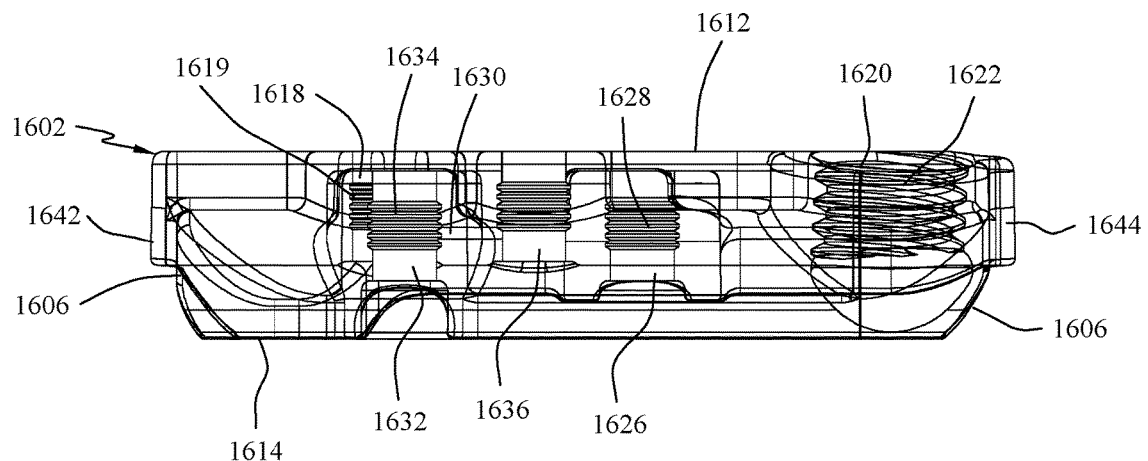
FIG. 78 is a first side transverse view of the guide of FIG. 73, in accordance with an aspect of the present invention.
Figure 79:
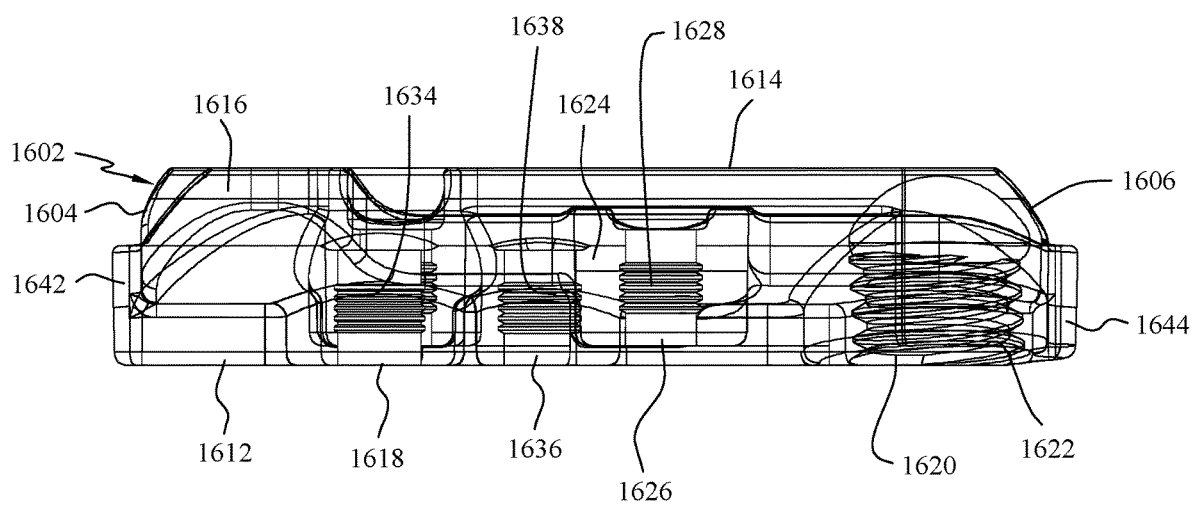
FIG. 79 is a second side transverse view of the guide of FIG. 73, in accordance with an aspect of the present invention.
Figure 80:
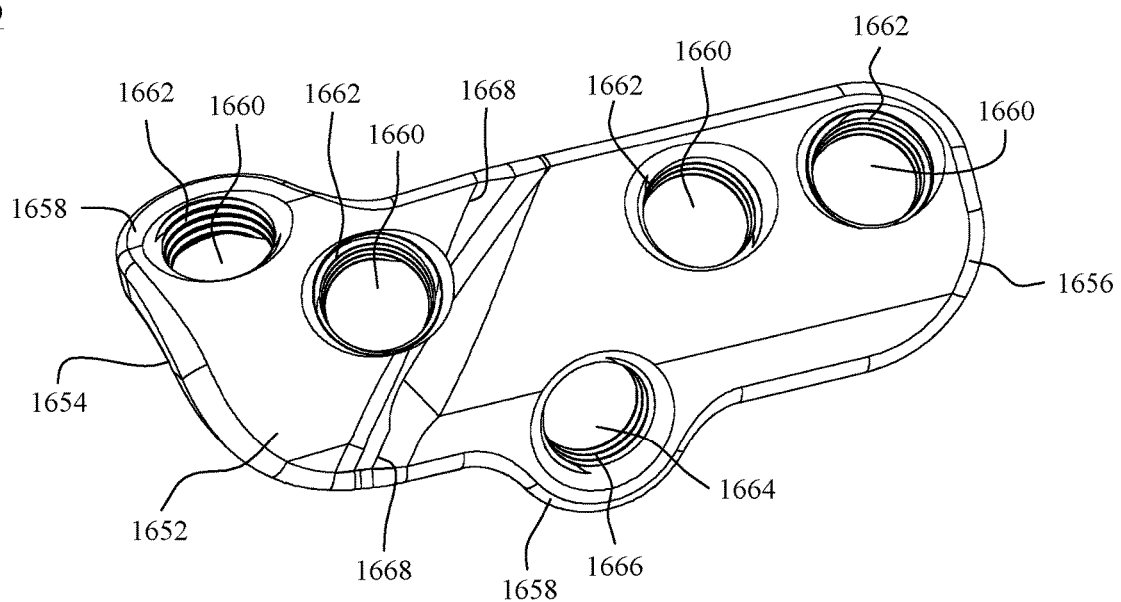
FIG. 80 is a perspective view of a bone plate, in accordance with an aspect of the present invention.

The body 1602 may also have a first extension 1624 projecting out from the first side 1608 near the center of the body 1602 and a second extension 1630 projecting out from the second side 1610 near the center of the body 1602, as shown in FIGS. 73-75. The first extension 1624 may include a first hole 1626 extending from the front surface 1612 to the back surface 1614. The first hole 1626 may be, for example, sized to receive a guide wire (not shown) or alternatively may include a wire guide 1628. The wire guide 1628 may, for example, have an outer diameter sized to mate with the first hole 1626 and an inner diameter sized to receive a wire. The wire guide 1628 may also include, for example, threads on the interior to couple to threads on the guide wire (not shown). In addition, the wire guide 1628 may include, for example, threads on the outer diameter for mating with threads within the first hole 1626.

As shown in FIGS. 73-75, the second extension 1630 may include a second hole 1632 extending from the front surface 1612 to the back surface 1614. The second hole 1632 may be, for example, sized to receive a guide wire (not shown) or alternatively may include a wire guide 1634. The wire guide 1634 may, for example, have an outer diameter sized to mate with the second hole 1632 and an inner diameter sized to receive a wire. The wire guide 1634 may also include, for example, threads on the interior to couple to threads on the guide wire (not shown). In addition, the wire guide 1634 may include, for example, threads on the outer diameter for mating with threads within the second hole 1632.

Further, as shown in FIGS. 73-75, the body 1602 may also include a third hole 1636 positioned along the same angle axis that aligns with and is between the first extension 1624 and the second extension 1630. The third hole 1636 may be, for example, sized to receive a guide wire (not shown) or alternatively may include a wire guide 1638. The wire guide 1638 may, for example, have an outer diameter sized to mate with the third hole 1636 and an inner diameter sized to receive a wire. The wire guide 1638 may also include, for example, threads on the interior to couple to the threads on the guide wire (not shown). In addition, the wire guide 1638 may include, for example, threads on the outer diameter for mating with threads within the third hole 1636. The front surface 1612 may also include an alignment protrusion 1640 which extends from the first end 1604 to the second end 1606 and is positioned along the longitudinal axis of the body 1602. The longitudinal axis extends between the first end 1604 and the second end 1606 of the guide 1600. The alignment protrusion 1640 may include a first portion 1642 near the first end 1604 and a second portion 1644 near the second end 1606. The first portion 1642 may slightly protrude past the first end 1604 of the body 1602 and the second portion 1644 may slightly protrude past the second end 1606 to act as alignment tabs for positioning the guide 1600 on a patient's bone. The third hole 1636 may be positioned along the alignment protrusion 1640.

Figure 81:
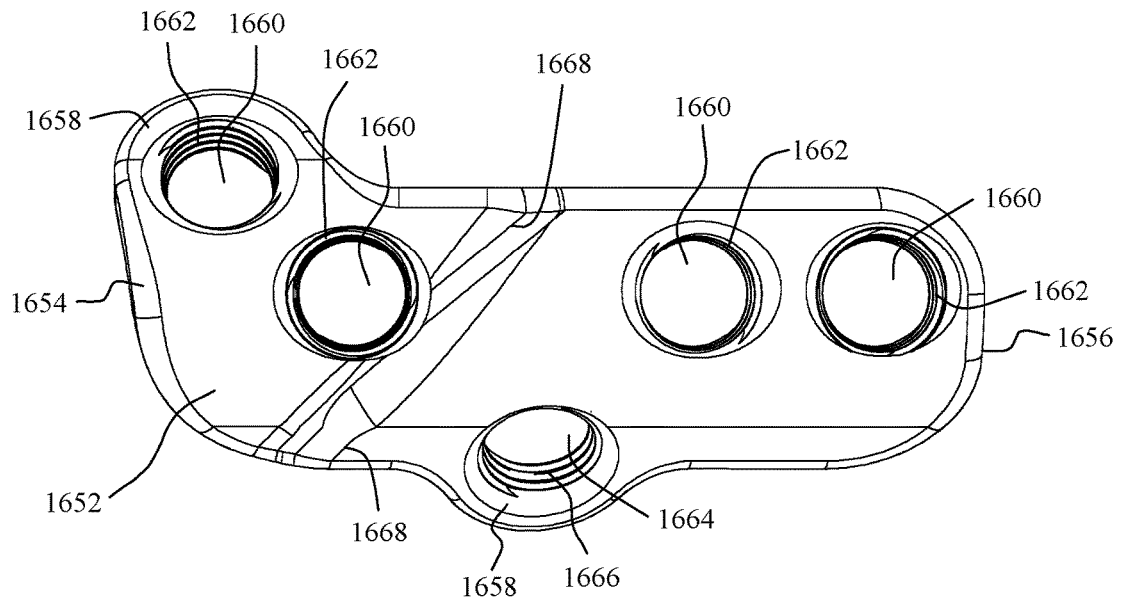
FIG. 81 is a top view of the plate of FIG. 80, in accordance with an aspect of the present invention.
Figure 86:
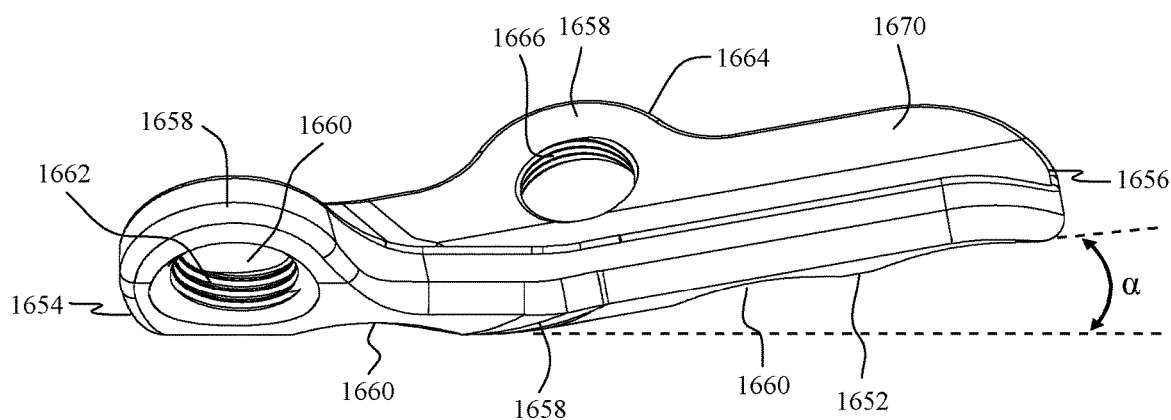
FIG. 86 is a second side view of the plate of FIG. 80, in accordance with an aspect of the present invention.

FIGS. 80-86 show another embodiment of a bone plate 1650. The bone plate 1650 includes a predetermined correction built into the profile of the plate. The bone plate 1650 may also include a multi-faceted shape that produces bone correction motion as the plate 1650 is fastened to the bone portions or fragments. The bone plate 1650 may come in multiple sizes based on the desired angle of correction of the bone, for example, the bone plate 1650 may be offered in sizes to provide for between 2° and 20° of angular correction, or more specifically, approximately 5°, 7.5°, 10°, 12.5°, or 15° of angular correction. The angle of correction provided by each plate 1650 may be determined by measuring the angle between the proximal bone axis and distal bone axis after the osteotomy is performed. The bone plate 1650 may also be configured for placement on either the medial side of the bone or the lateral side of the bone. The bone plate 1650 may include a body 1652 with a first end 1654 and a second end 1656. The bone plate 1650 may also include at least one tab portion 1658 extending away from the body 1652. The depicted bone plate 1650 includes a first tab portion 1658 extending away from a first side near the first end 1654 and a second tab portion 1658 extending away from a second side near the middle of the plate 1650. The first tab portion 1658 and second tab portion 1658 may be, for example, offset from each other. The bone plate 1650 may also include a plurality of openings 1660, 1664 for securing the bone plate 1650 to a bone, as shown in FIG. 100. As seen in FIG. 81, the bone plate 1650 may include, for example, five openings 1660, 1664 with two openings 1660 positioned near the first end 1654 of the plate 1650, two openings 1660 positioned near the second end 1656 of the plate 1650, and one opening 1664 positioned near a mid-point of the plate 1650. The openings 1660, 1664 may be, for example, threaded or tapered openings configured to receive locking or non-locking bone fasteners or screws. The opening 1664 may be positioned in the second tab portion 1658. The opening 1664 may be, for example, angled to allow for a fastener (not shown) to be inserted through the opening 1664 and cross the cut bone or osteotomy to engage both portions of the bone. The bone plate 1650 may also include at least one alignment marking 1668 for aligning with the osteotomy surface of the bone, for example, with the distal portion of a metatarsal bone after resection. The bone plate 1650 may include, for example, a first plate portion extending from the first end 1654 to approximately the at least one alignment marking 1668 and a second plate portion extending from the at least one alignment marking 1668 to the second end 1656. As shown in FIG. 86, the first plate portion may be angled with respect to the second plate portion by an angle α. The angle of correction α between the first and second plate portions may be, for example, approximately 1 to 30 degrees. The angle α defines the fixation of the bones after resection and fixation. The first plate portion and the second plate portion may each include, for example, concave bone contacting surfaces.

Figure 82:
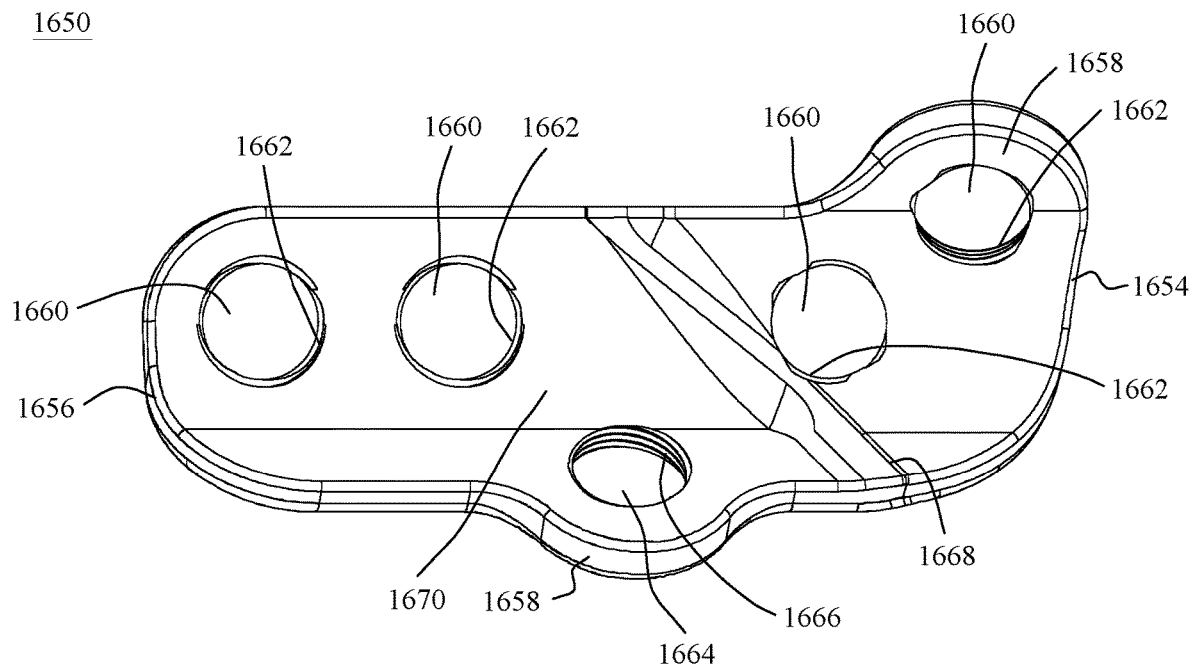
FIG. 82 is a bottom view of the plate of FIG. 80, in accordance with an aspect of the present invention.
Figure 83:
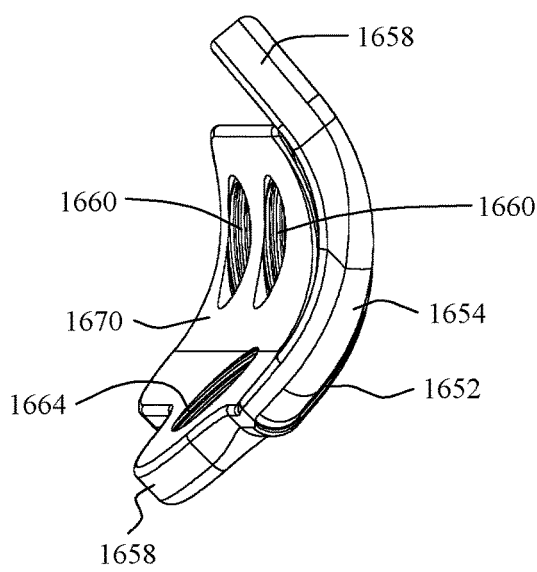
FIG. 83 is a first end view of the plate of FIG. 80, in accordance with an aspect of the present invention.
Figure 84:
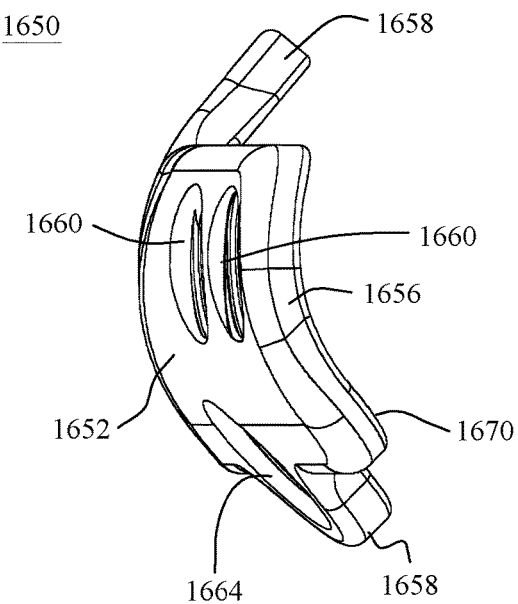
FIG. 84 is a second end view of the plate of FIG. 80, in accordance with an aspect of the present invention.
Figure 85:
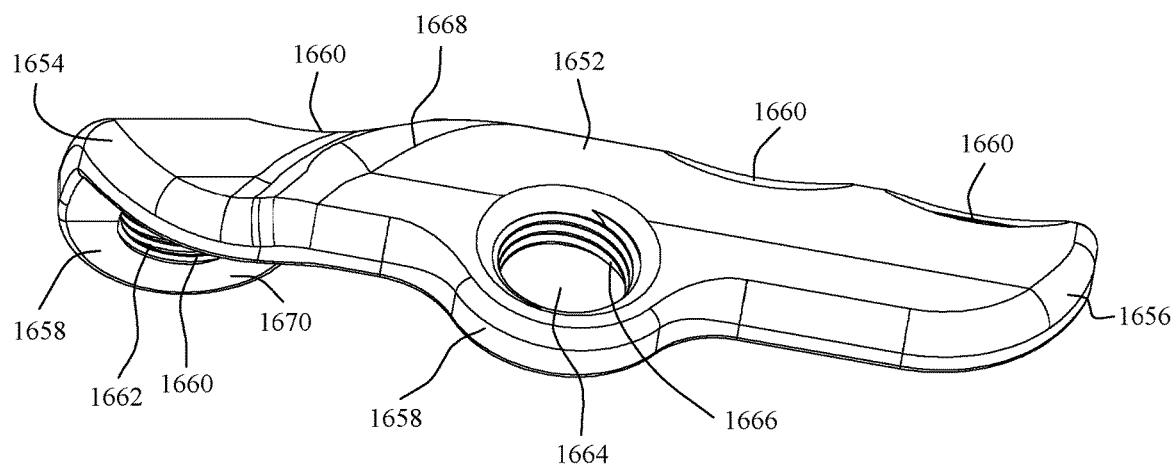
FIG. 85 is a first side view of the plate of FIG. 80, in accordance with an aspect of the present invention.

As shown in FIG. 82, the bottom or back surface of the bone plate 1650 may have, for example, at least one bone contacting surface 1670. The at least one bone contacting surface 1670 may include one or more surface textures disposed thereon and may include, for example, micro or macro grooved or irregular surface geometries disposed on the surface to aid in bone plate stability and fixation. The bone contacting surface may include, for example, a series of grooves, waves, serrations, scallops, or other contoured surface structures.

As shown in FIGS. 83-86, the bone plate 1650 may be, for example, curved to match the curvature of the outer cortex of the bone being resected. The plate 1650 may be contoured to provide specific angulation or re-angulation after bone alteration, i.e., an osteotomy. The plate 1650 provides the ability to create an angular change to the long axis of the bone by forming the angle in the bone contour surfaces, which are different from one end to the other. The tabs 1658 may provide additional stability for the bone-plate construct.

Figure 87:
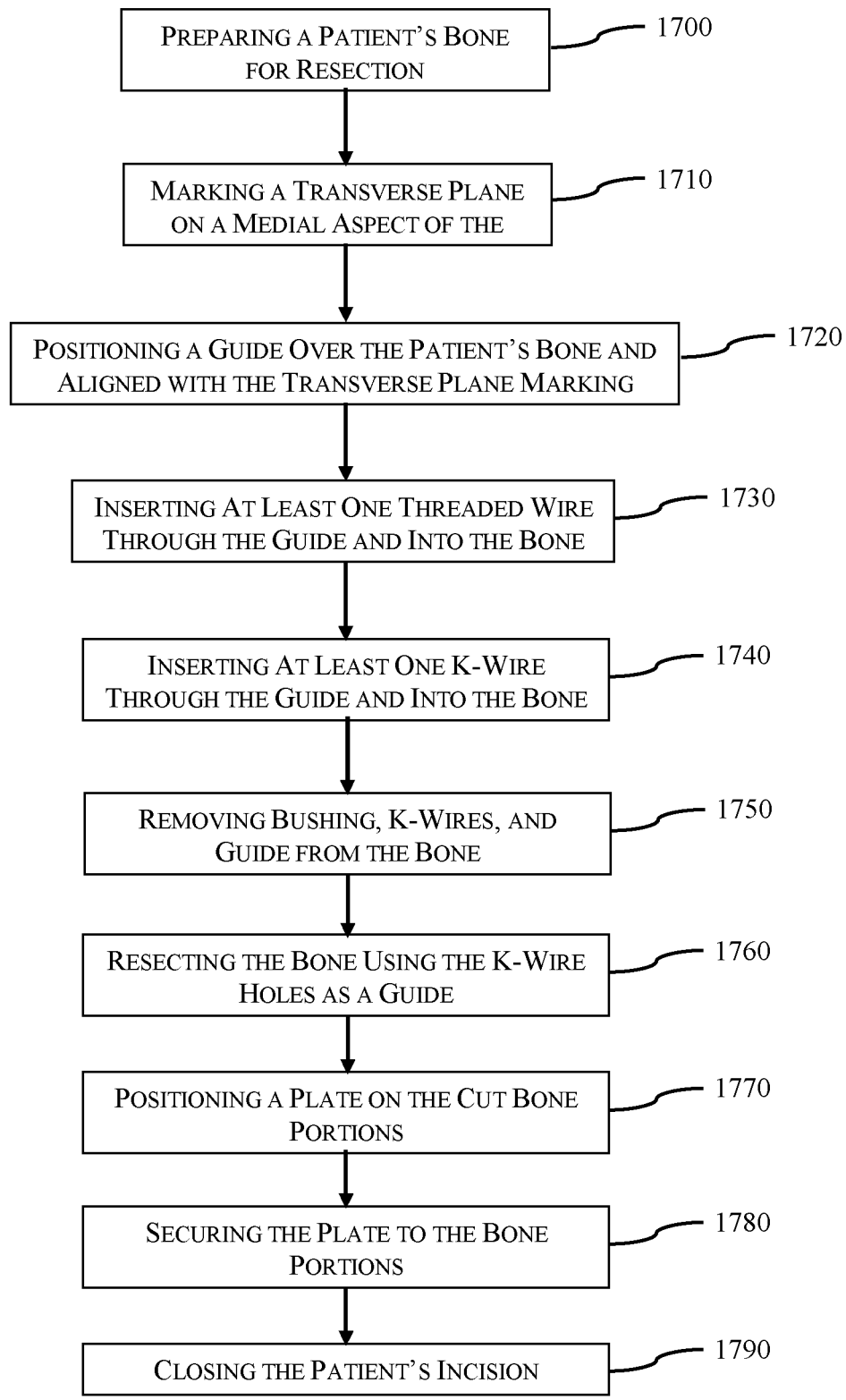
FIG. 87 depicts a method of using the guide of FIG. 73 and the plate of FIG. 80, in accordance with an aspect of the present invention.

A method of using the guide 1600 of FIGS. 73-79 and the plate 1650 of FIGS. 80-86 is shown in FIG. 87. The method for using the wire guide 1600 and the plate 1650 in accordance with one or more aspects of the present invention may include, for instance: preparing a patient's bone for resection 1700 and marking a transverse plane on a medial aspect of the patient's bone 1710. The method may also include positioning the guide over the patient's bone and aligning the guide with the marked transverse plane 1720. The method may further include inserting at least one threaded wire through the guide and into the patient's bone 1730 and forming a resection locator on the bone 1740. Forming a resection locator on the bone may include inserting at least one k-wire through the guide and into the patient's bone. In addition, the method may include removing the bushing, k-wires, and guide from the bone 1750 and resecting the bone using the k-wire holes as a guide 1760. The method may further include positioning the plate with respect to the bone portions 1770 and securing the plate to the bone portions 1780. Finally, the method may include closing the patient's incision 1790.

The method for using the k-wire guide 1600 and the plate 1650 of FIG. 87 is described in greater detail with respect to FIGS. 73-79 and 80-86. In one embodiment, the method of FIG. 87 may be performed, for example, utilizing a Mau osteotomy. The patient's bone may be prepared for resection by making an incision just distal to the cuneiform metatarsal joint medially to the interphalangeal joint. Then, the exostosis may be trimmed and the appropriate soft tissue releases of the interphalangeal joint performed. Once the surgical site is visible, a mark may be placed on the patient's bone, specifically the mark should be made on the transverse plane of the medial aspect of the bone. Next, the guide 1600 may be positioned over the bone and the first portion 1642 and the second portion 1644 of the alignment protrusion 1640 may be aligned with the transverse plane marking on the patient's bone. The guide 1600 may be positioned, for example, approximately 1 cm distal of the joint. The guide 1600 may then be held in position while a threaded wire or fastener (not shown) is inserted through the first opening 1618 of the guide 1600 and into the patient's bone through, for example, two cortices. While continuing to hold the guide 1600 in position, a second threaded wire or fastener (not shown) may be inserted through an opening in a bushing 1230 secured into the second opening 1620 of the guide 1600. The second threaded wire may also be inserted into the patient's bone through two cortices.

Once the guide 1600 is secured to the patient's bone, a first pin (not shown) may be inserted into the third hole 1636 of the guide 1600, a second pin (not shown) may be inserted into through the second hole 1632 of the guide 1600, and a third pin (not shown) may be inserted through the first hole 1626 of the guide 1600 and into both cortices of the bone. The k-wires may be, for example, inserted directly through the holes 1626, 1632, 1636 or through wire guides 1628, 1634, 1638 in each of the holes 1626, 1632, 1636, respectively. After the k-wires are inserted into the bone, the k-wires may be removed from the bones leaving three holes in the bone to act as a cut guide for the resection and the bushing 1230 may be removed from the guide 1600. In addition, the guide 1600 may be removed from the bone to expose the holes formed by the k-wires.

The surgeon may then perform the resection cutting the patient's bone along the holes created by the k-wires. The surgeon may complete the resection by performing an optional scarf cut. The patient's bone will then have a first portion and a second portion, such as, first portion 1306 and second portion 1308 as shown in FIG. 58, and the first threaded wire or fastener may be positioned in the first bone portion and the second threaded wire or fastener may be positioned in the second bone portion. Next, a plate 1650 may be aligned with and inserted over the threaded wires, such as shown in FIG. 59. The threaded wires may be inserted through two openings 1660 in the plate 1650. The threaded wires inserted through the guide 1600 are used as the location pins for placing the plate 1650 on the bone portions. The threaded wires also allow for full control of the bone portions or fragments before, during and after resection. Once the plate 1650 is positioned on the bone portions the plate 1650 may be secured to the bone portions as described in greater detail above with reference to FIGS. 60-63. The plate 1650 is designed to pull the bones to the proper angled position as the bones are secured to the plate 1650. After the plate 1650 is secured to the bone portions, the patient's incision may then be closed.

In another embodiment, a method of using the plate 1650 may include placing a plate 1650 including an angle over a mal-shaped bone and cutting the bone. The method may further include attaching the plate to the cut bone to change the location of the cut bone fragments from a non-anatomic position to an anatomic position to facilitate correction of the bone at the location of the cut.

In yet another embodiment, a method of using the k-wire guide 1600 and the plate 1650 may include temporarily fastening the guide 1600 to a bone using temporary fasteners and identifying a bone resection location. Once the bone resection location is identified, the guide 1600 may be removed and the temporary fasteners may be used to position the plate 1650. Next, the plate 1650 may be fixed to the bone using fasteners. Then, the temporary fasteners may be removed and final fasteners may be inserted into the bone to secure the plate 1650 to the bone portions or fragments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method of device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A bone plate system, comprising:
   a plate including a plurality of plate openings to receive fasteners to connect the plate to a bone;
   a resection guide having a first locator opening for receiving a wire to connect the guide to the bone and a second locator opening for receiving a second wire to connect the guide to the bone, and a plurality of holes for receiving at least a third wire to create a plurality of openings in the bone, the plurality of openings providing a guide for a cutting tool to resect the bone;
   the resection guide comprising:
      a body with a first end and a second end;
      the first locator opening in the first end of the body;
      the second locator opening in the second end of the body;
      a first extension portion extending away from a first side near the first end;
      a second extension portion extending away from a second side near a middle of the body;
      a first hole of the plurality of holes positioned in the first extension portion;
      a second hole of the plurality of holes positioned adjacent to the first locator opening;
      the second locator opening positioned at the second end near a first side;
      a third hole of the plurality of holes positioned in the second extension; and
   the plate comprising a first plate portion at a first end of the plate and a second plate portion at a second end of the plate, the first plate portion and the second plate angled relative to each other to provide a correction to a profile of the bone.

2. The bone plate system of claim 1, wherein the plate comprises:
   a body with a first end and a second end;
   a first plate opening of the plurality of plate openings positioned in the first end and a second plate opening of the plurality of plate openings positioned in the second end; and
   an alignment marking disposed on a surface of the body for alignment with an osteotomy surface of the bone.

3. The bone plate system of claim 2, wherein the plate further comprises:
   a first tab extending away from a first side near a center of the body; and
   a second tab extending away from a second side near a center of the body.

4. The bone plate system of claim 3, wherein the plate further comprises:
   a first hole positioned in the first tab;
   a second hole positioned in the second tab; and
   a third hole positioned between the first hole and the second hole and along an axis extending between the first hole and the second hole.

5. The bone plate system of claim 2, wherein the alignment marking is positioned along a longitudinal axis of the body and wherein the longitudinal axis extends between the first end and the second end.

6. The bone plate system of claim 2, wherein the plate further comprises:
   at least one wire guide positioned within at least one of the first plate opening, the first hole, the second hole, and the third hole; and
   a bushing coupled to the second plate opening.

7. The bone plate system of claim 1, wherein the plate is angled along the longitudinal axis such that a longitudinal axis of said first plate portion and a longitudinal axis of said second plate portion are angled relative to each other longitudinally to provide a concave bottom surface for contacting the bone.

8. The bone plate system of claim 1, wherein the plate is nonlinear in the transverse plane.

9. The bone plate system of claim 1, wherein the resection guide is made of a transparent material.

* * * * *